United States Patent
Sah et al.

(10) Patent No.: US 7,582,745 B2
(45) Date of Patent: Sep. 1, 2009

(54) COMPOSITIONS AND METHODS FOR INHIBITING EXPRESSION OF NAV1.8 GENE

(75) Inventors: Dinah Sah, Boston, MA (US); Maria Frank-Kamenetsky, Brookline, MA (US); Anke Geick, Bayreuth (DE); Philipp Hadwiger, Altenkunstadt (DE); Ingo Roehl, Memmelsdorf (DE); Pamela Tan, Kulmbach (DE); Hans-Peter Vornlocher, Bayreuth (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/593,099

(22) Filed: Nov. 3, 2006

(65) Prior Publication Data

US 2007/0105806 A1        May 10, 2007

Related U.S. Application Data

(60) Provisional application No. 60/733,816, filed on Nov. 4, 2005, provisional application No. 60/741,586, filed on Dec. 2, 2005, provisional application No. 60/763,202, filed on Jan. 26, 2006, provisional application No. 60/795,443, filed on Apr. 27, 2006, provisional application No. 60/849,364, filed on Oct. 4, 2006.

(51) Int. Cl.
C07H 21/04        (2006.01)
A61K 31/70        (2006.01)
C12N 5/00         (2006.01)

(52) U.S. Cl. .................... 536/24.5; 514/44; 435/325
(58) Field of Classification Search .................. None
See application file for complete search history.

(56) References Cited

U.S. PATENT DOCUMENTS

| | | |
|---|---|---|
| 3,687,808 A | 8/1972 | Merigan, Jr. et al. |
| 4,868,116 A | 9/1989 | Morgan et al. |
| 4,980,286 A | 12/1990 | Morgan et al. |
| 4,981,957 A | 1/1991 | Lebleu et al. |
| 5,034,506 A | 7/1991 | Summerton et al. |
| 5,118,800 A | 6/1992 | Smith et al. |
| 5,212,295 A | 5/1993 | Cook |
| 5,319,080 A | 6/1994 | Leumann |
| 5,328,470 A | 7/1994 | Nable et al. |
| 5,359,044 A | 10/1994 | Cook et al. |
| 5,393,878 A | 2/1995 | Leumann |
| 5,446,137 A | 8/1995 | Maag et al. |
| 5,446,786 A | 8/1995 | Shtulman |
| 5,489,677 A | 2/1996 | Sanghvi et al. |
| 5,514,785 A | 5/1996 | Van Ness et al. |
| 5,519,134 A | 5/1996 | Acevedo et al. |
| 5,521,302 A | 5/1996 | Cook |
| 5,567,427 A | 10/1996 | Papadakis |
| 5,567,811 A | 10/1996 | Misiura et al. |
| 5,587,361 A | 12/1996 | Cook et al. |
| 5,591,722 A | 1/1997 | Montgomery et al. |
| 5,597,909 A | 1/1997 | Urdea et al. |
| 5,602,240 A | 2/1997 | De Mesmaeker et al. |
| 5,610,300 A | 3/1997 | Altmann et al. |
| 5,627,053 A | 5/1997 | Usmann et al. |
| 5,639,873 A | 6/1997 | Barascut et al. |
| 5,646,265 A | 7/1997 | McGee |
| 5,658,873 A | 8/1997 | Bertsch-Frank et al. |
| 5,670,633 A | 9/1997 | Cook et al. |
| 5,700,920 A | 12/1997 | Altmann et al. |
| 5,735,814 A | 4/1998 | Elsberry et al. |
| 5,814,014 A | 9/1998 | Elsberry et al. |
| 5,859,221 A | 1/1999 | Cook et al. |
| 6,042,579 A | 3/2000 | Elsberry et al. |
| 6,093,180 A | 7/2000 | Elsberry |
| 6,127,533 A | 10/2000 | Cook et al. |
| 6,166,197 A | 12/2000 | Cook et al. |
| 6,172,209 B1 | 1/2001 | Manoharan et al. |
| 6,271,358 B1 | 8/2001 | Manoharan et al. |
| 6,551,290 B1 | 4/2003 | Elsberry et al. |
| 6,594,880 B2 | 7/2003 | Elsberry |
| 6,945,969 B1 | 9/2005 | Morris et al. |
| 7,189,222 B2 | 3/2007 | Elsberry |

(Continued)

FOREIGN PATENT DOCUMENTS

DE        101 00 586.5        4/2002

(Continued)

OTHER PUBLICATIONS

Akopian et al., "A Tetrodotoxin-Resistant Voltage-Gated Sodium Channel Expressed by Sensory Neurons," *Nature*, 379: 257-262 (1996).

(Continued)

*Primary Examiner*—Richard Schnizer
(74) *Attorney, Agent, or Firm*—Fenwick & West LLP

(57) ABSTRACT

The invention relates to a double-stranded ribonucleic acid (dsRNA) for inhibiting the expression of the Nav1.8 gene (Nav1.8 gene), comprising an antisense strand having a nucleotide sequence which is less that 25 nucleotides in length and which is substantially complementary to at least a part of the Nav1.8 gene. The invention also relates to a pharmaceutical composition comprising the dsRNA together with a pharmaceutically acceptable carrier; methods for treating diseases caused by the expression of the Nav1.8 gene using the pharmaceutical composition; and methods for inhibiting the expression of the Nav1.8 gene gene in a cell.

11 Claims, 15 Drawing Sheets

U.S. PATENT DOCUMENTS

| | | | | |
|---|---|---|---|---|
| 2003/0143732 | A1* | 7/2003 | Fosnaugh et al. | 435/325 |
| 2006/0199779 | A1* | 9/2006 | Goregaoker et al. | 514/44 |

FOREIGN PATENT DOCUMENTS

| | | |
|---|---|---|
| WO | WO 89/02468 | 3/1989 |
| WO | WO 89/05345 | 6/1989 |
| WO | WO 89/07136 | 8/1989 |
| WO | WO 92/07573 | 5/1992 |
| WO | WO 93/07883 | 4/1993 |
| WO | WO 99/32619 | 7/1999 |
| WO | WO 99/53050 | 10/1999 |
| WO | WO 99/61631 | 12/1999 |
| WO | WO 00/44895 | 8/2000 |

OTHER PUBLICATIONS

Armentano et al., "Expression of Human Facot IX in Rabbit Hepatocytes by Retrovirus-Mediated Gene Transfer: Potential for Gene Therapy of hemophilia B" *Proc. Natl. Acad. Sci. USA* 87: 6141-6145 (1990).

Berkner, K., "Development of Adenovirus Vectors for the Expression of Heterologous Genes," *Biotechniques*, 6(7): 616-629 (1988).

Bonica, J., "Past and Current Status of Pain Research and Therapy," *Seminars in Anesthesia* 5(2): 82-99 (1986).

Braasch et al., "Locked Nucleic Acid (LNA): Fine-Tuning the Recognition of DNA and RNA", *Chemistry & Biology*, 8: 1-7 (2001).

Bucchini et al., "Pancreatic Expression in Human Insulin Gene in Transgenic Mice" *Proc. Natl. Acad. Sci. USA*, 83: 2511-2515 (1986).

Chaplan et al., "Quantitative Assessment of Tactile Allodynia in the Rat Paw," *Journal of Neuroscience Methods* 53:55-63 (1994).

Chen et al., "Gene Therapy for Brain Tumors: Regression of Experimental Gliomas by Adenovirus-Mediated Gene Transfer in vivo", *Proc. Natl. Acad. Sci. USA*, 91: 3054-3057 (1994).

Chowdhury et al., "Long-Term Improvements of Hypercholesterolemia After ex Vivo Gene Therapy in LDLR-Deficient Rabbits," *Science*, 254(5039): 1802-1805 (1991).

Cone, R. and Mulligan, R., "High-Efficiency Gene Transfer into Mammalian Cells: Generation of Helper-Free Recombinant Retrovirus with Broad Mammalian Host Range," *Proceedings of the National Academy of Sciences of the United States of America*, 81(20): 6349-6353 (1984).

Cook, P. Dan, "Medicinal Chemistry of Antisense Oligonuceotides—Future Opportunities", *Anti-Cancer Drug Design*, 6: 587-607 (1991).

Cornetta et al., "Safety Issues Related to Retroviral-Mediated Gene Transfer in Humans," *Human Gene Therapy* 2:5-14 (1991).

Couture et al., "Anti-Gene Therapy: The Use of Ribozymes to Inhibit Gene Function" TGI 12(12): 510-515 (1996).

Crooke et al., "Pharmacokinetic Properties of Several Novel Oligonucleotide Analogs in Mice" *The Journal of Pharmacology and Experimental Therapeutics*, 277(2): 923-937 (1996).

Dai et al., "Gene Therapy Via Primary Myoblasts: Long-Term Expression of Factor IX Protein Following Transplantation in vivo" *Proc. Natl. Acad. Sci. USA*, 89: 10892-10895 (1992).

Danos, O. and Mulligan, R., "Safe and Efficient Generation of Recombinant Retroviruses with Amphotropic and Ecotropic Host Ranges" *Proc. Natl. Acad. Sci. USA*, 85: 6460-6464 (1988).

Delgado et al., "The Uses and Properties of PEG-Linked Proteins," *Critical Reviews in Therapeutic Drug Carrier Systems* 9(3,4): 249-304 (1992).

Dixon, W.J., "Efficient Analysis of Experimental Observations," *Ann. Rev. Pharmacol. Toxicol.* 20: 441-462 (1980).

Docherty, K. and Clark, A., "Nutrient Regulation of Insulin Gene Expression," *The FASEB Journal* 8: 20-27 (1994).

Eglitis et al.,"Gene Expression in Mice After High Efficiency Retroviral-Mediated Gene Transfer," *Science* 230(4732): 1395-1398 (1995).

Elbashir et al., "Functional Anatomy of siRNAs for Mediating Efficient RNAi in Drosophila melanogatser embryo lysate" *The EMBO Journal* 20(23): 6877-6888 (2001).

Ferry et al., "Retroviral-Mediated Gene Transfer into Hepatocytes in vivo" *Proc. Natl. Acad. Sci. USA*, 88: 8377-8381 (1991).

Gassmann et al., "Maintenance of an Extrachromosomal Plasmid Vecot in Mouse Embryonic Stem Cells" *Proc. Natl. Acad. Sci. USA*, 92: 1292-1296 (1995).

Gold et al., "Redistribution of $Na_v1.8$ in Uninjured Axons Enables Neuropathic Pain," *The Journal of Neuoscience* 23(1): 158-166 (2003).

Hamm et al., "Incorporation of 2'-Deoxy-2' mercaptocytidine into Oligonucleotides via Phosphoramidite Chemistry" *J. Org. Chem.*, 62: 3415-3420 (1997).

Hargreaves et al., "A New and Sensitive Method for Measuring Thermal Nociception in Cutaneous Hyperalgesia," *Pain* 32: 77-99 (1988).

Hsu et al., "Immunogenicity of Recombinant Adenovirus-Respiratory Syncytial Virus Vaccines with Adenovirus Types 4, 5, and 7 Vecotrs in Dogs and Chimpanzee," *The Journal of Infectious Diseases* 166:769-775 (1992).

Huber et al., "Retroviral-Mediated Gene Therapy for the Treatment of Hepatocellular Carcinoma: An Innovative Approach for Cancer Therapy" *Proc. Natl. Acad. Sci. USA*, 88: 8039-8043 (1991).

Hwu et al., "Functional and Molecular Characterization of Tumor-Infiltrating Lymphocytes Transduced with Tumor Necrosis Factor-α cDNA for the Gene Therapy of Cancer in Humans," *The Journal of Immunology* 150: 4104-4115 (1993).

Jain, KK., "A Guide to Drug Evaluation for Chronic Pain," *Emerging Drugs*, 5:241-257 (2000).

Jensen, T.S., "Anticonvulsants in Neuropathic Pain: Rationale and Clinical Evidence," *European Journal of Pain*, 6(Suppl. A): 61-68 (2002).

Kabanov et al., "A New Class of Antivirals: Antisense Oligonucleotides Combined with a Hydrophobic Substituent Effictively Inhibit Influenza Virus Reproduction and Synthesis of Virus-Specific Proteins in MDCK Cells" FEB 259(2): 327-330 (1990).

Kay et al., "Hepatic Gene Therapy: Persistent Expression of Human αl-Antitypsin in Mice after Direct Gene Delivery in Vivo," *Human Gene Therapy* 3: 641-647 (1992).

Khasar et al., "A Tetrodotoxin-Resistant Sodium Current Mediates Inflammatory Pain in the Rat," *Neuroscience Letters* 256:17-20 (1998).

Koshkin et al., "LNA (Locked Nucleic Acids): Synthesis of the Adenine, Cytosine, Guanine, 5-Mehtylcytosine, Thymine and Uracil Bicyclonucleoside Monomers, Oligomerisation and Unprecedented Nucleic Acid Recognition" *Tetrahedron* 54:3607-3630 (1998).

Lai et al., "Blockade of Neuropathic Pain by Antisense Targeting of Tetrodotoxin-Resistant Sodium Channels in Sensory Neurons," *Methods of Enzymology* 314: 201-213 (1999).

Lai et al., "Inhibition of Neuropathic Pain by Decreased Expression of the Tetrodoxin-Resistant Sodium Channel, NaC1.8," *Pain* 95:143-152 (2002).

Letsinger et al., "Cholesteryl-Conjugated Oligonucleotides: Synthesis, Properties, and Activity as Inhibitors of replication of Human Immunodeficiency Virus in Cell Culture" *Proc. Natl. Acad. Sci. USA* 86: 6533-6556 (1989).

Li et al., "Folate-Mediated Targeting of Antisense Oligodeoxynucleotides to Ovarian Cancer Cells" *Pharmaceutical Research* 15(10): 1540-1545 (1998).

Manoharan et al., "Chemical Modifications to Improve Uptake and Bioavailability of Anisense Oligonucleotides", *Annals of the New York Academy of Sciences*, 660: 306-308 (1992).

Manoharan et al., "Cholic Acid-Oligonucleotide Conjugates for Antisense Applications" *Bioorganic & Medicinal Chemistry Letters* 4(8): 1053-1060 (1994).

Manoharan et al., "Introduction of a Lipophilic Thioehter Tether in the Minor Groove of Nucleic Acids for Antisense Applications" *Bioorganic & Medicinal Chemistry Letters* 13(12):2765-2770 (1993).

Manoharan et al., "Lipidic Nucleic Acids" *Tetrahedron Letters* 36(21): 3651-3654 (1995).

Manoharan et al., "Oligonucleotide Conjugates: Alteration of the Pharmacokinetic Properties of Antisense Agents" *Nucleosides & Nucleotides* 14(3-5): 969-973 (1995).

Manoharan, M., "Oligonucleotide Conjugates as Potential Antisense Drugs with Improved Uptake, Biodistribution, Targeted Delivery, and Mechanism of Action" *Antisense & Nucleic Acid Drug Development* 12: 103-128 (2002).

Mao i., "Systemic Lidocaine for Neuropathic Pain Relief," *Pain* 87: 7-17 (2000).

Martin, P., "Ein neuer Zugang zu 2'-O-Alkylribonucleosiden und Eigenschaften deren Oligonucleotide" *Helvetica Chemica Activa* 78: 486-504 (1995).

McQuany, H., "Neuropathic Pain: Evidence Matters," *European Journal of Pain* 6(Suppl. A.) 11-18 (2002).

Mishra et al., "Improved Leishmanicidal Effect of Phosphorotioate Antisense Oligonucleotides by LDL-Mediated Delivery" *Biochimica et Biophysica Acta* 1264: 229-237 (1995).

Muzyczka, N., "Use of Adeno-Associated Virus as a General Transduction Vector for Mammalian Cells," *Current Topics in Microbiology and Immunology*, 158: 97-129 (1992).

Nielsen et al., "Sequence-Selective Recognition of DNA by Strand Displacement with a Thymine-Subsituted Polyamide" *Science* 254 (5037): 1497-1500 (1991).

Noda et al., "A Single Point Mutation Confers Tetrodotoxin and Saxitoxin Insensitivity on the Sodium Channel II," *FEB* 259(1): 213-216 (1989).

Oberhauser et al., "Effective Incorporation of 2'-O-Methly-Oligoribonucleotides Into Liposomes and Enhanced Cell Association Through Modification with Thiocholesterol" *Nucleic Acids Research*, 20(3): 533-538 (1992).

Obika et al., "Stability and Structural Features of the Duplexes Containing Nucleoside Analogues with a Fixed N-Type Conformation, 2'-O,4'-C-Methyleneribonucleosides" *Tetrahedron Letters* 39: 5401-5404 (1998).

Ouchi et al., "Synthesis and Antitumor Activity of poly(Ethylene Glycol)s Linked to 5-Fluorouracil Via A Urethane or Urea Bond" *Drug Design and Discovery*, 9: 93-105 (1992).

Polushin et al., "Synthesis of Oligonucleotides Containing 2'-Azido- and 2'-Amino-2'Deoxyuridine Using Phosphotriester Chemistry" *Tetrahedron Letters* 37(19): 3227-3230 (1996).

Porreca et al., "A Comparison of the Potential Role of the Tetrodotoxin-Insensitive Sodium Channels, PN3/SNS and NaN. SNS2, In Rat Models of Chronic Pain" *Proc. Natl. Acad. Sci. USA*, 96: 7640-7644 (1999).

Ravasio, N., "Selective Hydrogenations Promoted by Copper Catalysts. 1. Chemoselectivity, Regioselectivity, and Stereoselectivity in the Hydrogenation of 3-Substituted Steroids" *J. Org. Chem.* 56: 4329-4333 (1991).

Rosenfeld et al., "Adenovirus-Mediated Transfer of a Recombinant #1-Antitryspin Gene to the Lung Epithelium in Vivo," *Science* 252(5004): 431-434 (1991).

Rosenfeld et al., "In Vivo Transfer of the Human Cystic Fibrosis Transmembrane Conductance Regulator Gene to the Airway Epithelium," *Cell* 68:143-155 (1992).

Rozen, T., "Antiepileptic Drugs in the Management of Cluster Headache and Trigeminal Neuralgia," *Headache* 41:S25-S32 (2001).

Saison-Behmoaras et al., "Short Modified Antisense Oligonucleotides Directed Against Ha-ras Point Mutation Induce Selective Cleavage of the mRNA and Inhibit T24 Cells Proliferation" *EMBO J.*, 10: 1111-1118 (1991).

Sanghvi, Y. S., "Oligoribonucleotides as Drugs?" Chapter 15, *Antisense Research and Applications*, pp. 289-302 (1993).

Secrist et al., "Synthesis and Biological Activity of 4'Thionucleosides," *Program & Abstracts, Tenth International Roundtable, Nucleosides, Nucleotides and their Biological Applications*, Park City, Utah, Sep. 16-20, Abstract 21, 1992.

Shea et al., "Synthesis, Hybridization Properties and Antiviral Activity of Lipid-Oligodeoxynucleotide Conjugates" *Nucleic Acids Research* 18(13): 3777-3783 (1990).

Sindrup et al., "Efficacy of Pharmalogical Treatments of Neuropathic Pain: An Update and Effect Related to Mechanism of Drug Action," *Pain* 83: 389-400 (1999).

Svinarchuk et al., "Inhibition of HIV Proloferation in MT-4 Cells by Antisense Oligonucleotide Conjugated to Lipophilic Groups" *Biochimie* 75: 49-54 (1993).

Thomson et al., "Synthesis and Properties of Diuridine Phosphate Analogues Containing Thio and Amino Modifications," *J. Org. Chem.* 61: 6273-6281 (1996).

Tremont-Lukats et al., "Anticonvulsants for Neuropathic Pain Syndromes," *Drugs* 60(5): 1029-1052 (2000).

Van Beusechem et al., "Long-Term Expression of Human Adenosine Deaminase in Rhesus Monkeys Transplanted With Retrovirus-Infected Bone-Marrow Cells" *Proc. Natl. Acad. Sci. USA*, 89: 7640-7644 (1992).

Wagner, Richard W., "The State of the Art in Antisense Research" *Nature Medicine* 1(11): 1116-1118 (1995).

Waxman et al., "Sodium Channels and Pain" *Proc. Natl. Acad. Sci. USA*, 96: 7635-7639 (1999).

Waxman et al., "Voltage-Gated Sodium Channels and the Molecular Pathogenesis of Pain: A Review," *Journal of Rehabilitation Research and Development*, 37(5): 517-528 (2000).

Williams et al., "Thermodynamic Comparison of the Salt Dependence of Natural RNA Hairpins and RNA Hairpins with Non-Nucleotide Spacers," *Biochemistry* 35: 14665-14670 (1996).

Wilson et al., "Retrovirus-Mediated Transduction of Adult Hepatocytes" *Proc. Natl. Acad. Sci. USA*, 85: 3014-3018 (1988).

Yang et al., "Evidence That Processed Small dsRNAs May Mediate Sequence-Specific mRNA Degradation during RNAi in *Drosophila embryos*" *Current Biology* 10: 1191-1200 (2000).

Yoshimura et al., "The Involvement of Tetrodotoxin-Resistant Sodium Channel $Na_v1.8$ (PN3/SNS) in a Rat Model of Visceral Pain" *The Journal of Neuroscience*, 21(21): 8690-8696 (2001).

GenBank Accession No. NM_001003203 (Priority Date: Sep. 15, 2005), 4 pages.

GenBank Accession No. NM_017247 (Priority Date: Aug. 20, 2006), 5 pages.

GenBank Accession No. NM_006514 (Priority Date: Aug. 20, 2006), 6 pages.

GenBank Accession No. NM_009134 (Priority Date: Nov. 2, 2006), 6 pages.

Boese et al., "Mechanical Insights Aid Computational Short Interfering RNA Design," Methods in Enzymology 392:73-96, 2005.

Reynolds et al., "Rational siRNA design for RNA interference," Nature Biotechnology 22:326-330, 2004.

Mikami, M., et al., "Short Hairpin RNA-mediated Selective Knockdown of NaV1.8 Tetrodotoxin-resistant Voltage-gated Sodium Channel in Dorsal Root Ganglion Neurons," Anesthesiology, Oct. 2005, p. 828-836, vol. 103, No. 4.

PCT Invitation To Pay Additional Fees And, Where Applicable, Protest Fee, PCT/US2006/043252, Feb. 3, 2009, 2 pages.

* cited by examiner

* p < 0.05 vs PBS
^ p < 0.05 vs d3

SEQUENCE LISTING

```
<160> NUMBER OF SEQ ID NOS: 609

<210> SEQ ID NO 1
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 7, 8, 9, 10, 13, 14, 16, 18, 19
<223> OTHER INFORMATION: /mod_base = "2'-O-methyl corresponding base"
<220> FEATURE:
<221> NAME/KEY: modified_base
<222> LOCATION: 4, 5, 6, 11, 12, 15, 17
<223> OTHER INFORMATION: /mod_base = "2'-hydroxy corresponding base"

<400> SEQUENCE: 1
```

```
cccggauuuu aacuacacct t                                              21
```

```
<210> SEQ ID NO 2
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 9
<223> OTHER INFORMATION: /mod_base = "2'-O-methyl corresponding base"
<220> FEATURE:
<221> NAME/KEY: modified_base
<222> LOCATION: 1, 2, 3, 4, 6, 7, 8, 10, 11, 12, 13, 14, 15, 16, 17, 18,
      19
<223> OTHER INFORMATION: /mod_base = "2'-hydroxy corresponding base"

<400> SEQUENCE: 2
gguguaguua aauccgggt t                                               21
```

```
<210> SEQ ID NO 3
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 6, 7, 8, 9, 12, 13, 15, 17, 18
<223> OTHER INFORMATION: /mod_base = "2'-O-methyl corresponding base"
<220> FEATURE:
<221> NAME/KEY: modified_base
<222> LOCATION: 3, 4, 5, 10, 11, 14, 16, 19
<223> OTHER INFORMATION: /mod_base = "2'-hydroxy corresponding base"

<400> SEQUENCE: 3
ccggauuuua acuacaccat t                                              21
```

```
<210> SEQ ID NO 4
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 6, 10
<223> OTHER INFORMATION: /mod_base = "2'-O-methyl corresponding base"
<220> FEATURE:
<221> NAME/KEY: modified_base
<222> LOCATION: 1, 2, 3, 4, 5, 7, 8, 9, 11, 12, 13, 14, 15, 16, 17, 18,
      19
<223> OTHER INFORMATION: /mod_base = "2'-hydroxy corresponding base"

<400> SEQUENCE: 4
ugguguaguu aaauccggt t                                               21
```

```
<210> SEQ ID NO 5
<211> LENGTH: 21
<212> TYPE: DNA
<213> ORGANISM: Artificial sequence
```

```
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 6, 7, 8, 12, 13, 14, 15, 18, 19
<223> OTHER INFORMATION: /mod_base = "2'-O-methyl corresponding base"
<220> FEATURE:
<221> NAME/KEY: modified_base
<222> LOCATION: 1, 2, 4, 5, 9, 10, 11, 16, 17
<223> OTHER INFORMATION: /mod_base = "2'-hydroxy corresponding base"

<400> SEQUENCE: 5
gacaacccgg auuuuaacut t                                          21

<210> SEQ ID NO 6
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4
<223> OTHER INFORMATION: /mod_base = "2'-O-methyl corresponding base"
<220> FEATURE:
<221> NAME/KEY: modified_base
<222> LOCATION: 1, 2, 3, 5, 6, 7, 8, 9, 10, 11, 12, 13, 14, 15, 16, 17,
      18, 19
<223> OTHER INFORMATION: /mod_base = "2'-hydroxy corresponding base"

<400> SEQUENCE: 6
aguuaaaauc cggguuguct t                                          21

<210> SEQ ID NO 7
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 6, 9, 10, 13, 15
<223> OTHER INFORMATION: /mod_base = "2'-O-methyl corresponding base"
<220> FEATURE:
<221> NAME/KEY: modified_base
<222> LOCATION: 5, 7, 8, 11, 12, 14, 16, 17, 18, 19
<223> OTHER INFORMATION: /mod_base = "2'-hydroxy corresponding base"

<400> SEQUENCE: 7
ccuuacaacc agcgcaggat t                                          21

<210> SEQ ID NO 8
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 15
<223> OTHER INFORMATION: /mod_base = "2'-O-methyl corresponding base"
```

```
<220> FEATURE:
<221> NAME/KEY: modified_base
<222> LOCATION: 1, 2, 3, 4, 5, 6, 7, 8, 9, 10, 11, 12, 13, 14, 16, 17,
      18, 19
<223> OTHER INFORMATION: /mod_base = "2'-hydroxy corresponding base"

<400> SEQUENCE: 8
uccugcgcug guuguaaggt t                                              21

<210> SEQ ID NO 9
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 4, 5, 9, 10, 11, 12, 15, 16, 18
<223> OTHER INFORMATION: /mod_base = "2'-O-methyl corresponding base"
<220> FEATURE:
<221> NAME/KEY: modified_base
<222> LOCATION: 1, 2, 6, 7, 8, 13, 14, 17, 19
<223> OTHER INFORMATION: /mod_base = "2'-hydroxy corresponding base"

<400> SEQUENCE: 9
aacccggauu uuaacuacat t                                              21

<210> SEQ ID NO 10
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 7
<223> OTHER INFORMATION: /mod_base = "2'-O-methyl corresponding base"
<220> FEATURE:
<221> NAME/KEY: modified_base
<222> LOCATION: 1, 2, 4, 5, 6, 8, 9, 10, 11, 12, 13, 14, 15, 16, 17, 18,
      19
<223> OTHER INFORMATION: /mod_base = "2'-hydroxy corresponding base"

<400> SEQUENCE: 10
uguaguuaaa auccggguut t                                              21

<210> SEQ ID NO 11
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 5, 7, 10, 11, 12, 16, 17
<223> OTHER INFORMATION: /mod_base = "2'-O-methyl corresponding base"
<220> FEATURE:
<221> NAME/KEY: modified_base
<222> LOCATION: 2, 4, 6, 8, 9, 13, 14, 15, 18, 19
<223> OTHER INFORMATION: /mod_base = "2'-hydroxy corresponding base"

<400> SEQUENCE: 11
ugugcaugac ccgaacugat t                                              21
```

<210> SEQ ID NO 12
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 12, 16, 18
<223> OTHER INFORMATION: /mod_base = "2'-O-methyl corresponding base"
<220> FEATURE:
<221> NAME/KEY: modified_base
<222> LOCATION: 1, 3, 4, 5, 6, 7, 8, 9, 10, 11, 13, 14, 15, 17, 19
<223> OTHER INFORMATION: /mod_base = "2'-hydroxy corresponding base"

<400> SEQUENCE: 12
ucaguucggg ucaugcacat t                                              21

<210> SEQ ID NO 13
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 5, 6, 9, 11, 16, 18, 19
<223> OTHER INFORMATION: /mod_base = "2'-O-methyl corresponding base"
<220> FEATURE:
<221> NAME/KEY: modified_base
<222> LOCATION: 1, 3, 4, 7, 8, 10, 12, 13, 14, 15, 17
<223> OTHER INFORMATION: /mod_base = "2'-hydroxy corresponding base"

<400> SEQUENCE: 13
acaaccagcg caggauguct t                                              21

<210> SEQ ID NO 14
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3
<223> OTHER INFORMATION: /mod_base = "2'-O-methyl corresponding base"
<220> FEATURE:
<221> NAME/KEY: modified_base
<222> LOCATION: 1, 2, 4, 5, 6, 7, 8, 9, 10, 11, 12, 13, 14, 15, 16, 17,
      18, 19
<223> OTHER INFORMATION: /mod_base = "2'-hydroxy corresponding base"

<400> SEQUENCE: 14
gacauccugc gcugguugut t                                              21

<210> SEQ ID NO 15
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 4, 8, 9, 10, 11, 14, 15, 17, 19
<223> OTHER INFORMATION: /mod_base = "2'-O-methyl corresponding base"
<220> FEATURE:
<221> NAME/KEY: modified_base
<222> LOCATION: 1, 5, 6, 7, 12, 13, 16, 18
<223> OTHER INFORMATION: /mod_base = "2'-hydroxy corresponding base"

<400> SEQUENCE: 15
acccggauuu uaacuacact t                                              21

<210> SEQ ID NO 16
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 8
<223> OTHER INFORMATION: /mod_base = "2'-O-methyl corresponding base"
<220> FEATURE:
<221> NAME/KEY: modified_base
<222> LOCATION: 1, 2, 3, 5, 6, 7, 9, 10, 11, 12, 13, 14, 15, 16, 17, 18,
      19
<223> OTHER INFORMATION: /mod_base = "2'-hydroxy corresponding base"

<400> SEQUENCE: 16
guguaguuaa aauccgggut t                                              21

<210> SEQ ID NO 17
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 5, 6, 8, 12, 13, 16, 19
<223> OTHER INFORMATION: /mod_base = "2'-O-methyl corresponding base"
<220> FEATURE:
<221> NAME/KEY: modified_base
<222> LOCATION: 2, 7, 9, 10, 11, 14, 15, 17, 18
<223> OTHER INFORMATION: /mod_base = "2'-hydroxy corresponding base"

<400> SEQUENCE: 17
cauccuauga accaauagct t                                              21

<210> SEQ ID NO 18
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 11, 13
<223> OTHER INFORMATION: /mod_base = "2'-O-methyl corresponding base"
<220> FEATURE:
<221> NAME/KEY: modified_base
<222> LOCATION: 1, 2, 4, 5, 6, 7, 8, 9, 10, 12, 14, 15, 16, 17, 18, 19
```

```
<223> OTHER INFORMATION: /mod_base = "2'-hydroxy corresponding base"

<400> SEQUENCE: 18
gcuauugguu cauaggaugt t                                              21

<210> SEQ ID NO 19
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 5, 8, 9, 12, 14, 19
<223> OTHER INFORMATION: /mod_base = "2'-O-methyl corresponding base"
<220> FEATURE:
<221> NAME/KEY: modified_base
<222> LOCATION: 4, 6, 7, 10, 11, 13, 15, 16, 17, 18
<223> OTHER INFORMATION: /mod_base = "2'-hydroxy corresponding base"

<400> SEQUENCE: 19
cuuacaacca gcgcaggaut t                                              21

<210> SEQ ID NO 20
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 16
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 7, 8, 9, 10, 11, 12, 13, 14, 15, 17,
      18, 19
<223> OTHER INFORMATION: /mod_base = "2'-hydroxy corresponding base"

<400> SEQUENCE: 20
auccugcgcu gguuguaagt t                                              21

<210> SEQ ID NO 21
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 6, 7, 9, 11, 12, 15, 16, 17, 18
<223> OTHER INFORMATION: /mod_base = "2'-O-methyl corresponding base"
<220> FEATURE:
<221> NAME/KEY: modified_base
<222> LOCATION: 4, 5, 8, 10, 13, 14, 19
<223> OTHER INFORMATION: /mod_base = "2'-hydroxy corresponding base"

<400> SEQUENCE: 21
uuuaacuaca ccagcuuugt t                                              21

<210> SEQ ID NO 22
<211> LENGTH: 21
```

```
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 12, 16
<223> OTHER INFORMATION: /mod_base = "2'-O-methyl corresponding base"
<220> FEATURE:
<221> NAME/KEY: modified_base
<222> LOCATION: 2, 3, 4, 5, 6, 7, 8, 9, 10, 11, 13, 14, 15, 17, 18, 19
<223> OTHER INFORMATION: /mod_base = "2'-hydroxy corresponding base"

<400> SEQUENCE: 22
caaagcuggu guaguuaaat t                                              21

<210> SEQ ID NO 23
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 4, 6, 8, 11, 12, 13, 17, 18
<223> OTHER INFORMATION: /mod_base = "2'-O-methyl corresponding base"
<220> FEATURE:
<221> NAME/KEY: modified_base
<222> LOCATION: 1, 3, 5, 7, 9, 10, 14, 15, 16, 19
<223> OTHER INFORMATION: /mod_base = "2'-hydroxy corresponding base"

<400> SEQUENCE: 23
gugugcauga cccgaacugt t                                              21

<210> SEQ ID NO 24
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 11, 15, 17
<223> OTHER INFORMATION: /mod_base = "2'-O-methyl corresponding base"
<220> FEATURE:
<221> NAME/KEY: modified_base
<222> LOCATION: 2, 3, 4, 5, 6, 7, 8, 9, 10, 12, 13, 14, 16, 18, 19
<223> OTHER INFORMATION: /mod_base = "2'-hydroxy corresponding base"

<400> SEQUENCE: 24
caguucgggu caugcacact t                                              21

<210> SEQ ID NO 25
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 5, 6, 7, 8, 11, 12, 14, 16, 17
```

```
<223> OTHER INFORMATION: /mod_base = "2'-O-methyl corresponding base"
<220> FEATURE:
<221> NAME/KEY: modified_base
<222> LOCATION: 2, 3, 4, 9, 10, 13, 15, 18, 19
<223> OTHER INFORMATION: /mod_base = "2'-hydroxy corresponding base"

<400> SEQUENCE: 25
cggauuuuaa cuacaccagt t                                              21

<210> SEQ ID NO 26
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 7, 11
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 8, 9, 10, 12, 13, 14, 15, 16, 17, 18,
      19
<223> OTHER INFORMATION: /mod_base = "2'-hydroxy corresponding base"

<400> SEQUENCE: 26
cugguguagu uaaaauccgt t                                              21

<210> SEQ ID NO 27
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 6, 7, 10, 12, 17, 19
<223> OTHER INFORMATION: /mod_base = "2'-O-methyl corresponding base"
<220> FEATURE:
<221> NAME/KEY: modified_base
<222> LOCATION: 2, 4, 5, 8, 9, 11, 13, 14, 15, 16, 18
<223> OTHER INFORMATION: /mod_base = "2'-hydroxy corresponding base"

<400> SEQUENCE: 27
uacaaccagc gcaggaugut t                                              21

<210> SEQ ID NO 28
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 18
<223> OTHER INFORMATION: /mod_base = "2'-O-methyl corresponding base"
<220> FEATURE:
<221> NAME/KEY: modified_base
<222> LOCATION: 1, 3, 4, 5, 6, 7, 8, 9, 10, 11, 12, 13, 14, 15, 16, 17,
      19
<223> OTHER INFORMATION: /mod_base = "2'-hydroxy corresponding base"

<400> SEQUENCE: 28
```
acauccugcg cugguuguat t          21

<210> SEQ ID NO 29
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 4, 5, 6, 7, 9, 11, 12, 13, 15, 16, 18, 19
<223> OTHER INFORMATION: /mod_base = "2'-O-methyl corresponding base"
<220> FEATURE:
<221> NAME/KEY: modified_base
<222> LOCATION: 1, 2, 8, 10, 14, 17
<223> OTHER INFORMATION: /mod_base = "2'-hydroxy corresponding base"

<400> SEQUENCE: 29
ggucucugug cccauugcut t          21

<210> SEQ ID NO 30
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 10, 12
<223> OTHER INFORMATION: /mod_base = "2'-O-methyl corresponding base"
<220> FEATURE:
<221> NAME/KEY: modified_base
<222> LOCATION: 1, 2, 4, 5, 6, 7, 8, 9, 11, 13, 14, 15, 16, 17, 18, 19
<223> OTHER INFORMATION: /mod_base = "2'-hydroxy corresponding base"

<400> SEQUENCE: 30
agcaaugggc acagagacct t          21

<210> SEQ ID NO 31
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 7, 8, 9, 10, 12, 15, 19
<223> OTHER INFORMATION: /mod_base = "2'-O-methyl corresponding base"
<220> FEATURE:
<221> NAME/KEY: modified_base
<222> LOCATION: 4, 5, 6, 11, 13, 14, 16, 17, 18
<223> OTHER INFORMATION: /mod_base = "2'-hydroxy corresponding base"

<400> SEQUENCE: 31
cccaaguucu auggugagct t          21

<210> SEQ ID NO 32
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:

-continued

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 7, 9
<223> OTHER INFORMATION: /mod_base = "2'-O-methyl corresponding base"
<220> FEATURE:
<221> NAME/KEY: modified_base
<222> LOCATION: 1, 2, 3, 5, 6, 8, 10, 11, 12, 13, 14, 15, 16, 17, 18, 19
<223> OTHER INFORMATION: /mod_base = "2'-hydroxy corresponding base"

<400> SEQUENCE: 32
gcucaccaua gaacuugggt t                                              21

<210> SEQ ID NO 33
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 5, 6, 7, 8, 10, 13, 17, 18, 19
<223> OTHER INFORMATION: /mod_base = "2'-O-methyl corresponding base"
<220> FEATURE:
<221> NAME/KEY: modified_base
<222> LOCATION: 2, 3, 4, 9, 11, 12, 14, 15, 16
<223> OTHER INFORMATION: /mod_base = "2'-hydroxy corresponding base"

<400> SEQUENCE: 33
caaguucuau ggugagcuct t                                              21

<210> SEQ ID NO 34
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 6, 9, 11
<223> OTHER INFORMATION: /mod_base = "2'-O-methyl corresponding base"
<220> FEATURE:
<221> NAME/KEY: modified_base
<222> LOCATION: 1, 2, 3, 4, 5, 7, 8, 10, 12, 13, 14, 15, 16, 17, 18, 19
<223> OTHER INFORMATION: /mod_base = "2'-hydroxy corresponding base"

<400> SEQUENCE: 34
gagcucacca uagaacuugt t                                              21

<210> SEQ ID NO 35
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 4, 7, 9, 11, 13, 14, 18
<223> OTHER INFORMATION: /mod_base = "2'-O-methyl corresponding base"
<220> FEATURE:
<221> NAME/KEY: modified_base
<222> LOCATION: 3, 5, 6, 8, 10, 12, 15, 16, 17, 19
<223> OTHER INFORMATION: /mod_base = "2'-hydroxy corresponding base"
```

<400> SEQUENCE: 35
cuacagcaca caccggacat t          21

<210> SEQ ID NO 36
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 17
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 7, 8, 9, 10, 11, 12, 13, 14, 15, 16,
      18, 19
<223> OTHER INFORMATION: /mod_base = "2'-hydroxy corresponding base"

<400> SEQUENCE: 36
uguccggugu gugcuguagt t          21

<210> SEQ ID NO 37
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 5, 6, 7, 9, 12, 16, 17, 18, 19
<223> OTHER INFORMATION: /mod_base = "2'-O-methyl corresponding base"
<220> FEATURE:
<221> NAME/KEY: modified_base
<222> LOCATION: 1, 2, 3, 8, 10, 11, 13, 14, 15
<223> OTHER INFORMATION: /mod_base = "2'-hydroxy corresponding base"

<400> SEQUENCE: 37
aaguucuaug gugagcucct t          21

<210> SEQ ID NO 38
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 7, 10, 12
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 8, 9, 11, 13, 14, 15, 16, 17, 18, 19
<223> OTHER INFORMATION: /mod_base = "2'-hydroxy corresponding base"

<400> SEQUENCE: 38
ggagcucacc auagaacuut t          21

<210> SEQ ID NO 39
<211> LENGTH: 21
<212> TYPE: DNA

```
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 6, 7, 8, 12, 16, 17, 18
<223> OTHER INFORMATION: /mod_base = "2'-O-methyl corresponding base"
<220> FEATURE:
<221> NAME/KEY: modified_base
<222> LOCATION: 5, 9, 10, 11, 13, 14, 15, 19
<223> OTHER INFORMATION: /mod_base = "2'-hydroxy corresponding base"

<400> SEQUENCE: 39
uuuugucuaa augaguucat t                                              21

<210> SEQ ID NO 40
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 7, 11, 15
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 8, 9, 10, 12, 13, 14, 16, 17, 18, 19
<223> OTHER INFORMATION: /mod_base = "2'-hydroxy corresponding base"

<400> SEQUENCE: 40
ugaacucauu uagacaaaat t                                              21

<210> SEQ ID NO 41
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 5, 6, 8, 9, 11, 12, 13, 14, 16, 17, 18, 19
<223> OTHER INFORMATION: /mod_base = "2'-O-methyl corresponding base"
<220> FEATURE:
<221> NAME/KEY: modified_base
<222> LOCATION: 7, 10, 15
<223> OTHER INFORMATION: /mod_base = "2'-hydroxy corresponding base"

<400> SEQUENCE: 41
ccucucacug uuccgccuct t                                              21

<210> SEQ ID NO 42
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 10
<223> OTHER INFORMATION: /mod_base = "2'-O-methyl corresponding base"
```

-continued

```
<220> FEATURE:
<221> NAME/KEY: modified_base
<222> LOCATION: 1, 2, 3, 4, 5, 6, 7, 8, 9, 11, 12, 13, 14, 15, 16, 17,
      18, 19
<223> OTHER INFORMATION: /mod_base = "2'-hydroxy corresponding base"

<400> SEQUENCE: 42
gaggcggaac agugagaggt t                                              21

<210> SEQ ID NO 43
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 4, 7, 8, 9, 10, 11, 12, 14, 17, 18
<223> OTHER INFORMATION: /mod_base = "2'-O-methyl corresponding base"
<220> FEATURE:
<221> NAME/KEY: modified_base
<222> LOCATION: 1, 2, 5, 6, 13, 15, 16, 19
<223> OTHER INFORMATION: /mod_base = "2'-hydroxy corresponding base"

<400> SEQUENCE: 43
aaccaguucu uuguggccgt t                                              21

<210> SEQ ID NO 44
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 7
<223> OTHER INFORMATION: /mod_base = "2'-O-methyl corresponding base"
<220> FEATURE:
<221> NAME/KEY: modified_base
<222> LOCATION: 1, 2, 3, 4, 6, 8, 9, 10, 11, 12, 13, 14, 15, 16, 17, 18,
      19
<223> OTHER INFORMATION: /mod_base = "2'-hydroxy corresponding base"

<400> SEQUENCE: 44
cggccacaaa gaacugguut t                                              21

<210> SEQ ID NO 45
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 5, 6, 8, 9, 10, 11, 13, 14, 15, 16, 18
<223> OTHER INFORMATION: /mod_base = "2'-O-methyl corresponding base"
<220> FEATURE:
<221> NAME/KEY: modified_base
<222> LOCATION: 4, 7, 12, 17, 19
<223> OTHER INFORMATION: /mod_base = "2'-hydroxy corresponding base"

<400> SEQUENCE: 45
cucacuguuc cgccucaugt t                                              21
```

<210> SEQ ID NO 46
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 13
<223> OTHER INFORMATION: /mod_base = "2'-O-methyl corresponding base"
<220> FEATURE:
<221> NAME/KEY: modified_base
<222> LOCATION: 2, 3, 4, 5, 6, 7, 8, 9, 10, 11, 12, 14, 15, 16, 17, 18,
      19
<223> OTHER INFORMATION: /mod_base = "2'-hydroxy corresponding base"

<400> SEQUENCE: 46
caugaggcgg aacagugagt t                                        21

<210> SEQ ID NO 47
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 6, 7, 8, 9, 11, 14, 18, 19
<223> OTHER INFORMATION: /mod_base = "2'-O-methyl corresponding base"
<220> FEATURE:
<221> NAME/KEY: modified_base
<222> LOCATION: 3, 4, 5, 10, 12, 13, 15, 16, 17
<223> OTHER INFORMATION: /mod_base = "2'-hydroxy corresponding base"

<400> SEQUENCE: 47
ccaaguucua uggugagcut t                                        21

<210> SEQ ID NO 48
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 5, 8, 10
<223> OTHER INFORMATION: /mod_base = "2'-O-methyl corresponding base"
<220> FEATURE:
<221> NAME/KEY: modified_base
<222> LOCATION: 1, 2, 3, 4, 6, 7, 9, 11, 12, 13, 14, 15, 16, 17, 18, 19
<223> OTHER INFORMATION: /mod_base = "2'-hydroxy corresponding base"

<400> SEQUENCE: 48
agcucaccau agaacuuggt t                                        21

<210> SEQ ID NO 49
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:

-continued

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 5, 6, 7, 8, 9, 11, 14, 15, 17, 18, 19
<223> OTHER INFORMATION: /mod_base = "2'-O-methyl corresponding base"
<220> FEATURE:
<221> NAME/KEY: modified_base
<222> LOCATION: 2, 3, 10, 12, 13, 16
<223> OTHER INFORMATION: /mod_base = "2'-hydroxy corresponding base"

<400> SEQUENCE: 49
caguucuuug uggccgucut t                                              21

<210> SEQ ID NO 50
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 8, 10
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 7, 9, 11, 12, 13, 14, 15, 16, 17, 18,
      19
<223> OTHER INFORMATION: /mod_base = "2'-hydroxy corresponding base"

<400> SEQUENCE: 50
agacggccac aaagaacugt t                                              21

<210> SEQ ID NO 51
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 4, 7, 11, 13, 15
<223> OTHER INFORMATION: /mod_base = "2'-O-methyl corresponding base"
<220> FEATURE:
<221> NAME/KEY: modified_base
<222> LOCATION: 1, 2, 5, 6, 8, 9, 10, 12, 14, 16, 17, 18, 19
<223> OTHER INFORMATION: /mod_base = "2'-hydroxy corresponding base"

<400> SEQUENCE: 51
ggcuggcagg ugcgcaagat t                                              21

<210> SEQ ID NO 52
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 8, 15
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 7, 9, 10, 11, 12, 13, 14, 16, 17, 18,
```

-continued

19
<223> OTHER INFORMATION: /mod_base = "2'-hydroxy corresponding base"

<400> SEQUENCE: 52
ucuugcgcac cugccagcct t                                              21

<210> SEQ ID NO 53
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 5, 6, 7, 13, 16, 18
<223> OTHER INFORMATION: /mod_base = "2'-O-methyl corresponding base"
<220> FEATURE:
<221> NAME/KEY: modified_base
<222> LOCATION: 8, 9, 10, 11, 12, 14, 15, 17, 19
<223> OTHER INFORMATION: /mod_base = "2'-hydroxy corresponding base"

<400> SEQUENCE: 53
cuccucugag ggcagcacgt t                                              21

<210> SEQ ID NO 54
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 12
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 7, 8, 9, 10, 11, 13, 14, 15, 16, 17,
      18, 19
<223> OTHER INFORMATION: /mod_base = "2'-hydroxy corresponding base"

<400> SEQUENCE: 54
cgugcugccc ucagaggagt t                                              21

<210> SEQ ID NO 55
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 3, 4, 5, 6, 8, 9, 11, 12, 14, 15, 16, 18
<223> OTHER INFORMATION: /mod_base = "2'-O-methyl corresponding base"
<220> FEATURE:
<221> NAME/KEY: modified_base
<222> LOCATION: 1, 7, 10, 13, 17, 19
<223> OTHER INFORMATION: /mod_base = "2'-hydroxy corresponding base"

<400> SEQUENCE: 55
gucuucacug ucauuuacat t                                              21

<210> SEQ ID NO 56

```
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 10
<223> OTHER INFORMATION: /mod_base = "2'-O-methyl corresponding base"
<220> FEATURE:
<221> NAME/KEY: modified_base
<222> LOCATION: 1, 2, 4, 5, 6, 7, 8, 9, 11, 12, 13, 14, 15, 16, 17, 18,
      19
<223> OTHER INFORMATION: /mod_base = "2'-hydroxy corresponding base"

<400> SEQUENCE: 56
uguaaaugac agugaagact t                                              21

<210> SEQ ID NO 57
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 4, 5, 8, 10, 15, 17, 18, 19
<223> OTHER INFORMATION: /mod_base = "2'-O-methyl corresponding base"
<220> FEATURE:
<221> NAME/KEY: modified_base
<222> LOCATION: 2, 3, 6, 7, 9, 11, 12, 13, 14, 16
<223> OTHER INFORMATION: /mod_base = "2'-hydroxy corresponding base"

<400> SEQUENCE: 57
caaccagcgc aggaugucut t                                              21

<210> SEQ ID NO 58
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4
<223> OTHER INFORMATION: /mod_base = "2'-O-methyl corresponding base"
<220> FEATURE:
<221> NAME/KEY: modified_base
<222> LOCATION: 1, 2, 3, 5, 6, 7, 8, 9, 10, 11, 12, 13, 14, 15, 16, 17,
      18, 19
<223> OTHER INFORMATION: /mod_base = "2'-hydroxy corresponding base"

<400> SEQUENCE: 58
agacauccug cgcugguugt t                                              21

<210> SEQ ID NO 59
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 6, 8, 9, 10, 13, 14, 15
<223> OTHER INFORMATION: /mod_base = "2'-O-methyl corresponding base"
<220> FEATURE:
<221> NAME/KEY: modified_base
<222> LOCATION: 1, 2, 3, 4, 5, 7, 11, 12, 16, 17, 18, 19
<223> OTHER INFORMATION: /mod_base = "2'-hydroxy corresponding base"

<400> SEQUENCE: 59
agaaguaucu gaucugggat t                                              21

<210> SEQ ID NO 60
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 9, 13
<223> OTHER INFORMATION: /mod_base = "2'-O-methyl corresponding base"
<220> FEATURE:
<221> NAME/KEY: modified_base
<222> LOCATION: 1, 2, 3, 5, 6, 7, 8, 10, 11, 12, 14, 15, 16, 17, 18, 19
<223> OTHER INFORMATION: /mod_base = "2'-hydroxy corresponding base"

<400> SEQUENCE: 60
ucccagauca gauacuucut t                                              21

<210> SEQ ID NO 61
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 5, 8, 10, 12, 14, 15, 19
<223> OTHER INFORMATION: /mod_base = "2'-O-methyl corresponding base"
<220> FEATURE:
<221> NAME/KEY: modified_base
<222> LOCATION: 4, 6, 7, 9, 11, 13, 16, 17, 18
<223> OTHER INFORMATION: /mod_base = "2'-hydroxy corresponding base"

<400> SEQUENCE: 61
ucuacagcac acaccggact t                                              21

<210> SEQ ID NO 62
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 16
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 7, 8, 9, 10, 11, 12, 13, 14, 15, 17,
       18, 19
<223> OTHER INFORMATION: /mod_base = "2'-hydroxy corresponding base"
```

-continued

```
<400> SEQUENCE: 62
guccggugug ugcuguagat t                                              21

<210> SEQ ID NO 63
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 4, 5, 6, 8, 11, 15, 16, 17, 18, 19
<223> OTHER INFORMATION: /mod_base = "2'-O-methyl corresponding base"
<220> FEATURE:
<221> NAME/KEY: modified_base
<222> LOCATION: 1, 2, 7, 9, 10, 12, 13, 14
<223> OTHER INFORMATION: /mod_base = "2'-hydroxy corresponding base"

<400> SEQUENCE: 63
aguucuaugg ugagcuccct t                                              21

<210> SEQ ID NO 64
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 8, 11, 13
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 7, 9, 10, 12, 14, 15, 16, 17, 18, 19
<223> OTHER INFORMATION: /mod_base = "2'-hydroxy corresponding base"

<400> SEQUENCE: 64
gggagcucac cauagaacut t                                              21

<210> SEQ ID NO 65
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 5, 8, 12, 13, 14, 15, 16, 19
<223> OTHER INFORMATION: /mod_base = "2'-O-methyl corresponding base"
<220> FEATURE:
<221> NAME/KEY: modified_base
<222> LOCATION: 4, 6, 7, 9, 10, 11, 17, 18
<223> OTHER INFORMATION: /mod_base = "2'-hydroxy corresponding base"

<400> SEQUENCE: 65
ucuaugguga gcucccagct t                                              21

<210> SEQ ID NO 66
<211> LENGTH: 21
<212> TYPE: DNA
<213> ORGANISM: Artificial sequence
<220> FEATURE:
```

<223> OTHER INFORMATION: siRNAs specific for Nav1.8
<220> FEATURE:
<223> OTHER INFORMATION: 5'-terminal nucleic acid is a nucleoside, i.e. base + sugar but lacking 5'-phosphate
<220> FEATURE:
<221> NAME/KEY: modified_base
<222> LOCATION: 11, 14, 16
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 7, 8, 9, 10, 12, 13, 15, 17, 18, 19
<223> OTHER INFORMATION: /mod_base = "2'-hydroxy corresponding base"

<400> SEQUENCE: 66
gcugggagcu caccauagat t                          21

<210> SEQ ID NO 67
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e. base + sugar but lacking 5'-phosphate
<220> FEATURE:
<221> NAME/KEY: modified_base
<222> LOCATION: 3, 4, 5, 6, 7, 8, 10, 13, 14, 16, 17, 18, 19
<223> OTHER INFORMATION: /mod_base = "2'-O-methyl corresponding base"
<220> FEATURE:
<221> NAME/KEY: modified_base
<222> LOCATION: 1, 2, 9, 11, 12, 15
<223> OTHER INFORMATION: /mod_base = "2'-hydroxy corresponding base"

<400> SEQUENCE: 67
aguucuuugu ggccgucuut t                          21

<210> SEQ ID NO 68
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e. base + sugar but lacking 5'-phosphate
<220> FEATURE:
<221> NAME/KEY: modified_base
<222> LOCATION: 9, 11
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 7, 8, 10, 12, 13, 14, 15, 16, 17, 18, 19
<223> OTHER INFORMATION: /mod_base = "2'-hydroxy corresponding base"

<400> SEQUENCE: 68
aagacggcca caaagaacut t                          21

<210> SEQ ID NO 69
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e. base + sugar but lacking 5'-phosphate
<220> FEATURE:
<221> NAME/KEY: modified_base
<222> LOCATION: 1, 2, 4, 5, 7, 8, 9, 10, 12, 13, 14, 15, 17
<223> OTHER INFORMATION: /mod_base = "2'-O-methyl corresponding base"
<220> FEATURE:

```
<221> NAME/KEY: modified_base
<222> LOCATION: 3, 6, 11, 16, 18, 19
<223> OTHER INFORMATION: /mod_base = "2'-hydroxy corresponding base"

<400> SEQUENCE: 69
ucacuguucc gccucaugat t                                              21

<210> SEQ ID NO 70
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 2, 14
<223> OTHER INFORMATION: /mod_base = "2'-O-methyl corresponding base"
<220> FEATURE:
<221> NAME/KEY: modified_base
<222> LOCATION: 1, 3, 4, 5, 6, 7, 8, 9, 10, 11, 12, 13, 15, 16, 17, 18,
      19
<223> OTHER INFORMATION: /mod_base = "2'-hydroxy corresponding base"

<400> SEQUENCE: 70
ucaugaggcg aacagugat t                                               21

<210> SEQ ID NO 71
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 4, 5, 6, 7, 10, 11, 13, 15, 16, 19
<223> OTHER INFORMATION: /mod_base = "2'-O-methyl corresponding base"
<220> FEATURE:
<221> NAME/KEY: modified_base
<222> LOCATION: 1, 2, 3, 8, 9, 12, 14, 17, 18
<223> OTHER INFORMATION: /mod_base = "2'-hydroxy corresponding base"

<400> SEQUENCE: 71
ggauuuuaac uacaccagct t                                              21

<210> SEQ ID NO 72
<211> LENGTH: 21
<212> TYPE: DNA
<213> ORGANISM: Artificial sequence
<220> FEATURE:
<223> OTHER INFORMATION: siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 8, 12
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 7, 9, 10, 11, 13, 14, 15, 16, 17, 18,
      19
<223> OTHER INFORMATION: /mod_base = "2'-hydroxy corresponding base"

<400> SEQUENCE: 72
gcugguguag uuaaaaucct t                                              21
```

<210> SEQ ID NO 73
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 73
ccgcuugcug cgcguauuct t                                              21

<210> SEQ ID NO 74
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 74
gaauacgcgc agcaagcggt t                                              21

<210> SEQ ID NO 75
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 75
cuugcuaccg uaucguggat t                                              21

<210> SEQ ID NO 76
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 76
uccacgauac gguagcaagt t                                              21

<210> SEQ ID NO 77
<211> LENGTH: 21

```
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 77
gacuucaucg cuaauccgat t                                              21

<210> SEQ ID NO 78
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 78
ucggauuagc gaugaaguct t                                              21

<210> SEQ ID NO 79
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 79
uggauuuuag cgucauuact t                                              21

<210> SEQ ID NO 80
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 80
guaaugacgc uaaaauccat t                                              21

<210> SEQ ID NO 81
<211> LENGTH: 21
<212> TYPE: DNA
<213> ORGANISM: Artificial sequence
<220> FEATURE:
```

```
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 81
cgcuugcugc gcguauucat t                                              21

<210> SEQ ID NO 82
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 82
ugaauacgcg cagcaagcgt t                                              21

<210> SEQ ID NO 83
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 83
caacuuccgu cgcuuuacut t                                              21

<210> SEQ ID NO 84
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 84
aguaaagcga cggaaguugt t                                              21

<210> SEQ ID NO 85
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
``` base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 85
gucgcuuuac uccggaguct t                                              21

<210> SEQ ID NO 86
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 86
gacuccggag uaaagcgact t                                              21

<210> SEQ ID NO 87
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 87
aaugaguuca cguaccugat t                                              21

<210> SEQ ID NO 88
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 88
ucagguacgu gaacucauut t                                              21

<210> SEQ ID NO 89
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base

```
<222> LOCATION: 1..19
<223> OTHER INFORMATION: /mod_base = "2'-hydroxy corresponding base"

<400> SEQUENCE: 89
agacuugcua ccguaucgut t                                              21

<210> SEQ ID NO 90
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 90
acgauacggu agcaagucut t                                              21

<210> SEQ ID NO 91
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 91
aguuuauuua uuacggucat t                                              21

<210> SEQ ID NO 92
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 92
ugaccguaau aaauaaacut t                                              21

<210> SEQ ID NO 93
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

-continued

```
<400> SEQUENCE: 93
aaaugaguuc acguaccugt t                                              21

<210> SEQ ID NO 94
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 94
cagguacgug aacucauuut t                                              21

<210> SEQ ID NO 95
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 95
ugucucggca uucgaugcat t                                              21

<210> SEQ ID NO 96
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 96
ugcaucgaau gccgagacat t                                              21

<210> SEQ ID NO 97
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 97
ucaaagcccu ucgaacccut t                                              21
```

-continued

<210> SEQ ID NO 98
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 98
aggguucgaa gggcuuugat t                                              21

<210> SEQ ID NO 99
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 99
gcgggcucuu ucucgauuut t                                              21

<210> SEQ ID NO 100
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 100
aaaucgagaa agagcccgct t                                              21

<210> SEQ ID NO 101
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 101
ccuuguaccu uugucgauut t                                              21

<210> SEQ ID NO 102

```
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 102
aaucgacaaa gguacaaggt t                                              21

<210> SEQ ID NO 103
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 103
gugguucucu ccauugcgat t                                              21

<210> SEQ ID NO 104
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 104
ucgcaaugga gagaaccact t                                              21

<210> SEQ ID NO 105
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 105
caaaaggccu aucggagcut t                                              21

<210> SEQ ID NO 106
<211> LENGTH: 21
<212> TYPE: DNA
<213> ORGANISM: Artificial sequence
```

```
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 106
agcuccgaua ggccuuuugt t                                              21

<210> SEQ ID NO 107
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 107
aaaggccuau cggagcuaut t                                              21

<210> SEQ ID NO 108
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 108
auagcuccga uaggccuuut t                                              21

<210> SEQ ID NO 109
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 109
ggugcaucaa cuauaccgat t                                              21

<210> SEQ ID NO 110
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
```

<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 110
ucgguauagu ugaugcacct t                                              21

<210> SEQ ID NO 111
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 111
aacuaccgua acaaccgaat t                                              21

<210> SEQ ID NO 112
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 112
uucgguuguu acguaguut t                                               21

<210> SEQ ID NO 113
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 113
ucgcuuuacu ccggagucat t                                              21

<210> SEQ ID NO 114
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:

```
<221> NAME/KEY: modified_base
<222> LOCATION: 1..19
<223> OTHER INFORMATION: /mod_base = "2'-hydroxy corresponding base"

<400> SEQUENCE: 114
ugacuccgga guaaagcgat t                                              21

<210> SEQ ID NO 115
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 115
gaaaacgccg ggcuagucat t                                              21

<210> SEQ ID NO 116
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 116
ugacuagccc ggcguuuuct t                                              21

<210> SEQ ID NO 117
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 117
accgaaaaaa uaucuccgct t                                              21

<210> SEQ ID NO 118
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 118
gcggagauau uuuuucggut t                                              21

<210> SEQ ID NO 119
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 119
uucaucgcua auccgacugt t                                              21

<210> SEQ ID NO 120
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 120
cagucggauu agcgaugaat t                                              21

<210> SEQ ID NO 121
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 121
uccgucgcuu uacuccggat t                                              21

<210> SEQ ID NO 122
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 122
```
uccggaguaa agcgacggat t				21

<210> SEQ ID NO 123
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 123
gcuuuacucc ggagucacut t				21

<210> SEQ ID NO 124
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 124
agugacuccg gaguaaagct t				21

<210> SEQ ID NO 125
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 125
ggaaaacgcc gggcuaguct t				21

<210> SEQ ID NO 126
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 126
gacuagcccg gcguuuucct t				21

```
<210> SEQ ID NO 127
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 127
acuaccguaa caaccgaaat t                                              21

<210> SEQ ID NO 128
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 128
uuucgguugu uacgguagut t                                              21

<210> SEQ ID NO 129
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 129
uggccaucgu accaaacagt t                                              21

<210> SEQ ID NO 130
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 130
cuguuuggua cgauggccat t                                              21

<210> SEQ ID NO 131
<211> LENGTH: 21
<212> TYPE: DNA
```

```
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 131
acuugcuacc guaucguggt t                                                  21

<210> SEQ ID NO 132
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 132
ccacgauacg guagcaagut t                                                  21

<210> SEQ ID NO 133
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 133
gauaagucuc acagcgaagt t                                                  21

<210> SEQ ID NO 134
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 134
cuucgcugug agacuuauct t                                                  21

<210> SEQ ID NO 135
<211> LENGTH: 21
<212> TYPE: DNA
<213> ORGANISM: Artificial sequence
<220> FEATURE:
<223> OTHER INFORMATION: Further siRNAs specific for Nav1.8
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 135
auaagucuca cagcgaagat t                                              21

<210> SEQ ID NO 136
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 136
ucuucgcugu gagacuuaut t                                              21

<210> SEQ ID NO 137
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 137
aagcccuucg aacccuucgt t                                              21

<210> SEQ ID NO 138
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 138
cgaaggguuc gaagggcuut t                                              21

<210> SEQ ID NO 139
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 139
agcccuucga acccuucgct t                                              21

<210> SEQ ID NO 140
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 140
gcgaaggguu cgaagggcut t                                              21

<210> SEQ ID NO 141
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 141
cccuucgaac ccuucgcgct t                                              21

<210> SEQ ID NO 142
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 142
gcgcgaaggg uucgaagggt t                                              21

<210> SEQ ID NO 143
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

```
<223> OTHER INFORMATION: /mod_base = "2'-hydroxy corresponding base"

<400> SEQUENCE: 143
aacccaaucg aaauauacut t                                              21

<210> SEQ ID NO 144
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 144
aguauauuuc gauuggguut t                                              21

<210> SEQ ID NO 145
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 145
cgcuuuacuc cggagucact t                                              21

<210> SEQ ID NO 146
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 146
gugacuccgg aguaaagcgt t                                              21

<210> SEQ ID NO 147
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 147
```
gaccauuucc cgguuuagut t                                              21

<210> SEQ ID NO 148
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 148
acuaaaccgg gaaaugguct t                                              21

<210> SEQ ID NO 149
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 149
cgguuuagug ccacucgggt t                                              21

<210> SEQ ID NO 150
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 150
cccgaguggc acuaaaccgt t                                              21

<210> SEQ ID NO 151
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 151
cacagcaaua gaucuccgut t                                              21

```
<210> SEQ ID NO 152
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 152
acggagaucu auugcugugt t                                              21

<210> SEQ ID NO 153
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 153
acuagggauu gacacaacct t                                              21

<210> SEQ ID NO 154
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 154
gguuguguca aucccuagut t                                              21

<210> SEQ ID NO 155
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 155
cccacaaugg aucaccuuut t                                              21

<210> SEQ ID NO 156
<211> LENGTH: 21
```

```
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 156
aaaggugauc cauugugggt t                                              21

<210> SEQ ID NO 157
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 157
ugucuuuucu aggccucgct t                                              21

<210> SEQ ID NO 158
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 158
gcgaggccua gaaaagacat t                                              21

<210> SEQ ID NO 159
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 159
agcugucgau gucucggcat t                                              21

<210> SEQ ID NO 160
<211> LENGTH: 21
<212> TYPE: DNA
<213> ORGANISM: Artificial sequence
<220> FEATURE:
```

-continued

<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 160
ugccgagaca ucgacagcut t                                              21

<210> SEQ ID NO 161
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 161
gucucggcau ucgaugcagt t                                              21

<210> SEQ ID NO 162
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 162
cugcaucgaa ugccgagact t                                              21

<210> SEQ ID NO 163
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 163
ucaaaaucau ugccuucgat t                                              21

<210> SEQ ID NO 164
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.

-continued

```
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 164
ucgaaggcaa ugauuuugat t                                             21

<210> SEQ ID NO 165
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 165
cccgcuggca caugcacgat t                                             21

<210> SEQ ID NO 166
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 166
ucgugcaugu gccagcgggt t                                             21

<210> SEQ ID NO 167
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 167
ucauugucuu ccguauccut t                                             21

<210> SEQ ID NO 168
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
```

-continued

```
<222> LOCATION: 1..19
<223> OTHER INFORMATION: /mod_base = "2'-hydroxy corresponding base"

<400> SEQUENCE: 168
aggauacgga agacaaugat t                                              21

<210> SEQ ID NO 169
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 169
uuggccaucg uaccaaacat t                                              21

<210> SEQ ID NO 170
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 170
uguuugguac gauggccaat t                                              21

<210> SEQ ID NO 171
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 171
gcacggugga cugccuagat t                                              21

<210> SEQ ID NO 172
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 172
ucuaggcagu ccaccgugct t                                              21

<210> SEQ ID NO 173
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 173
gcccuucgaa cccuucgcgt t                                              21

<210> SEQ ID NO 174
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 174
cgcgaagggu ucgaagggct t                                              21

<210> SEQ ID NO 175
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 175
ugcgggcucu uucucgauut t                                              21

<210> SEQ ID NO 176
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 176
aaucgagaaa gagcccgcat t                                              21
```

```
<210> SEQ ID NO 177
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 177
gaggugcauc aacuauacct t                                              21

<210> SEQ ID NO 178
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 178
gguauaguug augcaccuct t                                              21

<210> SEQ ID NO 179
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 179
caucaacuau accgauggat t                                              21

<210> SEQ ID NO 180
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 180
uccaucggua uaguugaugt t                                              21

<210> SEQ ID NO 181
```

```
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 181
aaaucauccu augaaccaat t                                              21

<210> SEQ ID NO 182
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 182
uugguucaua ggaugauuut t                                              21

<210> SEQ ID NO 183
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 183
aaggccuauc ggagcuaugt t                                              21

<210> SEQ ID NO 184
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 184
cauagcuccg auaggccuut t                                              21

<210> SEQ ID NO 185
<211> LENGTH: 21
<212> TYPE: DNA
<213> ORGANISM: Artificial sequence
```

```
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 185
uguacuccca gacaaaucut t                                                   21

<210> SEQ ID NO 186
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 186
agauuugucu gggaguacat t                                                   21

<210> SEQ ID NO 187
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 187
aggacaucua gcucaauact t                                                   21

<210> SEQ ID NO 188
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 188
guauugagcu agauguccut t                                                   21

<210> SEQ ID NO 189
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
```

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 189 ccguuuagu gccacucggt t                                                 21

<210> SEQ ID NO 190
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 190
ccgaguggca cuaaaccggt t                                                21

<210> SEQ ID NO 191
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 191
caucgcuaau ccgacugugt t                                                21

<210> SEQ ID NO 192
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 192
cacagucgga uuagcgaugt t                                                21

<210> SEQ ID NO 193
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
```

<221> NAME/KEY: modified_base
<222> LOCATION: 1..19
<223> OTHER INFORMATION: /mod_base = "2'-hydroxy corresponding base"

<400> SEQUENCE: 193
aaacuaccgu aacaaccgat t                                               21

<210> SEQ ID NO 194
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 194
ucgguuguua cgguaguuut t                                               21

<210> SEQ ID NO 195
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 195
aucgcuaauc cgacugugut t                                               21

<210> SEQ ID NO 196
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 196
acacagucgg auuagcgaut t                                               21

<210> SEQ ID NO 197
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 197
cccgguuuag ugccacucgt t                                              21

<210> SEQ ID NO 198
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 198
cgaguggcac uaaaccgggt t                                              21

<210> SEQ ID NO 199
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 199
uuuagcguca uuacccuggt t                                              21

<210> SEQ ID NO 200
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 200
ccaggguaau gacgcuaaat t                                              21

<210> SEQ ID NO 201
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 201
aauaagcgag gcacuucugt t	21

<210> SEQ ID NO 202
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 202
cagaagugcc ucgcuuauut t	21

<210> SEQ ID NO 203
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 203
cuaccguaac aaccgaaaat t	21

<210> SEQ ID NO 204
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 204
uuuucgguug uuacgguagt t	21

<210> SEQ ID NO 205
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 205
ucgcuaaucc gacugugugt t	21

```
<210> SEQ ID NO 206
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 206
cacacagucg gauuagcgat t                                               21

<210> SEQ ID NO 207
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 207
ucccucgaaa cuacaacut t                                                21

<210> SEQ ID NO 208
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 208
aguuguuagu uucgagggat t                                               21

<210> SEQ ID NO 209
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 209
cuuccgucgc uuuacuccgt t                                               21

<210> SEQ ID NO 210
<211> LENGTH: 21
<212> TYPE: DNA
```

-continued

```
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 210
cggaguaaag cgacggaagt t                                              21

<210> SEQ ID NO 211
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 211
uuucccgguu uagugccact t                                              21

<210> SEQ ID NO 212
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 212
guggcacuaa accgggaaat t                                              21

<210> SEQ ID NO 213
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 213
gguuuagugc cacucgggct t                                              21

<210> SEQ ID NO 214
<211> LENGTH: 21
<212> TYPE: DNA
<213> ORGANISM: Artificial sequence
<220> FEATURE:
<223> OTHER INFORMATION: Further siRNAs specific for Nav1.8
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 214
gcccgagugg cacuaaacct t                                              21

<210> SEQ ID NO 215
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 215
acaacccgga uuuaacuat t                                               21

<210> SEQ ID NO 216
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 216
uaguuaaaau ccggguugut t                                              21

<210> SEQ ID NO 217
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 217
cuagggauug acacaaccut t                                              21

<210> SEQ ID NO 218
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 218
agguuguguc aaucccuagt t                                                    21

<210> SEQ ID NO 219
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 219
ugucgauugu gaauaacaat t                                                    21

<210> SEQ ID NO 220
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 220
uuguuauuca caaucgacat t                                                    21

<210> SEQ ID NO 221
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 221
caucgugacc agacaagcut t                                                    21

<210> SEQ ID NO 222
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

```
<223> OTHER INFORMATION: /mod_base = "2'-hydroxy corresponding base"

<400> SEQUENCE: 222
agcuugucug gucacgaugt t                                               21

<210> SEQ ID NO 223
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 223
ccuaucggag cuaugugcut t                                               21

<210> SEQ ID NO 224
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 224
agcacauagc uccgauaggt t                                               21

<210> SEQ ID NO 225
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 225
uuagcgucau uacccuggct t                                               21

<210> SEQ ID NO 226
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 226
```

```
gccaggguaa ugacgcuaat t                                              21

<210> SEQ ID NO 227
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 227
agcaauagau cuccgugggt t                                              21

<210> SEQ ID NO 228
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 228
cccacggaga ucuauugcut t                                              21

<210> SEQ ID NO 229
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 229
aucgaaauau acugauccat t                                              21

<210> SEQ ID NO 230
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 230
uggaucagua uauuucgaut t                                              21
```

```
<210> SEQ ID NO 231
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 231
ggaucccucg aaacuaacat t                                             21

<210> SEQ ID NO 232
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 232
uguuaguuuc gagggaucct t                                             21

<210> SEQ ID NO 233
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 233
acaccggaca uuuauggugt t                                             21

<210> SEQ ID NO 234
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 234
caccauaaau guccggugut t                                             21

<210> SEQ ID NO 235
<211> LENGTH: 21
```

```
<210> SEQ ID NO 235
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 235
guuuagugcc acucgggcct t                                              21

<210> SEQ ID NO 236
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 236
ggcccgagug gcacuaaact t                                              21

<210> SEQ ID NO 237
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 237
augacccgaa cugaccuuct t                                              21

<210> SEQ ID NO 238
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 238
gaaggucagu ucgggucaut t                                              21

<210> SEQ ID NO 239
<211> LENGTH: 21
<212> TYPE: DNA
<213> ORGANISM: Artificial sequence
<220> FEATURE:
```

```
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 239
auuuuagcgu cauuacccut t                                              21

<210> SEQ ID NO 240
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 240
aggguaauga cgcuaaaaut t                                              21

<210> SEQ ID NO 241
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 241
uuuuagcguc auuacccugt t                                              21

<210> SEQ ID NO 242
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 242
caggguaaug acgcuaaaat t                                              21

<210> SEQ ID NO 243
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
```

```
        base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 243
gcaauagauc uccgugggat t                                             21

<210> SEQ ID NO 244
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
        base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 244
ucccacggag aucuauugct t                                             21

<210> SEQ ID NO 245
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
        base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 245
aaauaagcga ggcacuucut t                                             21

<210> SEQ ID NO 246
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
        base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 246
agaagugccu cgcuuauuut t                                             21

<210> SEQ ID NO 247
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
        base + sugar but lacking 5'-phosphate
<220> FEATURE:
<221> NAME/KEY: modified_base
```

```
<222> LOCATION: 1..19
<223> OTHER INFORMATION: /mod_base = "2'-hydroxy corresponding base"

<400> SEQUENCE: 247
auaagcgagg cacuucugat t                                              21

<210> SEQ ID NO 248
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 248
ucagaagugc cucgcuuaut t                                              21

<210> SEQ ID NO 249
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 249
ugauccuuac aaccagcgct t                                              21

<210> SEQ ID NO 250
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 250
gcgcugguug uaaggaucat t                                              21

<210> SEQ ID NO 251
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 251
uggccgagau aucucacuct t                                              21

<210> SEQ ID NO 252
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 252
gagugagaua ucucggccat t                                              21

<210> SEQ ID NO 253
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 253
caaccgccgc ccacuagugt t                                              21

<210> SEQ ID NO 254
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 254
cacuaguggg cggcgguugt t                                              21

<210> SEQ ID NO 255
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 255
uuagaugaac cuuuccgggt t                                              21
```

<210> SEQ ID NO 256
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 256
cccggaaagg uucaucuaat t                                              21

<210> SEQ ID NO 257
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 257 aaccuuccg ggcccaaagt t                                               21

<210> SEQ ID NO 258
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 258 cuugggccc ggaaagguut t                                               21

<210> SEQ ID NO 259
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 259
auaaccuccg uccuugaggt t                                              21

<210> SEQ ID NO 260

```
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 260
ccucaaggac ggagguuaut t                                             21

<210> SEQ ID NO 261
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 261
cuugugacgg aucccuuugt t                                             21

<210> SEQ ID NO 262
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 262
caaagggauc cgucacaagt t                                             21

<210> SEQ ID NO 263
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 263
ccuaccuucg aagccaugct t                                             21

<210> SEQ ID NO 264
<211> LENGTH: 21
<212> TYPE: DNA
<213> ORGANISM: Artificial sequence
```

```
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 264
gcauggcuuc gaagguaggt t                                               21

<210> SEQ ID NO 265
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 265
aaaucauugc cuucgaccct t                                               21

<210> SEQ ID NO 266
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 266
gggucgaagg caaugauuut t                                               21

<210> SEQ ID NO 267
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 267
cauugccuuc gacccauact t                                               21

<210> SEQ ID NO 268
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
```

-continued

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 268 guauggucg aaggcaaugt t                                              21

<210> SEQ ID NO 269
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 269
cuucgaccca uacuauuaut t                                             21

<210> SEQ ID NO 270
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 270
auaauaguau gggucgaagt t                                             21

<210> SEQ ID NO 271
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 271
ucaucgcuaa uccgacugut t                                             21

<210> SEQ ID NO 272
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
```

```
<221> NAME/KEY: modified_base
<222> LOCATION: 1..19
<223> OTHER INFORMATION: /mod_base = "2'-hydroxy corresponding base"

<400> SEQUENCE: 272
acagucggau uagcgaugat t                                              21

<210> SEQ ID NO 273
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 273
aauccgacug ugugggucut t                                              21

<210> SEQ ID NO 274
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 274
agacccacac agucggauut t                                              21

<210> SEQ ID NO 275
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 275
agcacggugg acugccuagt t                                              21

<210> SEQ ID NO 276
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 276
cuaggcaguc caccgugcut t                                              21

<210> SEQ ID NO 277
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 277
ggugcgcaag acuugcuact t                                              21

<210> SEQ ID NO 278
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 278
guagcaaguc uugcgcacct t                                              21

<210> SEQ ID NO 279
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 279
aggugcauca acuauaccgt t                                              21

<210> SEQ ID NO 280
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 280
```

```
cgguauaguu gaugcaccut t                                              21

<210> SEQ ID NO 281
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 281
aucaacuaua ccgauggagt t                                              21

<210> SEQ ID NO 282
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 282
cuccaucggu auaguugaut t                                              21

<210> SEQ ID NO 283
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 283
uugucgauug ugaauaacat t                                              21

<210> SEQ ID NO 284
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 284
uguuauucac aaucgacaat t                                              21
```

-continued

```
<210> SEQ ID NO 285
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 285
aauggguuac cuugcacuut t                                            21

<210> SEQ ID NO 286
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 286
aagugcaagg uaacccauut t                                            21

<210> SEQ ID NO 287
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 287
aggccuaucg gagcuaugut t                                            21

<210> SEQ ID NO 288
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 288
acauagcucc gauaggccut t                                            21

<210> SEQ ID NO 289
<211> LENGTH: 21
<212> TYPE: DNA
```

```
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 289
ggccuaucgg agcuaugugt t                                              21

<210> SEQ ID NO 290
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 290
cacauagcuc cgauaggcct t                                              21

<210> SEQ ID NO 291
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 291
uaucggagcu augugcugct t                                              21

<210> SEQ ID NO 292
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 292
gcagcacaua gcuccgauat t                                              21

<210> SEQ ID NO 293
<211> LENGTH: 21
<212> TYPE: DNA
<213> ORGANISM: Artificial sequence
<220> FEATURE:
<223> OTHER INFORMATION: Further siRNAs specific for Nav1.8
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 293
ccguccuaug agagugucat t                                              21

<210> SEQ ID NO 294
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 294
ugacacucuc auaggacggt t                                              21

<210> SEQ ID NO 295
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 295
ccauuggauc ccucgaaact t                                              21

<210> SEQ ID NO 296
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 296
guuucgaggg auccaauggt t                                              21

<210> SEQ ID NO 297
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 297
cauuggaucc cucgaaacut t                                              21

<210> SEQ ID NO 298
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 298
aguuucgagg gauccaaugt t                                              21

<210> SEQ ID NO 299
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 299
aucccucgaa acuaacaact t                                              21

<210> SEQ ID NO 300
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 300
guuguuaguu ucgagggaut t                                              21

<210> SEQ ID NO 301
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

```
<223> OTHER INFORMATION: /mod_base = "2'-hydroxy corresponding base"

<400> SEQUENCE: 301
gaaacuaaca acuuccguct t                                              21

<210> SEQ ID NO 302
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 302
gacggaaguu guuaguuuct t                                              21

<210> SEQ ID NO 303
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 303
uuccgucgcu uuacuccggt t                                              21

<210> SEQ ID NO 304
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 304
ccggaguaaa gcgacggaat t                                              21

<210> SEQ ID NO 305
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 305
```

```
ccgucgcuuu acuccggagt t                                              21

<210> SEQ ID NO 306
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 306
cuccggagua aagcgacggt t                                              21

<210> SEQ ID NO 307
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 307
ggaucuagau ccguucuact t                                              21

<210> SEQ ID NO 308
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 308
guagaacgga ucuagaucct t                                              21

<210> SEQ ID NO 309
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 309
cacacaccgg acauuuaugt t                                              21
```

```
<210> SEQ ID NO 310
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 310
cauaaauguc cggugugugt t                                               21

<210> SEQ ID NO 311
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 311
cacaccggac auuuauggut t                                               21

<210> SEQ ID NO 312
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 312
accauaaaug uccggugugt t                                               21

<210> SEQ ID NO 313
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 313
ggaccauuuc ccgguuuagt t                                               21

<210> SEQ ID NO 314
<211> LENGTH: 21
```

```
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 314
cuaaaccggg aaauggcct t                                          21

<210> SEQ ID NO 315
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 315
accauuuccc gguuuagugt t                                         21

<210> SEQ ID NO 316
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 316
cacuaaaccg ggaaauggut t                                         21

<210> SEQ ID NO 317
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 317
auuucccggu uuagugccat t                                         21

<210> SEQ ID NO 318
<211> LENGTH: 21
<212> TYPE: DNA
<213> ORGANISM: Artificial sequence
<220> FEATURE:
```

<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 318
uggcacuaaa ccgggaaaut t                                              21

<210> SEQ ID NO 319
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 319
aaccugauca gaagaacggt t                                              21

<210> SEQ ID NO 320
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 320
ccguucuucu gaucagguut t                                              21

<210> SEQ ID NO 321
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 321
ucaguuuauu uauuacgguu t                                              21

<210> SEQ ID NO 322
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.

-continued

```
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 322
accguaauaa auaaacugat t                                              21

<210> SEQ ID NO 323
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 323
gugcaugacc cgaacugact t                                              21

<210> SEQ ID NO 324
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 324
gucaguucgg gucaugcact t                                              21

<210> SEQ ID NO 325
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 325
augaguucac guaccugagt t                                              21

<210> SEQ ID NO 326
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
```

-continued

```
<222> LOCATION: 1..19
<223> OTHER INFORMATION: /mod_base = "2'-hydroxy corresponding base"

<400> SEQUENCE: 326
cucagguacg ugaacucaut t                                                    21

<210> SEQ ID NO 327
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 327
agcgucauua cccuggcaut t                                                    21

<210> SEQ ID NO 328
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 328
augccagggu aaugacgcut t                                                    21

<210> SEQ ID NO 329
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 329
gcgucauuac ccuggcauat t                                                    21

<210> SEQ ID NO 330
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

-continued

```
<400> SEQUENCE: 330
uaugccaggg uaaugacgct t                                              21

<210> SEQ ID NO 331
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 331
gucauuaccc uggcauaugt t                                              21

<210> SEQ ID NO 332
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 332
cauaugccag gguaaugact t                                              21

<210> SEQ ID NO 333
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 333
acagcaauag aucuccgugt t                                              21

<210> SEQ ID NO 334
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 334
cacggagauc uauugcugut t                                              21
```

```
<210> SEQ ID NO 335
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 335
ggacauucag aguucuuagt t                                              21

<210> SEQ ID NO 336
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 336
cuaagaacuc ugaaugucct t                                              21

<210> SEQ ID NO 337
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 337
ucuacauaaa uaagcgaggt t                                              21

<210> SEQ ID NO 338
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 338
ccucgcuuau uuauguagat t                                              21

<210> SEQ ID NO 339
```

```
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 339
uaaauaagcg aggcacuuct t                                              21

<210> SEQ ID NO 340
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 340
gaagugccuc gcuuauuuat t                                              21

<210> SEQ ID NO 341
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 341
ugcccugaug guuauaucut t                                              21

<210> SEQ ID NO 342
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 342
agauauaacc aucagggcat t                                              21

<210> SEQ ID NO 343
<211> LENGTH: 21
<212> TYPE: DNA
<213> ORGANISM: Artificial sequence
```

```
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 343
caacccggau uuuaacuact t                                              21

<210> SEQ ID NO 344
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 344
guaguuaaaa uccggguugt t                                              21

<210> SEQ ID NO 345
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 345
gggaaaaucu auaugaucut t                                              21

<210> SEQ ID NO 346
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 346
agaucauaua gauuuccct t                                               21

<210> SEQ ID NO 347
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
```

<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 347
gcccucgaga ugcuccggat t                                             21

<210> SEQ ID NO 348
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 348
uccggagcau cucgagggct t                                             21

<210> SEQ ID NO 349
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 349
agggauugac acaaccucut t                                             21

<210> SEQ ID NO 350
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 350
agagguugug ucaaucccut t                                             21

<210> SEQ ID NO 351
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:

<221> NAME/KEY: modified_base
<222> LOCATION: 1..19
<223> OTHER INFORMATION: /mod_base = "2'-hydroxy corresponding base"

<400> SEQUENCE: 351
gggauugaca caaccucuct t                                              21

<210> SEQ ID NO 352
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 352
gagagguugu gucaauccct t                                              21

<210> SEQ ID NO 353
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 353
cacaauggau caccuuuaat t                                              21

<210> SEQ ID NO 354
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 354
uuaaagguga uccauugugt t                                              21

<210> SEQ ID NO 355
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

```
<400> SEQUENCE: 355
ccgcucugau ccuuacaact t                                              21

<210> SEQ ID NO 356
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 356
guuguaagga ucagagcggt t                                              21

<210> SEQ ID NO 357
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 357
auccuuacaa ccagcgcagt t                                              21

<210> SEQ ID NO 358
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 358
cugcgcuggu uguaaggaut t                                              21

<210> SEQ ID NO 359
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 359
```
agcgcaggau gucuuuucut t         21

<210> SEQ ID NO 360
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 360
agaaaagaca uccugcgcut t         21

<210> SEQ ID NO 361
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 361
cuuuucuagg ccucgccuct t         21

<210> SEQ ID NO 362
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 362
gaggcgaggc cuagaaaagt t         21

<210> SEQ ID NO 363
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 363
cuggaaaacg ccgggcuagt t         21

```
<210> SEQ ID NO 364
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 364
cuagcccggc guuuccagt t                                              21

<210> SEQ ID NO 365
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 365
aaacgccggg cuagucaugt t                                             21

<210> SEQ ID NO 366
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 366
caugacuagc ccggcguuut t                                             21

<210> SEQ ID NO 367
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 367
aacgccgggc uagucauggt t                                             21

<210> SEQ ID NO 368
<211> LENGTH: 21
<212> TYPE: DNA
```

```
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 368
ccaugacuag cccggcguut t                                              21

<210> SEQ ID NO 369
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 369
agaccacgaa agccaucggt t                                              21

<210> SEQ ID NO 370
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 370
ccgauggcuu ucguggucut t                                              21

<210> SEQ ID NO 371
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 371
cucccuagaa gcccucuuct t                                              21

<210> SEQ ID NO 372
<211> LENGTH: 21
<212> TYPE: DNA
<213> ORGANISM: Artificial sequence
<220> FEATURE:
<223> OTHER INFORMATION: Further siRNAs specific for Nav1.8
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 372
gaagagggcu ucuagggagt t                                             21

<210> SEQ ID NO 373
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 373
agaugaacac caaccgccgt t                                             21

<210> SEQ ID NO 374
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 374
cggcgguugg uguucaucut t                                             21

<210> SEQ ID NO 375
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 375
augaacacca accgccgcct t                                             21

<210> SEQ ID NO 376
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
```

<220> FEATURE:
<221> NAME/KEY: modified_base
<222> LOCATION: 1..19
<223> OTHER INFORMATION: /mod_base = "2'-hydroxy corresponding base"

<400> SEQUENCE: 376
ggcggcgguu gguguucaut t                                              21

<210> SEQ ID NO 377
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 377
aaccgccgcc cacuagugat t                                              21

<210> SEQ ID NO 378
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 378
ucacuagugg gcggcgguut t                                              21

<210> SEQ ID NO 379
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 379
accgccgccc acuagugagt t                                              21

<210> SEQ ID NO 380
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19

<223> OTHER INFORMATION: /mod_base = "2'-hydroxy corresponding base"

<400> SEQUENCE: 380
cucacuagug ggcggcggut t                    21

<210> SEQ ID NO 381
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 381
gcugucgaug ucucggcaut t                    21

<210> SEQ ID NO 382
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 382
augccgagac aucgacagct t                    21

<210> SEQ ID NO 383
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 383
ucgaugucuc ggcauucgat t                    21

<210> SEQ ID NO 384
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 384

-continued ucgaaugccg agacaucgat t                                                    21

<210> SEQ ID NO 385
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 385
ucucggcauu cgaugcaggt t                                                    21

<210> SEQ ID NO 386
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 386
ccugcaucga augccgagat t                                                    21

<210> SEQ ID NO 387
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 387
ggcauucgau gcaggacaat t                                                    21

<210> SEQ ID NO 388
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 388
uuguccugca ucgaaugcct t                                                    21

<210> SEQ ID NO 389
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 389
gcauucgaug caggacaaat t                                              21

<210> SEQ ID NO 390
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 390
uuuguccugc aucgaaugct t                                              21

<210> SEQ ID NO 391
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 391
cuuagaugaa ccuuuccggt t                                              21

<210> SEQ ID NO 392
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 392
ccggaaaggu ucaucuaagt t                                              21

<210> SEQ ID NO 393
<211> LENGTH: 21

```
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 393
gaguguuguc aguaucauau t                                              21

<210> SEQ ID NO 394
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 394
uaugauacug acaacacuct t                                              21

<210> SEQ ID NO 395
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 395
caguaucaua accuccguct t                                              21

<210> SEQ ID NO 396
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 396
gacggagguu augauacugt t                                              21

<210> SEQ ID NO 397
<211> LENGTH: 21
<212> TYPE: DNA
<213> ORGANISM: Artificial sequence
<220> FEATURE:
```

```
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 397
cucgaggagu cugaacagat t                                              21

<210> SEQ ID NO 398
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 398
ucuguucaga cuccucgagt t                                              21

<210> SEQ ID NO 399
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 399
guaucugauc ugggauugct t                                              21

<210> SEQ ID NO 400
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 400
gcaaucccag aucagauact t                                              21

<210> SEQ ID NO 401
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
```

```
            base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 401
agacaauucu cuuugggcut t                                              21

<210> SEQ ID NO 402
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 402
agcccaaaga gaauugucut t                                              21

<210> SEQ ID NO 403
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 403
caccuugugc aucguggugt t                                              21

<210> SEQ ID NO 404
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 404
caccacgaug cacaaggugt t                                              21

<210> SEQ ID NO 405
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
```

```
<222> LOCATION: 1..19
<223> OTHER INFORMATION: /mod_base = "2'-hydroxy corresponding base"

<400> SEQUENCE: 405
gcaugagccc uaccuucgat t                                              21

<210> SEQ ID NO 406
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 406
ucgaagguag ggcucaugct t                                              21

<210> SEQ ID NO 407
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 407
uaccuucgaa gccaugcuct t                                              21

<210> SEQ ID NO 408
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 408
gagcauggcu ucgaagguat t                                              21

<210> SEQ ID NO 409
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 409
caaaaucauu gccuucgact t                                              21

<210> SEQ ID NO 410
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 410
gucgaaggca augauuuugt t                                              21

<210> SEQ ID NO 411
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 411
aucauugccu ucgacccaut t                                              21

<210> SEQ ID NO 412
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 412
augggucgaa ggcaaugaut t                                              21

<210> SEQ ID NO 413
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 413
ucauugccuu cgacccauat t                                              21
```

```
<210> SEQ ID NO 414
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 414
uaugggucga aggcaaugat t                                           21

<210> SEQ ID NO 415
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 415
auugccuucg acccauacut t                                           21

<210> SEQ ID NO 416
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 416
aguauggguc gaaggcaaut t                                           21

<210> SEQ ID NO 417
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 417
ucgacccaua cuauuauuut t                                           21

<210> SEQ ID NO 418
```

```
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 418
aaauaauagu augggucgat t                                            21

<210> SEQ ID NO 419
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 419
caucaucguc acugugagut t                                            21

<210> SEQ ID NO 420
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 420
acucacagug acgaugaugt t                                            21

<210> SEQ ID NO 421
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 421
caucgucacu gugagucugt t                                            21

<210> SEQ ID NO 422
<211> LENGTH: 21
<212> TYPE: DNA
<213> ORGANISM: Artificial sequence
```

```
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 422
cagacucaca gugacgaugt t                                              21

<210> SEQ ID NO 423
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 423
ucgucacugu gagucugcut t                                              21

<210> SEQ ID NO 424
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 424
agcagacuca cagugacgat t                                              21

<210> SEQ ID NO 425
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 425
ggaaaacuac cguaacaact t                                              21

<210> SEQ ID NO 426
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
```

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 426
guuguuacgg uaguuuccu t                                                    21

<210> SEQ ID NO 427
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 427
uaccguaaca accgaaaaau t                                                   21

<210> SEQ ID NO 428
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 428
uuuuucgguu guuacgguau t                                                   21

<210> SEQ ID NO 429
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 429
cguaacaacc gaaaaauau t                                                    21

<210> SEQ ID NO 430
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
```

```
<221> NAME/KEY: modified_base
<222> LOCATION: 1..19
<223> OTHER INFORMATION: /mod_base = "2'-hydroxy corresponding base"

<400> SEQUENCE: 430
uauuuuuucg guuguuacgt t                                               21

<210> SEQ ID NO 431
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 431
aaaauccaua ugccucauct t                                               21

<210> SEQ ID NO 432
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 432
gaugaggcau auggauuuut t                                               21

<210> SEQ ID NO 433
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 433 cguucaucg cccugcuaut t                                                21

<210> SEQ ID NO 434
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 434
auagcagggc gaugaacagt t                                              21

<210> SEQ ID NO 435
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 435
uguucaucgc ccugcuauut t                                              21

<210> SEQ ID NO 436
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 436
aauagcaggg cgaugaacat t                                              21

<210> SEQ ID NO 437
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 437
cccugcuauu gaacucuuut t                                              21

<210> SEQ ID NO 438
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 438
```
aaagaguuca auagcagggt t                                              21

<210> SEQ ID NO 439
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 439
ggccaucgua ccaaacaggt t                                              21

<210> SEQ ID NO 440
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 440
ccuguuuggu acgauggcct t                                              21

<210> SEQ ID NO 441
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 441
ccaucguacc aaacaggcut t                                              21

<210> SEQ ID NO 442
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 442
agccuguuug guacgauggt t                                              21

<210> SEQ ID NO 443
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 443
cagugacuuc aucgcuaaut t                                             21

<210> SEQ ID NO 444
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 444
auuagcgaug aagucacugt t                                             21

<210> SEQ ID NO 445
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 445
cuucaucgcu aauccgacut t                                             21

<210> SEQ ID NO 446
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 446
agucggauua gcgaugaagt t                                             21

<210> SEQ ID NO 447
<211> LENGTH: 21
<212> TYPE: DNA

```
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 447
uaauccgacu guguggguct t                                              21

<210> SEQ ID NO 448
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 448
gacccacaca gucggauuat t                                              21

<210> SEQ ID NO 449
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 449
gaaucugauc uugaugacut t                                              21

<210> SEQ ID NO 450
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 450
agucaucaag aucagauuct t                                              21

<210> SEQ ID NO 451
<211> LENGTH: 21
<212> TYPE: DNA
<213> ORGANISM: Artificial sequence
<220> FEATURE:
<223> OTHER INFORMATION: Further siRNAs specific for Nav1.8
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 451
aagaguccau gggauguggt t                                                  21

<210> SEQ ID NO 452
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 452
ccacauccca uggacucuut t                                                  21

<210> SEQ ID NO 453
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 453
gcaggugcgc aagacuugct t                                                  21

<210> SEQ ID NO 454
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 454
gcaagucuug cgcaccugct t                                                  21

<210> SEQ ID NO 455
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 455
gcgcaagacu ugcuaccgut t                                                    21

<210> SEQ ID NO 456
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 456
acgguagcaa gucuugcgct t                                                    21

<210> SEQ ID NO 457
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 457
aagacuugcu accguaucgt t                                                    21

<210> SEQ ID NO 458
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 458
cgauacggua gcaagucuut t                                                    21

<210> SEQ ID NO 459
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

```
<223> OTHER INFORMATION: /mod_base = "2'-hydroxy corresponding base"

<400> SEQUENCE: 459
gacuugcuac cguaucgugt t                                              21

<210> SEQ ID NO 460
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 460
cacgauacgg uagcaaguct t                                              21

<210> SEQ ID NO 461
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 461
cucauuguga auaucucact t                                              21

<210> SEQ ID NO 462
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 462
gugagauauu cacaaugagt t                                              21

<210> SEQ ID NO 463
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 463
```
ugauaagucu cacagcgaau t                              21

<210> SEQ ID NO 464
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 464
uucgcuguga gacuuaucat t                              21

<210> SEQ ID NO 465
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 465
aucaaagccc uucgaaccct t                              21

<210> SEQ ID NO 466
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 466
ggguucgaag ggcuuugaut t                              21

<210> SEQ ID NO 467
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 467
aaagcccuuc gaaccuuct t                               21

<210> SEQ ID NO 468
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 468
gaaggguucg aagggcuuut t                                              21

<210> SEQ ID NO 469
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 469
ccuucgaacc cuucgcgcut t                                              21

<210> SEQ ID NO 470
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 470
agcgcgaagg guucgaaggt t                                              21

<210> SEQ ID NO 471
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
    base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 471
cuucgaaccc uucgcgcuct t                                              21

<210> SEQ ID NO 472
<211> LENGTH: 21

```
<210> SEQ ID NO 472
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 472
gagcgcgaag gguucgaagt t                                              21

<210> SEQ ID NO 473
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 473
ugcaucaacu auaccgaugt t                                              21

<210> SEQ ID NO 474
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 474
caucgguaua guugaugcat t                                              21

<210> SEQ ID NO 475
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 475
cccuuguacc uuugucgaut t                                              21

<210> SEQ ID NO 476
<211> LENGTH: 21
<212> TYPE: DNA
<213> ORGANISM: Artificial sequence
<220> FEATURE:
```

```
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 476
aucgacaaag guacaagggt t                                              21

<210> SEQ ID NO 477
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 477
uuguaccuuu gucgauugut t                                              21

<210> SEQ ID NO 478
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 478
acaaucgaca aagguacaat t                                              21

<210> SEQ ID NO 479
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 479
uuugauaaug uugcaauggt t                                              21

<210> SEQ ID NO 480
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
```

-continued

```
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 480
ccauugcaac auuaucaaat t                                              21

<210> SEQ ID NO 481
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 481
gcaauggguu accuugcact t                                              21

<210> SEQ ID NO 482
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 482
gugcaaggua acccauugct t                                              21

<210> SEQ ID NO 483
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 483
uggguuaccu ugcacuucut t                                              21

<210> SEQ ID NO 484
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
```

-continued

```
<222> LOCATION: 1..19
<223> OTHER INFORMATION: /mod_base = "2'-hydroxy corresponding base"

<400> SEQUENCE: 484
agaagugcaa gguaacccat t                                              21

<210> SEQ ID NO 485
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 485
gcuguugauu cccgggaggt t                                              21

<210> SEQ ID NO 486
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 486
ccucccggga aucaacagct t                                              21

<210> SEQ ID NO 487
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 487
aucgugacca gacaagcuut t                                              21

<210> SEQ ID NO 488
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 488
aagcuugucu ggucacgaut t                                              21

<210> SEQ ID NO 489
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 489
cgucuucaca ggcgaaugut t                                              21

<210> SEQ ID NO 490
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 490
acauucgccu gugaagacgt t                                              21

<210> SEQ ID NO 491
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 491
ucacaggcga augugucaut t                                              21

<210> SEQ ID NO 492
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 492
augacacauu cgccugugat t                                              21
```

<210> SEQ ID NO 493
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 493
cacaggcgaa ugugucaugt t                                            21

<210> SEQ ID NO 494
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 494
caugacacau ucgccugugt t                                            21

<210> SEQ ID NO 495
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 495
caggcgaaug ugucaugaat t                                            21

<210> SEQ ID NO 496
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 496
uucaugacac auucgccugt t                                            21

<210> SEQ ID NO 497

```
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 497
aggcgaaugu gucaugaagt t                                                 21

<210> SEQ ID NO 498
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 498
cuucaugaca cauucgccut t                                                 21

<210> SEQ ID NO 499
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 499
uguucgcuuu gaggcaguat t                                                 21

<210> SEQ ID NO 500
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 500
uacugccuca aagcgaacat t                                                 21

<210> SEQ ID NO 501
<211> LENGTH: 21
<212> TYPE: DNA
<213> ORGANISM: Artificial sequence
```

```
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 501
gcaguacuac uucacaaaut t                                        21

<210> SEQ ID NO 502
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 502
auuugugaag uaguacugct t                                        21

<210> SEQ ID NO 503
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 503
uccauugcga gccugauuut t                                        21

<210> SEQ ID NO 504
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 504
aaaucaggcu cgcaauggat t                                        21

<210> SEQ ID NO 505
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
```

```
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 505
ccauugcgag ccugauuuut t                                              21

<210> SEQ ID NO 506
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 506
aaaaucaggc ucgcaauggt t                                              21

<210> SEQ ID NO 507
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 507
aucgggcugu ugcuauucct t                                              21

<210> SEQ ID NO 508
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 508
ggaauagcaa cagcccgaut t                                              21

<210> SEQ ID NO 509
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
```

```
<221> NAME/KEY: modified_base
<222> LOCATION: 1..19
<223> OTHER INFORMATION: /mod_base = "2'-hydroxy corresponding base"

<400> SEQUENCE: 509
aaaacccaau cgaaauauat t                                              21

<210> SEQ ID NO 510
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 510
uauauuucga uuggguuuut t                                              21

<210> SEQ ID NO 511
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 511
caaucgaaau auacugauct t                                              21

<210> SEQ ID NO 512
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 512
gaucaguaua uuucgauugt t                                              21

<210> SEQ ID NO 513
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"
```

```
<400> SEQUENCE: 513
aaucgaaaua uacugaucct t                                              21

<210> SEQ ID NO 514
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 514
ggaucaguau auuucgauut t                                              21

<210> SEQ ID NO 515
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 515
ucgaaauaua cugauccagt t                                              21

<210> SEQ ID NO 516
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 516
cuggaucagu auauuucgat t                                              21

<210> SEQ ID NO 517
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 517
```
aaucauccua ugaaccaaut t                                                 21

<210> SEQ ID NO 518
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 518
auugguucau aggaugauut t                                                 21

<210> SEQ ID NO 519
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 519
uaugaaccaa uagcaaccat t                                                 21

<210> SEQ ID NO 520
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 520
ugguugcuau ugguucauat t                                                 21

<210> SEQ ID NO 521
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 521
cacucuccga uggaagcaat t                                                 21

```
<210> SEQ ID NO 522
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 522
uugcuuccau cggagagugt t                                              21

<210> SEQ ID NO 523
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 523
cuaucggagc uaugugcugt t                                              21

<210> SEQ ID NO 524
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 524
cagcacauag cuccgauagt t                                              21

<210> SEQ ID NO 525
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 525
agcaaaugaa aauuguguat t                                              21

<210> SEQ ID NO 526
<211> LENGTH: 21
<212> TYPE: DNA
```

```
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 526
uacacaauuu ucauuugcut t                                                     21

<210> SEQ ID NO 527
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 527
uacucccaga caaaucugat t                                                     21

<210> SEQ ID NO 528
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 528
ucagauuugu cuggaguat t                                                      21

<210> SEQ ID NO 529
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 529
agagugucac uagaggccut t                                                     21

<210> SEQ ID NO 530
<211> LENGTH: 21
<212> TYPE: DNA
<213> ORGANISM: Artificial sequence
<220> FEATURE:
<223> OTHER INFORMATION: Further siRNAs specific for Nav1.8
```

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 530
aggccucuag ugacacucut t                                              21

<210> SEQ ID NO 531
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 531
ggccuuagug auagagucat t                                              21

<210> SEQ ID NO 532
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 532
ugacucuauc acuaaggcct t                                              21

<210> SEQ ID NO 533
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 533
agugauagag ucaacaugat t                                              21

<210> SEQ ID NO 534
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
```

```
<220> FEATURE:
<221> NAME/KEY: modified_base
<222> LOCATION: 1..19
<223> OTHER INFORMATION: /mod_base = "2'-hydroxy corresponding base"

<400> SEQUENCE: 534
ucauguugac ucuaucacut t                                              21

<210> SEQ ID NO 535
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 535
gauagaguca acaugaggat t                                              21

<210> SEQ ID NO 536
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 536
uccucauguu gacucuauct t                                              21

<210> SEQ ID NO 537
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 537
caucuagcuc aauacaaaat t                                              21

<210> SEQ ID NO 538
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
```

<223> OTHER INFORMATION: /mod_base = "2'-hydroxy corresponding base"

<400> SEQUENCE: 538
uuuuguauug agcuagaugt t          21

<210> SEQ ID NO 539
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 539
cuagcucaau acaaaaugat t          21

<210> SEQ ID NO 540
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 540
ucauuuugua uugagcuagt t          21

<210> SEQ ID NO 541
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 541
aguauggagc ugauugccct t          21

<210> SEQ ID NO 542
<211> LENGTH: 21
<212> TYPE: DNA
<213> ORGANISM: Artificial sequence
<220> FEATURE:
<223> OTHER INFORMATION: Further siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1..19
<223> OTHER INFORMATION: /mod_base = "2'-hydroxy corresponding base"

<400> SEQUENCE: 542
gggcaaucag cuccauacut t    21

<210> SEQ ID NO 543
<211> LENGTH: 44
<212> TYPE: DNA
<213> ORGANISM: Artificial sequence
<220> FEATURE:
<223> OTHER INFORMATION: Human Nav1.8 probeset

<400> SEQUENCE: 543
tttggaggtt aaaggtgatc cattttttct cttggaaaga aagt    44

<210> SEQ ID NO 544
<211> LENGTH: 40
<212> TYPE: DNA
<213> ORGANISM: Artificial sequence
<220> FEATURE:
<223> OTHER INFORMATION: Human Nav1.8 probeset

<400> SEQUENCE: 544
ggcgttttcc agaggcgagt ttttctcttg gaaagaaagt    40

<210> SEQ ID NO 545
<211> LENGTH: 39
<212> TYPE: DNA
<213> ORGANISM: Artificial sequence
<220> FEATURE:
<223> OTHER INFORMATION: Human Nav1.8 probeset

<400> SEQUENCE: 545
ccagcagcag agagccccctt tttctcttgg aaagaaagt    39

<210> SEQ ID NO 546
<211> LENGTH: 41
<212> TYPE: DNA
<213> ORGANISM: Artificial sequence
<220> FEATURE:
<223> OTHER INFORMATION: Human Nav1.8 probeset

<400> SEQUENCE: 546
ctgggttgag gaagagggct ttttctctt ggaaagaaag t    41

<210> SEQ ID NO 547
<211> LENGTH: 41
<212> TYPE: DNA
<213> ORGANISM: Artificial sequence
<220> FEATURE:
<223> OTHER INFORMATION: Human Nav1.8 probeset

<400> SEQUENCE: 547
aacactcatt gccctttggg tttttctctt ggaaagaaag t    41

<210> SEQ ID NO 548
<211> LENGTH: 45
<212> TYPE: DNA
<213> ORGANISM: Artificial sequence
<220> FEATURE:
<223> OTHER INFORMATION: Human Nav1.8 probeset

<400> SEQUENCE: 548
aaggacggag gttatgatac tgacttttc tcttggaaag aaagt    45

<210> SEQ ID NO 549
<211> LENGTH: 44
<212> TYPE: DNA

<213> ORGANISM: Artificial sequence
<220> FEATURE:
<223> OTHER INFORMATION: Human Nav1.8 probeset

<400> SEQUENCE: 549
tgttcagact cctcgagttc ctctttttct cttggaaaga aagt    44

<210> SEQ ID NO 550
<211> LENGTH: 47
<212> TYPE: DNA
<213> ORGANISM: Artificial sequence
<220> FEATURE:
<223> OTHER INFORMATION: Human Nav1.8 probeset

<400> SEQUENCE: 550
ctatgccttc tctcactggc atttttttag gcataggacc cgtgtct    47

<210> SEQ ID NO 551
<211> LENGTH: 46
<212> TYPE: DNA
<213> ORGANISM: Artificial sequence
<220> FEATURE:
<223> OTHER INFORMATION: Human Nav1.8 probeset

<400> SEQUENCE: 551
ctggttgtaa ggatcagagc ggttttttagg cataggaccc gtgtct    46

<210> SEQ ID NO 552
<211> LENGTH: 46
<212> TYPE: DNA
<213> ORGANISM: Artificial sequence
<220> FEATURE:
<223> OTHER INFORMATION: Human Nav1.8 probeset

<400> SEQUENCE: 552
aacacactgc catgactagc ccttttttagg cataggaccc gtgtct    46

<210> SEQ ID NO 553
<211> LENGTH: 44
<212> TYPE: DNA
<213> ORGANISM: Artificial sequence
<220> FEATURE:
<223> OTHER INFORMATION: Human Nav1.8 probeset

<400> SEQUENCE: 553
gatggctttc gtggtctcca tttttaggca taggacccgt gtct    44

<210> SEQ ID NO 554
<211> LENGTH: 41
<212> TYPE: DNA
<213> ORGANISM: Artificial sequence
<220> FEATURE:
<223> OTHER INFORMATION: Human Nav1.8 probeset

<400> SEQUENCE: 554
ctggccagca cccccacttt ttaggcatag gacccgtgtc t    41

<210> SEQ ID NO 555
<211> LENGTH: 44
<212> TYPE: DNA
<213> ORGANISM: Artificial sequence
<220> FEATURE:
<223> OTHER INFORMATION: Human Nav1.8 probeset

<400> SEQUENCE: 555
catgcctgga gtcagggttg ttttttaggca taggacccgt gtct    44

```
<210> SEQ ID NO 556
<211> LENGTH: 44
<212> TYPE: DNA
<213> ORGANISM: Artificial sequence
<220> FEATURE:
<223> OTHER INFORMATION: Human Nav1.8 probeset

<400> SEQUENCE: 556
agacatcgac agctccaggg tttttaggca taggacccgt gtct                    44

<210> SEQ ID NO 557
<211> LENGTH: 42
<212> TYPE: DNA
<213> ORGANISM: Artificial sequence
<220> FEATURE:
<223> OTHER INFORMATION: Human Nav1.8 probeset

<400> SEQUENCE: 557
gtcctgcatc gaatgccgtt tttaggcata ggacccgtgt ct                      42

<210> SEQ ID NO 558
<211> LENGTH: 43
<212> TYPE: DNA
<213> ORGANISM: Artificial sequence
<220> FEATURE:
<223> OTHER INFORMATION: Human Nav1.8 probeset

<400> SEQUENCE: 558
caagcagggt gggcacttct ttttaggcat aggacccgtg tct                     43

<210> SEQ ID NO 559
<211> LENGTH: 21
<212> TYPE: DNA
<213> ORGANISM: Artificial sequence
<220> FEATURE:
<223> OTHER INFORMATION: Human Nav1.8 probeset

<400> SEQUENCE: 559
tgtgggagtg gagagaggtt g                                             21

<210> SEQ ID NO 560
<211> LENGTH: 24
<212> TYPE: DNA
<213> ORGANISM: Artificial sequence
<220> FEATURE:
<223> OTHER INFORMATION: Human Nav1.8 probeset

<400> SEQUENCE: 560
ccctctgaca ctcttggctt tatt                                          24

<210> SEQ ID NO 561
<211> LENGTH: 24
<212> TYPE: DNA
<213> ORGANISM: Artificial sequence
<220> FEATURE:
<223> OTHER INFORMATION: Human Nav1.8 probeset

<400> SEQUENCE: 561
ggtgatttgt tgtcttctgt ggag                                          24

<210> SEQ ID NO 562
<211> LENGTH: 21
<212> TYPE: DNA
<213> ORGANISM: Artificial sequence
<220> FEATURE:
```

<223> OTHER INFORMATION: Human Nav1.8 probeset

<400> SEQUENCE: 562
gcctagaaaa gacatcctgc g                                              21

<210> SEQ ID NO 563
<211> LENGTH: 19
<212> TYPE: DNA
<213> ORGANISM: Artificial sequence
<220> FEATURE:
<223> OTHER INFORMATION: Human Nav1.8 probeset

<400> SEQUENCE: 563
gccaggggac cggaaatgg                                                 19

<210> SEQ ID NO 564
<211> LENGTH: 23
<212> TYPE: DNA
<213> ORGANISM: Artificial sequence
<220> FEATURE:
<223> OTHER INFORMATION: Human Nav1.8 probeset

<400> SEQUENCE: 564
ccctcaggga gtgagatatc tcg                                            23

<210> SEQ ID NO 565
<211> LENGTH: 24
<212> TYPE: DNA
<213> ORGANISM: Artificial sequence
<220> FEATURE:
<223> OTHER INFORMATION: Human Nav1.8 probeset

<400> SEQUENCE: 565
ggaaagactc catcatctgt gact                                           24

<210> SEQ ID NO 566
<211> LENGTH: 18
<212> TYPE: DNA
<213> ORGANISM: Artificial sequence
<220> FEATURE:
<223> OTHER INFORMATION: Human Nav1.8 probeset

<400> SEQUENCE: 566
tctagggagg gggccttg                                                  18

<210> SEQ ID NO 567
<211> LENGTH: 21
<212> TYPE: DNA
<213> ORGANISM: Artificial sequence
<220> FEATURE:
<223> OTHER INFORMATION: Human Nav1.8 probeset

<400> SEQUENCE: 567
gcggttggtg ttcatcttct c                                              21

<210> SEQ ID NO 568
<211> LENGTH: 19
<212> TYPE: DNA
<213> ORGANISM: Artificial sequence
<220> FEATURE:
<223> OTHER INFORMATION: Human Nav1.8 probeset

<400> SEQUENCE: 568
gcaagctcac tagtgggcg                                                 19

```
<210> SEQ ID NO 569
<211> LENGTH: 25
<212> TYPE: DNA
<213> ORGANISM: Artificial sequence
<220> FEATURE:
<223> OTHER INFORMATION: Human Nav1.8 probeset

<400> SEQUENCE: 569
tctgctgaca agaaagtctt ctttt                                          25

<210> SEQ ID NO 570
<211> LENGTH: 23
<212> TYPE: DNA
<213> ORGANISM: Artificial sequence
<220> FEATURE:
<223> OTHER INFORMATION: Human Nav1.8 probeset

<400> SEQUENCE: 570
cccggaaagg ttcatctaag tat                                            23

<210> SEQ ID NO 571
<211> LENGTH: 41
<212> TYPE: DNA
<213> ORGANISM: Artificial sequence
<220> FEATURE:
<223> OTHER INFORMATION: Human GAPDH probeset

<400> SEQUENCE: 571
gaatttgcca tgggtggaat tttttctctt ggaaagaaag t                        41

<210> SEQ ID NO 572
<211> LENGTH: 41
<212> TYPE: DNA
<213> ORGANISM: Artificial sequence
<220> FEATURE:
<223> OTHER INFORMATION: Human GAPDH probeset

<400> SEQUENCE: 572
ggagggatct cgctcctgga tttttctctt ggaaagaaag t                        41

<210> SEQ ID NO 573
<211> LENGTH: 40
<212> TYPE: DNA
<213> ORGANISM: Artificial sequence
<220> FEATURE:
<223> OTHER INFORMATION: Human GAPDH probeset

<400> SEQUENCE: 573
ccccagcctt ctccatggtt ttttctcttg gaaagaaagt                          40

<210> SEQ ID NO 574
<211> LENGTH: 40
<212> TYPE: DNA
<213> ORGANISM: Artificial sequence
<220> FEATURE:
<223> OTHER INFORMATION: Human GAPDH probeset

<400> SEQUENCE: 574 gctccccct gcaaatgagt ttttctcttg gaaagaaagt                           40

<210> SEQ ID NO 575
<211> LENGTH: 42
<212> TYPE: DNA
<213> ORGANISM: Artificial sequence
<220> FEATURE:
<223> OTHER INFORMATION: Human GAPDH probeset
```

```
<400> SEQUENCE: 575
agccttgacg gtgccatgtt tttaggcata ggacccgtgt ct                42

<210> SEQ ID NO 576
<211> LENGTH: 45
<212> TYPE: DNA
<213> ORGANISM: Artificial sequence
<220> FEATURE:
<223> OTHER INFORMATION: Human GAPDH probeset

<400> SEQUENCE: 576
gatgacaagc ttcccgttct cttttttaggc ataggacccg tgtct            45

<210> SEQ ID NO 577
<211> LENGTH: 46
<212> TYPE: DNA
<213> ORGANISM: Artificial sequence
<220> FEATURE:
<223> OTHER INFORMATION: Human GAPDH probeset

<400> SEQUENCE: 577
agatggtgat gggatttcca ttttttaggc ataggaccc gtgtct             46

<210> SEQ ID NO 578
<211> LENGTH: 44
<212> TYPE: DNA
<213> ORGANISM: Artificial sequence
<220> FEATURE:
<223> OTHER INFORMATION: Human GAPDH probeset

<400> SEQUENCE: 578
gcatcgcccc acttgatttt tttttaggca taggacccgt gtct              44

<210> SEQ ID NO 579
<211> LENGTH: 43
<212> TYPE: DNA
<213> ORGANISM: Artificial sequence
<220> FEATURE:
<223> OTHER INFORMATION: Human GAPDH probeset

<400> SEQUENCE: 579
cacgacgtac tcagcgccat ttttaggcat aggacccgtg tct               43

<210> SEQ ID NO 580
<211> LENGTH: 46
<212> TYPE: DNA
<213> ORGANISM: Artificial sequence
<220> FEATURE:
<223> OTHER INFORMATION: Human GAPDH probeset

<400> SEQUENCE: 580
ggcagagatg atgacccttt tgtttttagg cataggaccc gtgtct            46

<210> SEQ ID NO 581
<211> LENGTH: 21
<212> TYPE: DNA
<213> ORGANISM: Artificial sequence
<220> FEATURE:
<223> OTHER INFORMATION: Human GAPDH probeset

<400> SEQUENCE: 581
ggtgaagacg ccagtggact c                                       21

<210> SEQ ID NO 582
<211> LENGTH: 45
```

```
<212> TYPE: DNA
<213> ORGANISM: Artificial sequence
<220> FEATURE:
<223> OTHER INFORMATION: Human Nav1.5 probeset

<400> SEQUENCE: 582
cgttttctcc tcttgcttct tctctttttc tcttggaaag aaagt          45

<210> SEQ ID NO 583
<211> LENGTH: 39
<212> TYPE: DNA
<213> ORGANISM: Artificial sequence
<220> FEATURE:
<223> OTHER INFORMATION: Human Nav1.5 probeset

<400> SEQUENCE: 583
gggagcctgt cctccccatt tttctcttgg aagaaagt                  39

<210> SEQ ID NO 584
<211> LENGTH: 39
<212> TYPE: DNA
<213> ORGANISM: Artificial sequence
<220> FEATURE:
<223> OTHER INFORMATION: Human Nav1.5 probeset

<400> SEQUENCE: 584
tcgcctgcga aggtgaatt tttctcttgg aagaaagt                   39

<210> SEQ ID NO 585
<211> LENGTH: 38
<212> TYPE: DNA
<213> ORGANISM: Artificial sequence
<220> FEATURE:
<223> OTHER INFORMATION: Human Nav1.5 probeset

<400> SEQUENCE: 585
ctctcgctct cccccgcttt ttctcttgga agaaagt                   38

<210> SEQ ID NO 586
<211> LENGTH: 38
<212> TYPE: DNA
<213> ORGANISM: Artificial sequence
<220> FEATURE:
<223> OTHER INFORMATION: Human Nav1.5 probeset

<400> SEQUENCE: 586
ccgggactgg gctgtccttt ttctcttgga agaaagt                   38

<210> SEQ ID NO 587
<211> LENGTH: 39
<212> TYPE: DNA
<213> ORGANISM: Artificial sequence
<220> FEATURE:
<223> OTHER INFORMATION: Human Nav1.5 probeset

<400> SEQUENCE: 587
ttttgccatg gagggcgttt tttctcttgg aaagaaagt                 39

<210> SEQ ID NO 588
<211> LENGTH: 47
<212> TYPE: DNA
<213> ORGANISM: Artificial sequence
<220> FEATURE:
<223> OTHER INFORMATION: Human Nav1.5 probeset

<400> SEQUENCE: 588
```
ggctgagatg attcattgct ctgtttttag gcataggacc cgtgtct    47

<210> SEQ ID NO 589
<211> LENGTH: 41
<212> TYPE: DNA
<213> ORGANISM: Artificial sequence
<220> FEATURE:
<223> OTHER INFORMATION: Human Nav1.5 probeset

<400> SEQUENCE: 589
gctgaggcca cgggtgattt ttaggcatag gacccgtgtc t    41

<210> SEQ ID NO 590
<211> LENGTH: 41
<212> TYPE: DNA
<213> ORGANISM: Artificial sequence
<220> FEATURE:
<223> OTHER INFORMATION: Human Nav1.5 probeset

<400> SEQUENCE: 590
aatgctcccg cggctggttt ttaggcatag gacccgtgtc t    41

<210> SEQ ID NO 591
<211> LENGTH: 41
<212> TYPE: DNA
<213> ORGANISM: Artificial sequence
<220> FEATURE:
<223> OTHER INFORMATION: Human Nav1.5 probeset

<400> SEQUENCE: 591
ctgggcactg gtccggcttt ttaggcatag gacccgtgtc t    41

<210> SEQ ID NO 592
<211> LENGTH: 41
<212> TYPE: DNA
<213> ORGANISM: Artificial sequence
<220> FEATURE:
<223> OTHER INFORMATION: Human Nav1.5 probeset

<400> SEQUENCE: 592
ggccaggagc cgaggttttt ttaggcatag gacccgtgtc t    41

<210> SEQ ID NO 593
<211> LENGTH: 46
<212> TYPE: DNA
<213> ORGANISM: Artificial sequence
<220> FEATURE:
<223> OTHER INFORMATION: Human Nav1.5 probeset

<400> SEQUENCE: 593
cccagtaatg agaccacccc attttttagg cataggaccc gtgtct    46

<210> SEQ ID NO 594
<211> LENGTH: 41
<212> TYPE: DNA
<213> ORGANISM: Artificial sequence
<220> FEATURE:
<223> OTHER INFORMATION: Human Nav1.5 probeset

<400> SEQUENCE: 594
cctctgggtc gcctgccttt ttaggcatag gacccgtgtc t    41

<210> SEQ ID NO 595
<211> LENGTH: 24
<212> TYPE: DNA
<213> ORGANISM: Artificial sequence

```
<220> FEATURE:
<223> OTHER INFORMATION: Human Nav1.5 probeset

<400> SEQUENCE: 595
cactcctcag ttcctgaaga catc                                            24

<210> SEQ ID NO 596
<211> LENGTH: 24
<212> TYPE: DNA
<213> ORGANISM: Artificial sequence
<220> FEATURE:
<223> OTHER INFORMATION: Human Nav1.5 probeset

<400> SEQUENCE: 596
ggaccatctt ctgagtcaga cttg                                            24

<210> SEQ ID NO 597
<211> LENGTH: 22
<212> TYPE: DNA
<213> ORGANISM: Artificial sequence
<220> FEATURE:
<223> OTHER INFORMATION: Human Nav1.5 probeset

<400> SEQUENCE: 597
aacgtggctt catagaagtc ct                                              22

<210> SEQ ID NO 598
<211> LENGTH: 22
<212> TYPE: DNA
<213> ORGANISM: Artificial sequence
<220> FEATURE:
<223> OTHER INFORMATION: Human Nav1.5 probeset

<400> SEQUENCE: 598
aatctgcttc agaacccagg tc                                              22

<210> SEQ ID NO 599
<211> LENGTH: 23
<212> TYPE: DNA
<213> ORGANISM: Artificial sequence
<220> FEATURE:
<223> OTHER INFORMATION: Human Nav1.5 probeset

<400> SEQUENCE: 599
tgtgctgttt tcatcatctg caa                                             23

<210> SEQ ID NO 600
<211> LENGTH: 20
<212> TYPE: DNA
<213> ORGANISM: Artificial sequence
<220> FEATURE:
<223> OTHER INFORMATION: Human Nav1.5 probeset

<400> SEQUENCE: 600
ccagcagtga tgtgtggtgg                                                 20

<210> SEQ ID NO 601
<211> LENGTH: 15
<212> TYPE: RNA
<213> ORGANISM: Artificial sequence
<220> FEATURE:
<223> OTHER INFORMATION: Human Nav1.5 probeset

<400> SEQUENCE: 601
gcagggccca gggca                                                      15
```

<210> SEQ ID NO 602
<211> LENGTH: 21
<212> TYPE: DNA
<213> ORGANISM: Artificial sequence
<220> FEATURE:
<223> OTHER INFORMATION: Human Nav1.5 probeset

<400> SEQUENCE: 602
tgcagtccac agtgctgttc t                                              21

<210> SEQ ID NO 603
<211> LENGTH: 18
<212> TYPE: DNA
<213> ORGANISM: Artificial sequence
<220> FEATURE:
<223> OTHER INFORMATION: Human Nav1.5 probeset

<400> SEQUENCE: 603
ggcttcctgg ggatgtgg                                                  18

<210> SEQ ID NO 604
<211> LENGTH: 21
<212> TYPE: DNA
<213> ORGANISM: Artificial sequence
<220> FEATURE:
<223> OTHER INFORMATION: Further modified siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 20..21
<223> OTHER INFORMATION: /mod_base = "2'-O-(2-methoxyethyl)
      corresponding base"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 604
cauccuauga accaauagct t                                              21

<210> SEQ ID NO 605
<211> LENGTH: 21
<212> TYPE: DNA
<213> ORGANISM: Artificial sequence
<220> FEATURE:
<223> OTHER INFORMATION: Further modified siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 20..21
<223> OTHER INFORMATION: /mod_base = "2'-O-(2-methoxyethyl)
      corresponding base"
<220> FEATURE:
<221> NAME/KEY: modified_base
<222> LOCATION: 1..19
<223> OTHER INFORMATION: /mod_base = "2'-hydroxy corresponding base"

<400> SEQUENCE: 605
gcuauugguu cauaggaugc t                                              21

<210> SEQ ID NO 606
<211> LENGTH: 21
<212> TYPE: DNA
<213> ORGANISM: Artificial sequence
<220> FEATURE:
<223> OTHER INFORMATION: Further modified siRNAs specific for Nav1.8

```
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 3, 4, 5, 6, 8, 12, 13, 16, 19
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "3'-thio 3'-cholesterol deoxy
      thymidine"
<220> FEATURE:
<221> NAME/KEY: modified_base
<222> LOCATION: 2, 7, 9, 10, 11, 14, 15, 17, 18
<223> OTHER INFORMATION: /mod_base = "2'-hydroxy corresponding base"

<400> SEQUENCE: 606
cauccuauga accaauagct t                                              21

<210> SEQ ID NO 607
<211> LENGTH: 21
<212> TYPE: DNA
<213> ORGANISM: Artificial sequence
<220> FEATURE:
<223> OTHER INFORMATION: Further modified siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 3, 11, 13
<223> OTHER INFORMATION: /mod_base = "2'-O-methyl corresponding base"
<220> FEATURE:
<221> NAME/KEY: modified_base
<222> LOCATION: 1, 2, 4, 5, 6, 7, 8, 9, 10, 12, 14, 15, 16, 17, 18, 19
<223> OTHER INFORMATION: /mod_base = "2'-hydroxy corresponding base"

<400> SEQUENCE: 607
gcuauugguu cauaggaugt t                                              21

<210> SEQ ID NO 608
<211> LENGTH: 21
<212> TYPE: DNA
<213> ORGANISM: Artificial sequence
<220> FEATURE:
<223> OTHER INFORMATION: Further modified siRNAs specific for Nav1.8
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 1, 2, 3, 4, 6, 7, 8, 12, 16, 17, 18
<223> OTHER INFORMATION: /mod_base = "2'-O-methyl corresponding base"
<220> FEATURE:
<221> NAME/KEY: modified_base
<222> LOCATION: 21
<223> OTHER INFORMATION: /mod_base = "3'-thio 3'-cholesterol deoxy
      thymidine"
<220> FEATURE:
<221> NAME/KEY: modified_base
<222> LOCATION: 5, 9, 10, 11, 13, 14, 15, 19
<223> OTHER INFORMATION: /mod_base = "2'-hydroxy corresponding base"

<400> SEQUENCE: 608
uuuugucuaa augaguucat t                                              21

<210> SEQ ID NO 609
<211> LENGTH: 21
<212> TYPE: DNA
<213> ORGANISM: Artificial sequence
<220> FEATURE:
<223> OTHER INFORMATION: Further modified siRNAs specific for Nav1.8
```

```
-continued
<220> FEATURE:
<223> OTHER INFORMATION: 5'-terminal nucleic acid is a nucleoside, i.e.
      base + sugar but lacking 5'-phosphate
<220> FEATURE:
<221> NAME/KEY: modified_base
<222> LOCATION: 7, 11, 15
<223> OTHER INFORMATION: /mod_base = "2'-O-methyl corresponding base"
<220> FEATURE:
<221> NAME/KEY: modified_base
<222> LOCATION: 1, 2, 3, 4, 5, 6, 8, 9, 10, 12, 13, 14, 16, 17, 18, 19
<223> OTHER INFORMATION: /mod_base = "2'-hydroxy corresponding base"

<400> SEQUENCE: 609
ugaacucauu uagacaaaat t                                              21
```

COMPOSITIONS AND METHODS FOR INHIBITING EXPRESSION OF NAV1.8 GENE

RELATED APPLICATIONS

This application claims the benefit of U.S. Provisional Application No. 60/733,816, filed Nov. 4, 2005; U.S. Provisional Application No. 60/741,586, filed Dec. 2, 2005; U.S. Provisional Application No. 60/763,202, filed Jan. 26, 2006; U.S. Provisional Application No. 60/795,443, filed Apr. 27, 2006; and U.S. Provisional Application No. 60/849,364, filed Oct. 4, 2006. The contents of these prior applications are incorporated herein by reference in their entirety.

SEQUENCE LISTING

This application incorporates by reference the sequence listing saved as an ASCII text file on CD-ROM. The sequence listing saved on CD-ROM was created on Nov. 3, 2006, and is identified as "14174-127001.txt." The file contains 217 KB of data. Three identical copies of the sequence listing have been submitted, including one "Computer-Readable Format" (CRF) and two "Official Copies" (Copy 1 and Copy 2).

FIELD OF THE INVENTION

This invention relates to double-stranded ribonucleic acid (dsRNA), and its use in mediating RNA interference to inhibit the expression of the Nav1.8 gene and the use of the dsRNA to treat pain.

BACKGROUND OF THE INVENTION

Neuropathic pain can be classified as peripheral and central neuropathic pain. Peripheral neuropathic pain is caused by injury or infection of peripheral sensory nerves, whereas central neuropathic pain is caused by damage to the CNS and/or the spinal cord. Both peripheral and central neuropathic pain can occur without obvious initial nerve damage.

A similar definition is given by the International Association for the Study of Pain (IASP, Seattle, Wash., USA): peripheral neuropathic pain is pain initiated or caused by a primary lesion or dysfunction in the peripheral nervous system. Central neuropathic pain is pain initiated or caused by a primary lesion or dysfunction in the central nervous system.

Peripheral lesions may be lesions of perpherial nerves, e.g. diabetic neuropathy, drug-inducted neuropathy, e.g. upon chemotherapy, lesions of nerve roots and posterior ganglia, e.g. post-herpetic neuralgia or nerve root avulsions, neuropathic cancer pain due to compression of peripheral nerves, nerve plexuses and nerve roots, etc. Central lesions may be lesions due to infarction, compressive tumors or abscesses, e.g. in the brainstem, or may be spinal cord lesions due to injury or operations (Jain K K, Emerging Drugs, 2000, 5:241-257; McQuay, 2002, European Journal of Pain 6 (Suppl. A): 11-18).

The above examples of peripheral and central neuropathic pain demonstrate that peripheral and central neuropathic pain are distinguished not only by the anatomical location of the lesion or dysfunction, but they also demonstrate that peripheral and central neuropathic pain can be distinguished by its mechanisms (McQuay, supra). Consequently, there is no clear relation between drug action mechanism and the effect in distinct pain conditions or for single drug classes and different pain conditions (Sindrup S H, Jensen T S, Pain 1999, 83:389-400).

Common analgesics like opioids and non-steroidal anti-inflammatory drugs (NSAIDs) improve only insufficiently chronic abnormal pain syndromes as peripheral and central neuropathic pain due to insufficient efficacy and/or dose-limiting side effects. In the search for alternative treatment regimes to produce satisfactory and sustained pain relief, corticosteroids, conduction blockade, glycerol, anti-convulsants, anti-arrhythmics, antidepressants, local anesthetics, topical agents such as capsaicin, gangliosides and electro-stimulation have been tried, but only a subset of patients with neuropathic pain respond to such treatments and typically, significant pain remains even in these responders. The critical issue with current therapies is the therapeutic window; a particular treatment might have potential for efficacy but the patients are not 'treated to effect' because of limiting side effects upon dose escalation.

Central neuropathic pain is a form of neuropathic pain which is a particularly difficult form to be treated (Yezierski and Burchiel, 2002). Due to lesions in the spinothalamocortical pathways, ectopic neuronal discharges can occur in different neurons of the spinal cord and brain. Hyperexcitability in damaged areas of the central nervous system plays a major role in the development of central neuropathic pain. Patients with central neuropathic pain almost always have stimulus-independent pain. In addition, in the case of spinal cord injury, for example, stimulus-dependent pain may be present, usually because skin areas or viscera below the lesions are allodynic. Thus, partial spinal lesions may tend to produce pain to a greater extent than do complete lesions.

Other accepted forms of central neuropathic pain or diseases associated with central neuropathic pain exist. Examples include inflammatory CNS diseases such as multiple sclerosis, myelitis or syphilis, ischemia, hemorrhages or asteriovenous malformations (e.g. post-stroke neuropathic pain) located in the thalamus, spinothalamic pathway or thalamocortical projections, and syrnigomyelia (Koltzenburg, Pain 2002—An Updated Review: Refresher Course Syllabus; IASP Press, Seattle, 2002).

$Na^+$-channels are central to the generation of action potentials in all excitable cells such as neurons and myocytes. As such they play key roles in a variety of disease states such as pain (See, Waxman, S. G., S. Dib-Hajj, et al. (1999) "Sodium channels and pain" Proc Natl Acad Sci USA 96(14): 7635-9 and Waxman, S. G., T. R. Cummins, et al. (2000) "Voltage-gated sodium channels and the molecular pathogenesis of pain: a review" J Rehabil Res Dev 37(5): 517-28). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" FEBS Lett 259(1): 213-6).

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists include TTX, lidocaine (See Mao, J. and L. L. Chen (2000) "Systemic lidocaine for neuropathic pain relief" Pain 87(1): 7-17.) bupivacaine, carbamazepine, mexilitene, phenytoin (See Jensen, T. S. (2002) "Anticonvulsants in neuropathic pain: rationale and clinical evidence" Eur J Pain 6 (Suppl A):

61-8), and lamotrigine (See Rozen, T. D. (2001) "Antiepileptic drugs in the management of cluster headache and trigeminal neuralgia" Headache 41 Suppl 1:S25-32 and Jensen, T. S. (2002). However, side effects include dizziness, somnolence, nausea and vomiting (See Tremont-Lukats, I. W., C. Megeff, and M. M. Backonja (2000) "Anticonvulsants for neuropathic pain syndromes: mechanisms of action and place in therapy" Drugs 60:1029-1052) that limit the utility of these known NaV antagonists for the treatment of pain. These side effects are thought to result at least in part from the block of multiple NaV subtypes. An agent that inhibits the NaV1.8 channel selectively would provide a much great therapeutic window than these non-selective, known NaV antagonists.

The detection and transmission of nociceptive stimuli is mediated by small sensory neurons. Immunohistochemical, in-situ hybridization and electrophysiology experiments have all shown that the sodium channel NaV1.8 is selectively localized to the small sensory neurons of the dorsal root ganglion and trigeminal ganglion (see Akopian, A. N., L. Sivilotti, et al. (1996) "A tetrodotoxin-resistant voltage-gated sodium channel expressed by sensory neurons" Nature 379 (6562): 257-62.). After experimental nerve injury, immunohistochemical data demonstrated an accumulation of Nav1.8 at the site of nerve injury, concomitant with an upregulation in TTX-resistant sodium current, consistent with NaV1.8 as a mechanism underlying hyperalgesia (see Gold, M. S., D. Weinreich, et al. (2003) "Redistribution of Nav1.8 in uninjured axons enables neuropathic pain" J. Neurosci. 23:158-166). Attenuation of NaV1.8 expression with antisense oligodeoxynucleotides administered by intrathecal injection prevented experimental nerve-injury induced redistribution of Nav1.8 in the sciatic nerve and reversed neuropathic pain (tactile and thermal hyperalgesia), demonstrating a causal role of Nav1.8 in nerve-injury induced pain (see also Lai, J., M. S. Gold, et al. (2002) "Inhibition of neuropathic pain by decreased expression of the tetrodotoxin-resistant sodium channel, NaV1.8" Pain 95(1-2): 143-52, and Lai, J., J. C. Hunter, et al. (2000) "Blockade of neuropathic pain by antisense targeting of tetrodotoxin-resistant sodium channels in sensory neurons" Methods Enzymol 314: 201-13.). In inflammatory pain models, intrathecal administration of antisense oligodeoxynucleotides against NaV1.8 resulted in a significant reduction in $PGE_2$-induced hyperalgesia (see Khasar, S. G., M. S. Gold, et al. (1998) "A tetrodotoxin-resistant sodium current mediates inflammatory pain in the rat" Neurosci Lett 256(1): 17-20) and in CFA (complete Freund's adjuvant)—induced hyperalgesia (Porreca, F., J. Lai, et al. (1999) "A comparison of the potential role of the tetrodotoxin-insensitive sodium channels, PN3/SNS and NaN/SNS2, in rat models of chronic pain" Proc. Nat'l. Acad. Sci. 96: 7640-7644). In addition, in a rat model of visceral pain, induced by intravesical infusion of acetic acid, bladder hyperactivity was reduced by intrathecal injection of antisense oligodeoxynucleotides against NaV1.8, showing that Nav1.8 contributes to the activation of sensory nerves in visceral pain (Yoshimura, N., S. Seki, et al. (2001) "The involvement of the tetrodotoxin-resistant sodium channel Nav1.8 (PN3/SNS) in a rat model of visceral pain" J. Neurosci. 21: 8690-8696).

Taken together, these data support a role for NaV1.8 in the detection and transmission of inflammatory and neuropathic pain.

Recently, double-stranded RNA molecules (dsRNA) have been shown to block gene expression in a highly conserved regulatory mechanism known as RNA interference (RNAi). WO 99/32619 (Fire et al.) discloses the use of a dsRNA of at least 25 nucleotides in length to inhibit the expression of the Nav1.8 gene in *C. elegans*. dsRNA has also been shown to degrade target RNA in other organisms, including plants (see, e.g., WO 99/53050, Waterhouse et al.; and WO 99/61631, Heifetz et al0.), *Drosophila* (see, e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

Despite significant advances in the field of RNAi and advances in the treatment of pain, there remains a need for an agent that can selectively and efficiently silence the Nav1.8 gene using the cell's own RNAi machinery that has both high biological activity and in vivo stability, and that can effectively inhibit expression of a target Nav1.8 gene for use in treating pain.

SUMMARY OF THE INVENTION

The invention provides double-stranded ribonucleic acid (dsRNA), as well as compositions and methods for inhibiting the expression of the Nav1.8 gene in a cell or mammal using such dsRNA. The invention also provides compositions and methods for treating pathological conditions and diseases caused by the expression of the Nav1.8 gene, such as in the propagation of pain signals in neuropathic and inflammatory pain. The dsRNA of the invention comprises an RNA strand (the antisense strand) having a region which is less than 30 nucleotides in length and is substantially complementary to at least part of an mRNA transcript of the Nav1.8 gene.

In one embodiment, the invention provides double-stranded ribonucleic acid (dsRNA) molecules for inhibiting the expression of the Nav1.8 gene. The dsRNA comprises at least two sequences that are complementary to each other. The dsRNA comprises a sense strand comprising a first sequence and an antisense strand comprising a second sequence. The antisense strand comprises a nucleotide sequence which is substantially complementary to at least part of an mRNA encoding Nav1.8, and the region of complementarity is less than 30 nucleotides in length. The dsRNA, upon contacting with a cell expressing the Nav1.8, inhibits the expression of the Nav1.8 gene by at least 20%.

For example, the dsRNA molecules of the invention can be comprised of a first sequence of the dsRNA that is selected from the group consisting of the sense sequences of Tables 1, 4 and 6 and the second sequence is selected from the group consisting of the antisense sequences of Tables 1, 4 and 6. The dsRNA molecules of the invention can be comprised of naturally occurring nucleotides or can be comprised of at least one modified nucleotide, such as a 2'-O-methyl modified nucleotide, a nucleotide comprising a 5'-phosphorothioate group, and a terminal nucleotide linked to a cholesteryl derivative or dodecanoic acid bisdecylamide group. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Preferably, the first sequence of said dsRNA is selected from the group consisting of the sense sequences of Tables 1, 4 and 6 and the second sequence is selected from the group consisting of the antisense sequences of Tables 1, 4 and 6.

In another embodiment, the invention provides a cell comprising one of the dsRNAs of the invention. The cell is preferably a mammalian cell, such as a human cell.

In another embodiment, the invention provides a pharmaceutical composition for inhibiting the expression of the Nav1.8 gene in an organism, comprising one or more of the dsRNA of the invention and a pharmaceutically acceptable carrier.

In another embodiment, the invention provides a method for inhibiting the expression of the Nav1.8 gene in a cell, comprising the following steps:
(a) introducing into the cell a double-stranded ribonucleic acid (dsRNA), wherein the dsRNA comprises at least two sequences that are complementary to each other. The dsRNA comprises a sense strand comprising a first sequence and an antisense strand comprising a second sequence. The antisense strand comprises a region of complementarity which is substantially complementary to at least a part of an mRNA encoding Nav1.8, and wherein the region of complementarity is less than 30 nucleotides in length and wherein the dsRNA, upon contact with a cell expressing the Nav1.8, inhibits expression of the Nav1.8 gene by at least 20%; and
(b) maintaining the cell produced in step (a) for a time sufficient to obtain degradation of the mRNA transcript of the Nav1.8 gene, thereby inhibiting expression of the Nav1.8 gene in the cell.

In another embodiment, the invention provides methods for treating, preventing or managing pain comprising administering to a patient in need of such treatment, prevention or management a therapeutically or prophylactically effective amount of one or more of the dsRNAs of the invention.

In another embodiment, the invention provides vectors for inhibiting the expression of the Nav1.8 gene in a cell, comprising a regulatory sequence operably linked to a nucleotide sequence that encodes at least one strand of one of the dsRNA of the invention.

In another embodiment, the invention provides a cell comprising a vector for inhibiting the expression of the Nav1.8 gene in a cell. The vector comprises a regulatory sequence operably linked to a nucleotide sequence that encodes at least one strand of one of the dsRNA of the invention.

DETAILED DESCRIPTION OF THE INVENTION

Figure 1:
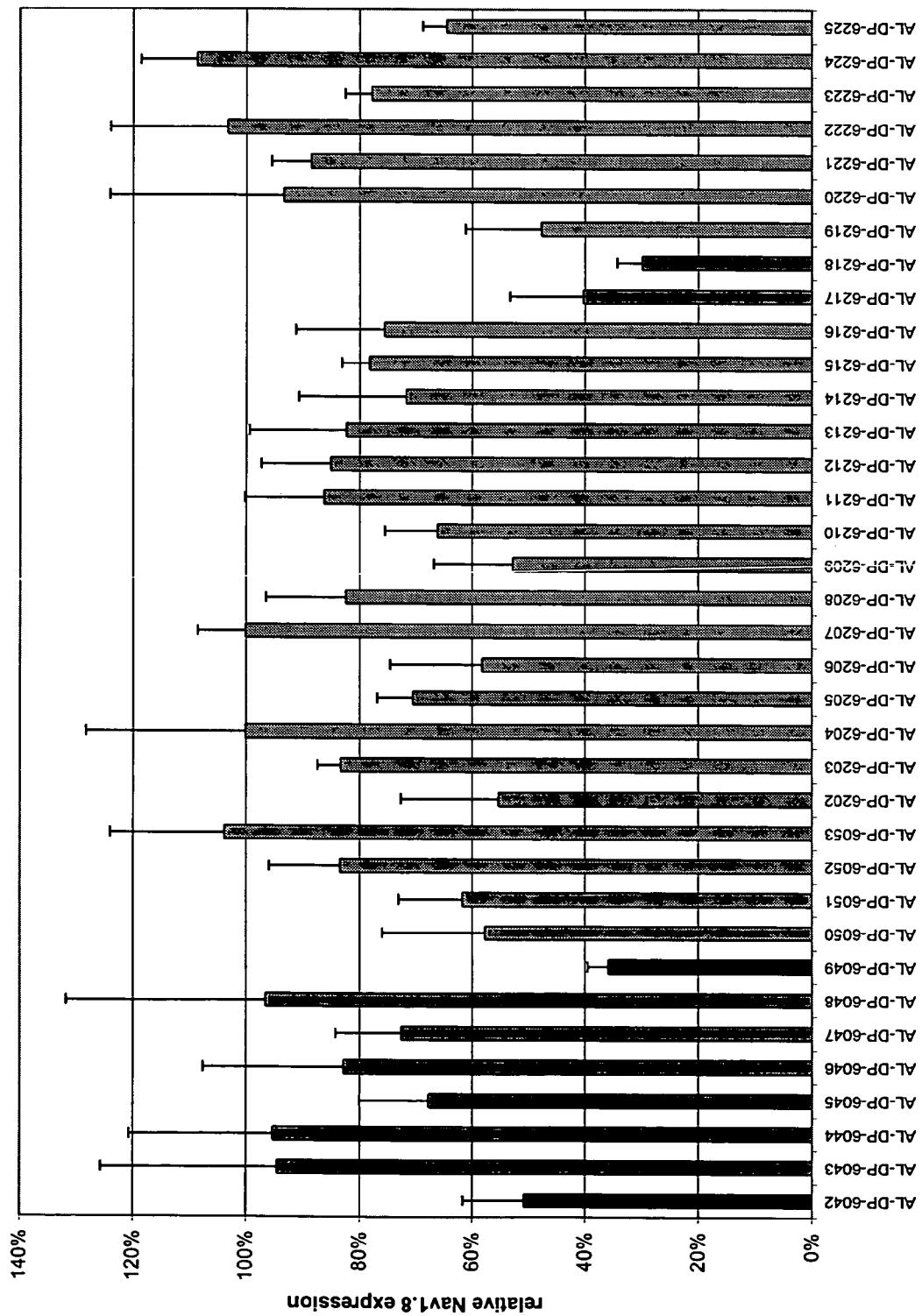
FIG. 1. In vitro activity of the dsRNAs provided in Table 1 against mRNA expression of transfected human Nav1.8 in Cos-7 cells.

The invention provides double-stranded ribonucleic acid (dsRNA), as well as compositions and methods for inhibiting the expression of the Nav1.8 gene in a cell or mammal using the dsRNA. The invention also provides compositions and methods for treating pathological conditions and diseases in a mammal caused by the expression of the Nav1.8 gene using dsRNA. dsRNA directs the sequence-specific degradation of mRNA through a process known as RNA interference (RNAi). The process occurs in a wide variety of organisms, including mammals and other vertebrates.

The dsRNA of the invention comprises an RNA strand (the antisense strand) having a region which is less than 30 nucleotides in length and which is substantially complementary to at least part of an mRNA transcript of the Nav1.8 gene. The use of these dsRNAs enables the targeted degradation of mRNAs of genes that are implicated in pain response in mammals. Using cell-based and animal assays, the present inventors have demonstrated that very low dosages of these dsRNA can specifically and efficiently mediate RNAi, resulting in significant inhibition of expression of the Nav1.8 gene. Thus, the methods and compositions of the invention comprising these dsRNAs are useful for treating pain.

The following detailed description discloses how to make and use the dsRNA and compositions containing dsRNA to inhibit the expression of a target Nav1.8 gene, as well as compositions and methods for treating diseases and disorders caused by the expression of Nav1.8, such as neuropathic and inflammatory pain. The pharmaceutical compositions of the invention comprise a dsRNA having an antisense strand comprising a region of complementarity which is less than 30 nucleotides in length and is substantially complementary to at least part of an RNA transcript of the Nav1.8 gene, together with a pharmaceutically acceptable carrier.

Accordingly, certain aspects of the invention provide pharmaceutical compositions comprising the dsRNA of the invention together with a pharmaceutically acceptable carrier, methods of using the compositions to inhibit expression of the Nav1.8 gene, and methods of using the pharmaceutical compositions to treat diseases caused by expression of the Nav1.8 gene.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

By "Nav1.8" as used herein is meant, any Nav1.8 protein, peptide, or polypeptide associated with the development or maintenance of an ion channel. The terms "Nav1.8" also refer to nucleic acid sequences encoding any Nav1.8 protein, peptide, or polypeptide. For the Examples, the Nav1.8 mRNA sequences used were human (NM_006514), mouse (NM_009134), rat (NM_017247) and dog (NM001003203) mRNA sequences.

As used herein, "target sequence" refers to a contiguous portion of the nucleotide sequence of an mRNA molecule formed during the transcription of the Nav1.8 gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but preferably not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding Nav1.8). For example, a polynucleotide is complementary to at least a part of a Nav1.8 mRNA if the sequence is substantially complementary to a non-interrupted portion of an mRNA encoding Nav1.8.

The term "double-stranded RNA" or "dsRNA", as used herein, refers to a ribonucleic acid molecule, or complex of ribonucleic acid molecules, having a duplex structure comprising two anti-parallel and substantially complementary, as defined above, nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. The maximum number of base pairs is the number of nucleotides in the shortest strand of the dsRNA. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are preferably in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of", in as far as they refer to the Nav1.8 gene, herein refer to the at least partial suppression of the expression of the Nav1.8 gene, as manifested by a reduction of the amount of mRNA transcribed from the Nav1.8 gene which may be isolated from a first cell or group of cells in which the Nav1.8 gene is transcribed and which has or have been treated such that the expression of the Nav1.8 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to Nav1.8 gene transcription, e.g. the amount of protein encoded by the Nav1.8 gene which is secreted by a cell, or the number of cells displaying a certain phenotype, e.g apoptosis. In principle, Nav1.8 gene silencing may be determined in any cell expressing the target, either constitutively or by genomic engineering, and by any appropriate assay. However, when a reference is needed in order to determine whether a given siRNA inhibits the expression of the Nav1.8 gene by a certain degree and therefore is encompassed by the instant invention, the assay provided in the Examples below shall serve as such reference.

For example, in certain instances, expression of the Nav1.8 gene is suppressed by at least about 20%, 25%, 35%, or 50% by administration of the double-stranded oligonucleotide of the invention. In a preferred embodiment, the Nav1.8 gene is suppressed by at least about 60%, 70%, or 80% by administration of the double-stranded oligonucleotide of the invention. In a more preferred embodiment, the Nav1.8 gene is suppressed by at least about 85%, 90%, or 95% by administration of the double-stranded oligonucleotide of the invention. In a most preferred embodiment, the Nav1.8 gene is suppressed by at least about 98%, 99% or more by administration of the double-stranded oligonucleotide of the invention.

The terms "treat", "treatment", and the like, refer to relief from or alleviation of the perception of pain, including the relief from or alleviation of the intensity and/or duration of a pain (e.g., burning sensation, tingling, electric-shock-like feelings, etc.) experienced by a subject in response to a given stimulus (e.g., pressure, tissue injury, cold temperature, etc.). Relief from or alleviation of the perception of pain can be any detectable decrease in the intensity or duration of pain. Treatment can occur in a subject (e.g., a human or companion animal) suffering from a pain condition or having one or more symptoms of a pain-related disorder that can be treated according to the present invention, or in an animal model of pain, such as the SNL rat model of neuropathic pain or CFA rat model of chronic pain described herein, or another animal model of pain. In the context of the present invention insofar as it relates to any of the other conditions recited herein below (other than pain), the terms "treat", "treatment", and the like mean to relieve or alleviate at least one symptom associated with such condition, or to slow or reverse the progression of such condition.

As used herein, the phrases "therapeutically effective amount" and "prophylactically effective amount" refer to an amount that provides a therapeutic benefit in the treatment, prevention, or management of pain or an overt symptom of pain. The specific amount that is therapeutically effective can be readily determined by ordinary medical practitioner, and may vary depending on factors known in the art, such as, e.g. the type of pain, the patient's history and age, the stage of pain, and the administration of other anti-pain agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. Double-Stranded Ribonucleic Acid (dsRNA)

In one embodiment, the invention provides double-stranded ribonucleic acid (dsRNA) molecules for inhibiting the expression of the Nav1.8 gene in a cell or mammal, wherein the dsRNA comprises an antisense strand comprising a region of complementarity which is complementary to at least a part of an mRNA formed in the expression of the Nav1.8 gene, and wherein the region of complementarity is less than 30 nucleotides in length and wherein said dsRNA, upon contact with a cell expressing said Nav1.8 gene, inhibits the expression of said Nav1.8 gene by at least 20%. The dsRNA comprises two RNA strands that are sufficiently complementary to hybridize to form a duplex structure. One strand of the dsRNA (the antisense strand) comprises a region of complementarity that is substantially complementary, and preferably fully complementary, to a target sequence, derived from the sequence of an mRNA formed during the expression of the Nav1.8 gene, the other strand (the sense strand) comprises a region which is complementary to the antisense strand, such that the two strands hybridize and form a duplex structure when combined under suitable conditions. Preferably, the duplex structure is between 15 and 30, more preferably between 18 and 25, yet more preferably between 19 and 24, and most preferably between 21 and 23 base pairs in length. Similarly, the region of complementarity to the target sequence is between 15 and 30, more preferably between 18 and 25, yet more preferably between 19 and 24, and most preferably between 21 and 23 nucleotides in length. The dsRNA of the invention may further comprise one or more single-stranded nucleotide overhang(s). The dsRNA can be synthesized by standard methods known in the art as further discussed below, e.g., by use of an automated DNA synthesizer, such as are commercially available from, for example, Biosearch, Applied Biosystems, Inc. In a preferred embodiment, the Nav1.8 gene is the human Nav1.8 gene. In specific embodiments, the antisense strand of the dsRNA comprises the antisense sequences of Tables 1, 4 and 6 and the second sequence is selected from the group consisting of the sense sequences of Tables 1, 4 and 6.

In further embodiments, the dsRNA comprises at least one nucleotide sequence selected from the groups of sequences provided in Tables 1, 4 and 6. In other embodiments, the dsRNA comprises at least two sequences selected from this group, wherein one of the at least two sequences is complementary to another of the at least two sequences, and one of the at least two sequences is substantially complementary to a sequence of an mRNA generated in the expression of the Nav1.8 gene. Preferably, the dsRNA comprises two oligonucleotides, wherein one oligonucleotide is described by Tables 1, 4 and 6 and the second oligonucleotide is described by Tables 1, 4 and 6.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Tables 1, 4 and 6, the dsRNAs of the invention can comprise at least one strand of a length of minimally 21 nt. It can be reasonably expected that shorter dsRNAs comprising one of the sequences of Tables 1, 4 and 6 minus only a few nucleotides on one or both ends may be similarly effective as compared to the dsRNAs described above. Hence, dsRNAs comprising a partial sequence of at least 15, 16, 17, 18, 19, 20, or more contiguous nucleotides from one of the sequences of Tables 1, 4 and 6, and differing in their ability to inhibit the expression of the Nav1.8 gene in a FACS assay as described herein below by not more than 5, 10, 15, 20, 25, or 30% inhibition from a dsRNA comprising the full sequence, are contemplated by the invention.

The dsRNA of the invention can contain one or more mismatches to the target sequence. In a preferred embodiment, the dsRNA of the invention contains more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the Nav1.8 gene, the dsRNA preferably does not contain any mismatch within the central 13 nucleotides. The methods described within the invention can be used to determine whether a dsRNA containing a mismatch to a target sequence is effective in inhibiting the expression of the Nav1.8 gene. Consideration of the efficacy of dsRNAs with mismatches in inhibiting expression of the Nav1.8 gene is important, especially if the particular region of complementarity in the Nav1.8 gene is known to have polymorphic sequence variation within the population.

In one embodiment, at least one end of the dsRNA has a single-stranded nucleotide overhang of 1 to 4, preferably 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Preferably, the single-stranded overhang is located at the 3'-terminal end of the antisense strand or, alternatively, at the 3'-terminal end of the sense strand. The dsRNA may also have a blunt end, preferably located at the 5'-end of the antisense strand. Such dsRNAs have improved stability and inhibitory activity, thus allowing administration at low dosages, i.e., less than 5 mg/kg body weight of the recipient per day. Preferably, the antisense strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Inc., New York, N.Y., USA, which is hereby incorporated herein by reference. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. Preferably, the chemical groups that can be used to modify the dsRNA include, without limitation, methylene blue; bifunctional groups, preferably bis-(2-chloroethyl)amine; N-acetyl-N'-(p-glyoxylbenzoyl)cystamine; 4-thiouracil; and psoralen. In one preferred embodiment, the linker is a hexa-ethylene glycol linker. In this case, the dsRNA are produced by solid phase synthesis and the hexa-ethylene glycol linker is incorporated according to standard methods (e.g., Williams, D. J., and K. B. Hall, *Biochem*. (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is preferably formed by triple-helix bonds. Table 1 provides examples of modified RNAi agents of the invention.

In certain embodiments, a chemical bond may be formed by means of one or several bonding groups, wherein such bonding groups are preferably poly-(oxyphosphinicooxy-1, 3-propandiol)- and/or polyethylene glycol chains. In other embodiments, a chemical bond may also be formed by means of purine analogs introduced into the double-stranded structure instead of purines. In further embodiments, a chemical bond may be formed by azabenzene units introduced into the double-stranded structure. In still further embodiments, a chemical bond may be formed by branched nucleotide analogs instead of nucleotides introduced into the double-stranded structure. In certain embodiments, a chemical bond may be induced by ultraviolet light.

In yet another embodiment, the nucleotides at one or both of the two single strands may be modified to prevent or inhibit the activation of cellular enzymes, such as, for example, without limitation, certain nucleases. Techniques for inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate (see, e.g., Wagner, *Nat. Med.* (1995) 1:1116-8). Thus, at least one 2'-hydroxyl group of the nucleotides on a dsRNA is replaced by a chemical group, preferably by a 2'-fluoro or a 2'-O-methyl group. Also, at least one nucleotide may be modified to form a locked nucleotide. Such locked nucleotide contains a methylene or ethylene bridge that connects the 2'-oxygen of ribose with the 4'-carbon of ribose. Oligonucleotides containing the locked nucleotide are described in Koshkin, A. A., et al., *Tetrahedron* (1998), 54: 3607-3630) and Obika, S. et al., *Tetrahedron Lett.* (1998), 39: 5401-5404). Introduction of a locked nucleotide into an oligonucleotide improves the affinity for complementary sequences and increases the melting temperature by several degrees (Braasch, D. A. and D. R. Corey, *Chem. Biol.* (2001), 8:1-7).

Conjugating a ligand to a dsRNA can enhance its cellular absorption. In certain instances, a hydrophobic ligand is conjugated to the dsRNA to facilitate direct permeation of the cellular membrane. Alternatively, the ligand conjugated to the dsRNA is a substrate for receptor-mediated endocytosis. These approaches have been used to facilitate cell permeation of antisense oligonucleotides. For example, cholesterol has been conjugated to various antisense oligonucleotides resulting in compounds that are substantially more active compared to their non-conjugated analogs. See M. Manoharan *Antisense & Nucleic Acid Drug Development* 2002, 12, 103. Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptor-mediated endocytosis. Li and coworkers report that attachment of folic acid to the 3'-terminus of an oligonucleotide resulted in an 8-fold increase in cellular uptake of the oligonucleotide. Li, S.; Deshmukh, H. M.; Huang, L. *Pharm. Res.* 1998, 15, 1540. Other ligands that have been conjugated to oligonucleotides include polyethylene glycols, carbohydrate clusters, cross-linking agents, porphyrin conjugates, and delivery peptides.

In certain instances, conjugation of a cationic ligand to oligonucleotides often results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See M. Manoharan *Antisense & Nucleic Acid Drug Development* 2002, 12, 103 and references therein.

The ligand-conjugated dsRNA of the invention may be synthesized by the use of a dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. The methods of the invention facilitate the synthesis of ligand-conjugated dsRNA by the use of; in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the invention via reaction of a selected serum-binding ligand with a linking moiety located on the 5' position of a nucleoside or oligonucleotide. In certain instances, an dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The dsRNA used in the conjugates of the invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

Teachings regarding the synthesis of particular modified oligonucleotides may be found in the following U.S. patents: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

In the ligand-conjugated dsRNA and ligand-molecule bearing sequence-specific linked nucleosides of the invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

The incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-O-methyl, 2'-O-ethyl, 2'-O-propyl, 2'-O-aminoalkyl, 2'-O-allyl or 2'-deoxy-2'-fluoro group.

In some preferred embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In a preferred embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

In one preferred embodiment of the methods of the invention, the preparation of ligand conjugated oligonucleotides commences with the selection of appropriate precursor molecules upon which to construct the ligand molecule. Typically, the precursor is an appropriately-protected derivative of the commonly-used nucleosides. For example, the synthetic precursors for the synthesis of the ligand-conjugated oligonucleotides of the invention include, but are not limited to, 2'-aminoalkoxy-5'-ODMT-nucleosides, 2'-6-aminoalkylamino-5'-ODMT-nucleosides, 5'-6-aminoalkoxy-2'-deoxy-nucleosides, 5'-6-aminoalkoxy-2-protected-nucleosides, 3'-6-aminoalkoxy-5'-ODMT-nucleosides, and 3'-aminoalkylamino-5'-ODMT-nucleosides that may be protected in the nucleobase portion of the molecule. Methods for the synthesis of such amino-linked protected nucleoside precursors are known to those of ordinary skill in the art.

In many cases, protecting groups are used during the preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron*, 1992, 48:2223-2311). Further hydroxyl protecting groups, as well as other representative protecting groups, are disclosed in Greene and Wuts, *Protective Groups in Organic Synthesis*, Chapter 2, 2d ed., John Wiley & Sons, New York, 1991, and *Oligonucleotides And Analogues A Practical Approach*, Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides*, S. Udenfriend, J. Meienhofer, Eds., Academic Press, Orlando, 1987, volume 9, p. 1) and various substituted sulfonylethyl carbamates exemplified by the Nsc group (Samukov et al., *Tetrahedron Lett.*, 1994, 35:7821; Verhart and Tesser, *Rec. Trav. Chim. Pays-Bas*, 1987, 107:621).

Additional amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the invention.

Many solid supports are commercially available and one of ordinary skill in the art can readily select a solid support to be used in the solid-phase synthesis steps. In certain embodiments, a universal support is used. A universal support allows for preparation of oligonucleotides having unusual or modified nucleotides located at the 3'-terminus of the oligonucleotide. Universal Support 500 and Universal Support II are universal supports that are commercially available from Glen Research, 22825 Davis Drive, Sterling, Va. For further details about universal supports see Scott et al., *Innovations and Perspectives in solid-phase Synthesis, 3rd International Symposium*, 1994, Ed. Roger Epton, Mayflower Worldwide, 115-124]; Azhayev, A. V. *Tetrahedron* 1999, 55, 787-800; and Azhayev and Antopolsky *Tetrahedron* 2001, 57, 4977-4986. In addition, it has been reported that the oligonucleotide can be cleaved from the universal support under milder reaction conditions when oligonucleotide is bonded to the solid support via a syn-1,2-acetoxyphosphate group which more readily undergoes basic hydrolysis. See Guzaev, A. I.; Manoharan, M. *J. Am. Chem. Soc.* 2003, 125, 2380.

The nucleosides are linked by phosphorus-containing or non-phosphorus-containing covalent internucleoside linkages. For the purposes of identification, such conjugated nucleosides can be characterized as ligand-bearing nucleosides or ligand-nucleoside conjugates. The linked nucleosides having an aralkyl ligand conjugated to a nucleoside within their sequence will demonstrate enhanced dsRNA activity when compared to like dsRNA compounds that are not conjugated.

The aralkyl-ligand-conjugated oligonucleotides of the invention also include conjugates of oligonucleotides and linked nucleosides wherein the ligand is attached directly to the nucleoside or nucleotide without the intermediacy of a linker group. The ligand may preferably be attached, via linking groups, at a carboxyl, amino or oxo group of the ligand. Typical linking groups may be ester, amide or carbamate groups.

Specific examples of preferred modified oligonucleotides envisioned for use in the ligand-conjugated oligonucleotides of the invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. For the purposes of the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified. Conversely, more than one modifications may be incorporated in a single dsRNA compound or even in a single nucleotide thereof.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States Patents relating to the preparation of the above phosphorus-atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents relating to the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497.

Some preferred embodiments of the invention employ oligonucleotides with phosphorothioate linkages and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The oligonucleotides employed in the ligand-conjugated oligonucleotides of the invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further nucleobases include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligonucleotides of the invention. These include 5-substituted pyrimidines, 6-azapyrimidines and N-2, N-6 and 0-6 substituted purines, including 2-aminopropyladenine, 5-propynyluracil and 5-propynylcytosine. 5-Methylcytosine substitutions have been shown to increase nucleic acid duplex stability by 0.6-1.2° C. (Id., pages 276-278) and are presently preferred base substitutions, even more particularly when combined with 2'-methoxyethyl sugar modifications.

Representative United States patents relating to the preparation of certain of the above-noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,808,027; all of which are hereby incorporated by reference.

In certain embodiments, the oligonucleotides employed in the ligand-conjugated oligonucleotides of the invention may additionally or alternatively comprise one or more substituted sugar moieties. Preferred oligonucleotides comprise one of the following at the 2' position: OH; F; O-, S-, or N-alkyl, O-, S-, or N-alkenyl, or O, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2 CH_3$, $ONO_2$, $NO_2$, $N_3$, $NH_2$, heterocycloalkyl heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy [2'-O—$CH_2CH_2OCH_3$, also known as 2'-O-(2-methoxyethyl) or 2'-MOE] (Martin et al., *Helv. Chim. Acta,* 1995, 78, 486), i.e., an alkoxyalkoxy group. A further preferred modification includes 2'-dimethylaminooxyethoxy, i.e., a $O(CH_2)_2ON(CH_3)_2$ group, also known as 2'-DMAOE, as described in U.S. Pat. No. 6,127,533, filed on Jan. 30, 1998, the contents of which are incorporated by reference.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides.

As used herein, the term "sugar substituent group" or "2'-substituent group" includes groups attached to the 2'-position of the ribofuranosyl moiety with or without an oxygen atom. Sugar substituent groups include, but are not limited to, fluoro, O-alkyl, O-alkylamino, O-alkylalkoxy, protected O-alkylamino, O-alkylaminoalkyl, O-alkyl imidazole and polyethers of the formula $(O-alkyl)_m$, wherein m is 1 to about 10. Preferred among these polyethers are linear and cyclic polyethylene glycols (PEGS), and (PEG)-containing groups, such as crown ethers and those which are disclosed by Ouchi et al. (Drug Design and Discovery 1992, 9:93); Ravasio et al. (*J. Org. Chem.* 1991, 56:4329); and Delgardo et. al. (*Critical Reviews in Therapeutic Drug Carrier Systems* 1992, 9:249), each of which is hereby incorporated by reference in its entirety. Further sugar modifications are disclosed by Cook (*Anti-pain Drug Design,* 1991, 6:585-607). Fluoro, O-alkyl, O-alkylamino, O-alkyl imidazole, O-alkylaminoalkyl, and alkyl amino substitution is described in U.S. Pat. No. 6,166, 197, entitled "Oligomeric Compounds having Pyrimidine Nucleotide(s) with 2' and 5' Substitutions," hereby incorporated by reference in its entirety.

Additional sugar substituent groups amenable to the invention include 2'-SR and 2'-$NR_2$ groups, wherein each R is, independently, hydrogen, a protecting group or substituted or unsubstituted alkyl, alkenyl, or alkynyl. 2'-SR Nucleosides are disclosed in U.S. Pat. No. 5,670,633, hereby incorporated by reference in its entirety. The incorporation of 2'-SR monomer synthons is disclosed by Hamm et al. (*J. Org. Chem.,* 1997, 62:3415-3420). 2'-NR nucleosides are disclosed by Goettingen, M., *J. Org. Chem.,* 1996, 61, 6273-6281; and Polushin et al., *Tetrahedron Lett.,* 1996, 37, 3227-3230. Further representative 2'-substituent groups amenable to the invention include those having one of formula I or II:

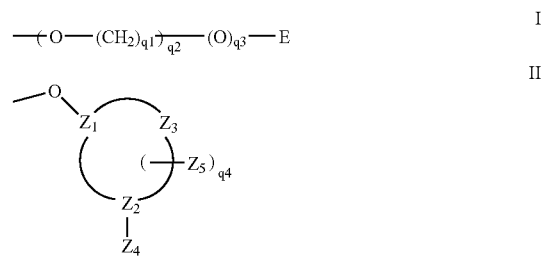

wherein,

E is $C_1$-$C_{10}$ alkyl, $N(Q_3)(Q_4)$ or $N=C(Q_3)(Q_4)$; each $Q_3$ and $Q_4$ is, independently, H, $C_1$-$C_{10}$ alkyl, dialkylaminoalkyl, a nitrogen protecting group, a tethered or untethered conjugate group, a linker to a solid support; or $Q_3$ and $Q_4$, together, form a nitrogen protecting group or a ring structure optionally including at least one additional heteroatom selected from N and O;

$q_1$ is an integer from 1 to 10;
$q_2$ is an integer from 1 to 10;
$q_3$ is 0 or 1;
$q_4$ is 0, 1 or 2;
each $Z_1$, $Z_2$ and $Z_3$ is, independently, $C_4$-$C_7$ cycloalkyl, $C_5$-$C_{14}$ aryl or $C_3$-$C_{15}$ heterocyclyl, wherein the heteroatom in said heterocyclyl group is selected from oxygen, nitrogen and sulfur;
$Z_4$ is $OM_1$, $SM_1$, or $N(M_1)_2$; each $M_1$ is, independently, H, $C_1$-$C_8$ alkyl, $C_1$-$C_8$ haloalkyl, $C(=NH)N(H)M_2$, $C(=O)N(H)M_2$ or $OC(=O)N(H)M_2$; $M_2$ is H or $C_1$-$C_8$ alkyl; and
$Z_5$ is $C_1$-$C_{10}$ alkyl, $C_1$-$C_{10}$ haloalkyl, $C_2$-$C_{10}$ alkenyl, $C_2$-$C_{10}$ alkynyl, $C_6$-$C_{14}$ aryl, $N(Q_3)(Q_4)$, $OQ_3$, halo, $SQ_3$ or CN.

Representative 2'-O-sugar substituent groups of formula 1 are disclosed in U.S. Pat. No. 6,172,209, entitled "Capped 2'-Oxyethoxy Oligonucleotides," hereby incorporated by reference in its entirety. Representative cyclic 2'-O-sugar substituent groups of formula II are disclosed in U.S. Pat. No. 6,271,358, entitled "RNA Targeted 2'-Modified Oligonucleotides that are Conformationally Preorganized," hereby incorporated by reference in its entirety.

Sugars having O-substitutions on the ribosyl ring are also amenable to the invention. Representative substitutions for ring O include, but are not limited to, S, $CH_2$, CHF, and $CF_2$. See, e.g., Secrist et al., Abstract 21, *Program & Abstracts, Tenth International Roundtable, Nucleosides, Nucleotides and their Biological Applications*, Park City, Utah, Sep. 16-20, 1992.

Oligonucleotides may also have sugar mimetics, such as cyclobutyl moieties, in place of the pentofuranosyl sugar. Representative United States patents relating to the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; 5,700,920; and 5,859,221, all of which are hereby incorporated by reference.

Additional modifications may also be made at other positions on the oligonucleotide, particularly the 3' position of the sugar on the 3' terminal nucleotide. For example, one additional modification of the ligand-conjugated oligonucleotides of the invention involves chemically linking to the oligonucleotide one or more additional non-ligand moieties or conjugates which enhance the activity, cellular distribution or cellular uptake of the oligonucleotide. Such moieties include but are not limited to lipid moieties, such as a cholesterol moiety (Letsinger et al., *Proc. Natl. Acad. Sci. USA,* 1989, 86, 6553), cholic acid (Manoharan et al., *Bioorg. Med. Chem. Lett.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651; Shea et al., *Nucl. Acids Res.,* 1990, 18, 3777), a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651), a palmityl moiety (Mishra et al., *Biochim. Biophys. Acta,* 1995, 1264, 229), or an octadecylamine or hexylaminocarbonyl-oxycholesterol moiety (Crooke et al., *J. Pharmacol. Exp. Ther.,* 1996, 277, 923).

Representative United States patents relating to the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941, each of which is herein incorporated by reference.

The invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., *Proc. Natl. Acad. Sci. USA,* 1989, 86:6553), cholic acid (Manoharan et al., *Bioorg. Med. Chem. Lett.,* 1994, 4:1053), a thioether, e.g., hexyl-S-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Alternatively, the molecule being conjugated may be converted into a building block, such as a phosphoramidite, via an alcohol group present in the molecule or by attachment of a linker bearing an alcohol group that may be phosphitylated.

Importantly, each of these approaches may be used for the synthesis of ligand conjugated oligonucleotides. Amino-linked oligonucleotides may be coupled directly with ligand via the use of coupling reagents or following activation of the ligand as an NHS or pentfluorophenolate ester. Ligand phosphoramidites may be synthesized via the attachment of an aminohexanol linker to one of the carboxyl groups followed by phosphitylation of the terminal alcohol functionality. Other linkers, such as cysteamine, may also be utilized for conjugation to a chloroacetyl linker present on a synthesized oligonucleotide.

III. Pharmaceutical Compositions Comprising dsRNA

In one embodiment, the invention provides pharmaceutical compositions comprising a dsRNA, as described herein, and a pharmaceutically acceptable carrier. The pharmaceutical composition comprising the dsRNA is useful for treating a disease or disorder associated with the expression or activity of the Nav1.8 gene, such as neuropathic or inflammatory pain.

In another embodiment, the invention provides pharmaceutical compositions comprising at least two dsRNAs, designed to target different regions of the Nav1.8 gene, and a pharmaceutically acceptable carrier. In this embodiment, the individual dsRNAs are prepared as described in the preceding section, which is incorporated by reference herein. One dsRNA can have a nucleotide sequence which is substantially complementary to at least one part of the Nav1.8 gene; additional dsRNAs are prepared, each of which has a nucleotide sequence that is substantially complementary to different part of the Nav1.8 gene. The multiple dsRNAs may be combined in the same pharmaceutical composition, or formulated separately. If formulated individually, the compositions containing the separate dsRNAs may comprise the same or different carriers, and may be administered using the same or different routes of administration. Moreover, the pharmaceutical compositions comprising the individual dsRNAs may be administered substantially simultaneously, sequentially, or at preset intervals throughout the day or treatment period.

The pharmaceutical compositions of the invention are administered in dosages sufficient to inhibit expression of the Nav1.8 gene. The present inventors have found that, because of their improved efficiency, compositions comprising the dsRNA of the invention can be administered at surprisingly low dosages. A maximum dosage of 5 mg dsRNA per kilogram body weight of recipient per day is sufficient to inhibit or completely suppress expression of the Nav1.8 gene, or alleviate chronic pain.

In general, a suitable dose of dsRNA will be in the range of 0.01 to 5.0 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. The pharmaceutical composition may be administered once daily, or the dsRNA may be administered as two, three, four, five, six or more sub-doses at appropriate intervals throughout the day or even using continuous infusion. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pain. Such models are used for in vivo testing of dsRNA, as well as for determining a therapeutically effective dose.

The pharmaceutical compositions encompassed by the invention may be administered by any means known in the art including, but not limited to oral or parenteral routes, including intravenous, intramuscular, intraperitoneal, epidural, intrathecal, intracerebroventricular, intraparenchymal (within the peripheral or central nervous system), subcutaneous, transdermal, intranasal, airway (aerosol), rectal, vaginal and topical (including buccal and sublingual) administration. In preferred embodiments, the pharmaceutical compositions are administered intrathecally by continuous infusion such as with a pump, or intrathecally by bolus injection. In other preferred embodiments, the pharmaceutical compositions are administered intravenously by continuous infusion such as with a pump, or intravenously by bolus injection.

For intrathecal, intracerebroventricular, intramuscular, intraparenchyrnal (within the peripheral or central nervous system), subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of dsRNA in the cells that express the Nav1.8 gene. Such substances include, for example, micellar structures, such as liposomes or capsids, as described below. Surprisingly, the present inventors have discovered that compositions containing only naked dsRNA and a physiologically acceptable solvent are taken-up by cells, where the dsRNA effectively inhibits expression of the Nav1.8 gene. Although microinjection, lipofection, viruses, viroids, capsids, capsoids, or other auxiliary agents are required to introduce dsRNA into cell cultures, surprisingly these methods and agents are not necessary for uptake of dsRNA in vivo. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

Using the small interfering RNA vectors previously described, the invention also provides devices, systems, and methods for delivery of small interfering RNA to target locations in the nervous system and or the brain. The envisioned route of delivery is through the use of implanted, indwelling, intrathecal, intracerebroventricular or intraparenchymal catheters that provide a means for injecting small volumes of fluid containing the dsRNA of the invention directly into local nerves or local brain tissue, or into bodily fluids surrounding these tissues. The proximal end of these catheters may be connected to an implanted, intrathecal or intracerebral access port surgically affixed to the patient's body or cranium, or to an implanted drug pump located in the patient's torso.

Alternatively, implantable delivery devices, such as an implantable pump may be employed. Examples of the delivery devices within the scope of the invention include the Model 8506 investigational device (by Medtronic, Inc. of Minneapolis, Minn.), which can be implanted subcutaneously in the body or on the cranium, and provides an access port through which therapeutic agents may be delivered to the nerves or brain. Delivery occurs through a stereotactically implanted polyurethane catheter. Two models of catheters that can function with the Model 8506 access port include the Model 8770 ventricular catheter by Medtronic, Inc., for delivery to the intracerebral ventricles, which is disclosed in U.S. Pat. No. 6,093,180, incorporated herein by reference, and the IPAI catheter by Medtronic, Inc., for delivery to the brain tissue itself (i.e., intraparenchymal delivery), disclosed in U.S. Ser. Nos. 09/540,444 and 09/625,751, which are incorporated herein by reference. The latter catheter has multiple outlets on its distal end to deliver the therapeutic agent to multiple sites along the catheter path. In addition to the aforementioned device, the delivery of the small interfering RNA vectors in accordance with the invention can be accomplished with a wide variety of devices, including but not limited to U.S. Pat. Nos. 5,735,814, 5,814,014, and 6,042,579, all of which are incorporated herein by reference. Using the teachings of the invention and those of skill in the art will recognize that these and other devices and systems may be suitable for delivery of small interfering RNA vectors for the treatment of pain in accordance with the invention.

In one such embodiment, the method further comprises the steps of implanting a pump outside the body or brain, the pump coupled to a proximal end of the catheter, and operating the pump to deliver the predetermined dosage of the at least one small interfering RNA or small interfering RNA vector through the discharge portion of the catheter. A further embodiment comprises the further step of periodically refreshing a supply of the at least one small interfering RNA or small interfering RNA vector to the pump outside said body or brain.

Thus, the invention includes the delivery of small interfering RNA vectors using an implantable pump and catheter, like that taught in U.S. Pat. No. 5,735,814 and 6,042,579, and further using a sensor as part of the infusion system to regulate the amount of small interfering RNA vectors delivered to the nerves or brain, like that taught in U.S. Pat. No. 5,814,014. Other devices and systems can be used in accordance with the method of the invention, for example, the devices and systems disclosed in U.S. Ser. No. 09/872,698 (filed Jun. 1, 2001) and U.S. Ser. No. 09/864,646 (filed May 23, 2001), which are incorporated herein by reference.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs of the invention can be administered in combination with other known agents effective in treatment of pain. In any event, the administering physician can adjust the amount and timing of dsRNA administration on the basis of results observed using standard measures of efficacy known in the art or described herein.

Methods for Treating Diseases Caused by Expression of the Nav1.8 Gene

In one embodiment, the invention provides a method for treating a subject having a pathological condition mediated by the expression of the Nav1.8 gene, such as neuropathic or inflammatory pain. In this embodiment, the dsRNA acts as a therapeutic agent for controlling the expression of the Nav1.8 protein. The method comprises administering a pharmaceutical composition of the invention to the patient (e.g., human), such that expression of the Nav1.8 gene is silenced. Because of their high specificity, the dsRNAs of the invention specifically target mRNAs of the Nav1.8 gene.

Pain

As used herein, the term "pain" is art recognized and includes a bodily sensation elicited by noxious chemical, mechanical, or thermal stimuli, in a subject, e.g., a mammal such as a human. The term "pain" includes chronic pain such as lower back pain; pain due to arthritis, e.g., osteoarthritis; joint pain, e.g., knee pain or carpal tunnel syndrome; myofascial pain, and neuropathic pain. The term "pain" further includes acute pain, such as pain associated with muscle strains and sprains; tooth pain; headaches; pain associated with surgery; and pain associated with various forms of tissue injury, e.g., inflammation, infection, and ischemia.

"Neuropathic pain" refers to pain caused by injury or disease of the central or peripheral nervous system. In contrast to the immediate (acute) pain caused by tissue injury, neuropathic pain can develop days or months after a traumatic injury. Neuropathic pain frequently is long lasting or chronic, and is not limited in duration to the period of tissue repair. Neuropathic pain can occur spontaneously, or as a result of stimulation that normally is not painful. Neuropathic pain is caused by aberrant somatosensory processing, and is associated with chronic sensory disturbances, including spontaneous pain, hyperalgesia (i.e., sensation of more pain than the stimulus would warrant) and allodynia (i.e., a condition in which ordinarily painless stimuli induce the experience of pain). Neuropathic pain includes, but is not limited to, pain caused by peripheral nerve trauma, viral infection, diabetes mellitus, chemotherapy, causalgia, plexus-avulsion, spinal cord injury, neuroma, limb amputation, vasculitis, nerve damage from surgery, nerve damage from chronic alcoholism, hypothyroidism, uremia, and vitamin deficiencies, among other causes. Neuropathic pain is one type of pain associated with cancer. Cancer pain can also be "nociceptive" or "mixed."

"Chronic pain" can be defined as pain lasting longer than three months (Bonica, Semin. Anesth. 1986, 5:82-99), and may be characterized by unrelenting persistent pain that is not fully amenable to routine pain control methods. Chronic pain includes, but is not limited to, inflammatory pain, post-operative pain, cancer pain, osteoarthritis pain associated with metastatic cancer, chemotherapy-induced pain, trigeminal neuralgia, acute herpetic and post-herpetic neuralgia, diabetic neuropathy, pain due to arthritis, joint pain, myofascial pain, causalgia, brachial plexus avulsion, occipital neuralgia, reflex sympathetic dystrophy, fibromyalgia, gout, phantom limb pain, burn pain, pain associated with spinal cord injury, multiple sclerosis, reflex sympathetic dystrophy and lower back pain and other forms of neuralgia, neuropathic, and idiopathic pain syndromes.

"Nociceptive pain" is due to activation of pain-sensitive nerve fibers, either somatic or visceral. Nociceptive pain is generally a response to direct tissue damage. The initial trauma causes the release of several chemicals including bradykinin, serotonin, substance P, histamine, and prostaglandin. When somatic nerves are involved, the pain is typically experienced as an aching or pressure-like sensation.

In the phrase "pain and related disorders", the term "related disorders" refers to disorders that either cause or are associated with pain, or have been shown to have similar mechanisms to pain. These disorders include addiction, seizure, stroke, ischemia, a neurodegenerative disorder, anxiety, depression, headache, asthma, rheumatic disease, osteoarthritis, retinopathy, inflammatory eye disorders, pruritis, ulcer, gastric lesions, uncontrollable urination, an inflammatory or unstable bladder disorder, inflammatory bowel disease, irritable bowel syndrome (IBS), irritable bowel disease (IBD), gastroesophageal reflux disease (GERD), functional dyspepsia, functional chest pain of presumed oesophageal origin, functional dysphagia, non-cardiac chest pain, symptomatic gastroesophageal disease, gastritis, aerophagia, functional constipation, functional diarrhea, burbulence, chronic functional abdominal pain, recurrent abdominal pain (RAP), functional abdominal bloating, functional biliary pain, functional incontinence, functional ano-rectal pain, chronic pelvic pain, pelvic floor dyssenergia, unspecified functional ano-rectal disorder, cholecystalgia, interstitial cystitis, dysmenorrhea, and dyspareunia.

The invention thus provides the use of an anti-Nav1.8 dsRNA administered to a human, particularly by intrathecal infusion or injection, or by intravenous infusion or injection, for the treatment of pain, including neuropathic and inflammatory pain.

The pharmaceutical compositions encompassed by the invention may be administered by any means known in the art including, but not limited to oral or parenteral routes, including intravenous, intramuscular, intraperitoneal, epidural, intrathecal, intracerebroventricular, intraparenchymal (within the peripheral or central nervous system), subcutaneous, transdermal, intranasal, airway (aerosol), nasal, rectal, vaginal and topical (including buccal and sublingual) administration, and epidural administration. In preferred embodiments, the pharmaceutical compositions are administered intrathecally by continuous infusion such as with a pump, or intrathecally by bolus injection. In other preferred embodiments, the pharmaceutical compositions are administered intravenously by continuous infusion such as with a pump, or intravenously by bolus injection.

Methods for Inhibiting Expression of the Nav1.8 Gene

In yet another aspect, the invention provides a method for inhibiting the expression of the Nav1.8 gene in a mammal. The method comprises administering a composition of the invention to the mammal such that expression of the target Nav1.8 gene is silenced. Because of their high specificity, the dsRNAs of the invention specifically target RNAs (primary or processed) of the target Nav1.8 gene. Compositions and methods for inhibiting the expression of these Nav1.8 genes using dsRNAs can be performed as described elsewhere herein.

In one embodiment, the method comprises administering a composition comprising a dsRNA, wherein the dsRNA comprises a nucleotide sequence which is complementary to at least a part of an RNA transcript of the Nav1.8 gene of the mammal to be treated. When the organism to be treated is a mammal such as a human, the composition may be administered by any means known in the art including, but not limited to oral or parenteral routes, including intravenous, intramuscular, intraperitoneal, epidural, intrathecal, intracerebroventricular, intraparenchymal (within the peripheral or central nervous system), subcutaneous, transdermal, intranasal, airway (aerosol), rectal, vaginal and topical (including buccal and sublingual) administration. In preferred embodiments, the compositions are administered by intrathecal infusion or injection, or by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Gene Walking of the Nav1.8 Gene siRNAs were identified in a multi step sequence analysis process in order to design siRNAs targeting the Nav1.8 gene in 4 species of interest.

ClustalW multiple alignment function of BioEdit Sequence Alignment Editor (version 7.0.4.1) was used to generate a global alignment of human (NM_006514), mouse (NM_009134), rat (NM_017247) and dog (NM001003203) Nav1.8 mRNA sequences.

Conserved regions were identified by embedded sequence analysis function of the software. Conserved regions were defined as sequence stretches with a minimum length of 19 bases for all aligned sequences containing no internal gaps. Sequence positions of conserved regions were counted according to the human sequence.

The siRNA design web interface at Whitehead Institute for Biomedical Research (on the World Wide Web at jura.wi.mit.edu/siRNAext/) was used to identify all potential siRNAs targeting the conserved regions as well as their respective off-target hits to sequences in the human, mouse and rat RefSeq database. siRNAs satisfying the crossreactivity criteria were selected out of the candidates pool and subjected to the software embedded off-target analysis. For this, all selected siRNAs were analyzed in 3 rounds by the NCBI blast algorithm against the NCBI human, mouse and rat RefSeq database.

Blast results were downloaded and analyzed by a perl script in order to extract the identity of the best off-target hit for the antisense strain as well as the positions of occurring mismatches.

All siRNA candidates were ranked according to predicted properties. For this, different criteria were applied in order to identify siRNAs with the following properties:
  reactivity criterium: targeting human, mouse, rat and dog sequences
  specificity criteria: highly specific for human, at least specific for rat and mouse The 2 siRNAs that satisfied the applied criteria were refered to as "multi-species targeting siRNAs".

In order to identify more siRNAs a second round of siRNA identification steps were conducted correspondingly with additional regions that had been previously eliminated due to missing reactivity with dog sequences.

The resulting pool of 10 siRNAs matching the above mentioned criteria were refered to as 'human/rat/mouse targeting siRNAs'.

A third round of the siRNA design process was conducted while disregarding cross-reactivity to mouse.

All candidate siRNAs were again extracted and ranked in 3 steps according to the following criteria:
Step 1:
  reactivity criterium: targeting human, rat and mouse sequences
  specificity criterium: highly specific for human and rat, moderately specific for mouse □□4 siRNAs (added to pool of 'human/rat/mouse targeting siRNAs')
Step 2:
  reactivity criterium: targeting human and rat sequences
  sequence-embedded criterium: absense of stretches with more than 3 Gs in a row
  specificity criterium: highly specific for human □□19 siRNAs
Step 3:
  reactivity criterium: targeting human and rat sequences
  specificity criterium: highly specific for rat, specific for human and favorable ddG value □□1 siRNA The pool resulting form steps 2 and 3 (20 siRNAs) were referred to as 'human/rat targeting siRNAs'.

The in silico selected 36 siRNAs were synthesized (Table 1).

Additional sequence selections were performed using the above generalized methods except that cross reactivity between species was not used as a selection criterea: the sequence selection was based solely on the human Nav1.8 sequence. In addition, ranking was based on off-target scores based on the closest FASTA hit as was as the number of potential off target genes. These siRNAs are provided in Table 4.

TABLE 1 siRNAs specific for Nav1.8

| duplex name | sense strand sequence (5'-3') | SEQ ID NO: | antisense strand sequence (5'-3') | SEQ ID NO: |
|---|---|---|---|---|
| AL-DP-6042 | cmcmcmggaumumumumaacmumacmacmcmTT | 1 | ggugumaguumaaaauccgggTT | 2 |
| AL-DP-6043 | cmcmggaumumumumaacmumacmacmcmaTT | 3 | uggugumaguumaaaauccggTT | 4 |
| AL-DP-6044 | gacmaacmcmcmggaumumumumaacmumTT | 5 | aguumaaaauccggguugucTT | 6 |
| AL-DP-6045 | cmcmumumacmaacmcmagcmgcmaggaTT | 7 | uccugcgcugguugumaaggTT | 8 |
| AL-DP-6046 | aacmcmcmggaumumumumaacmumacmaTT | 9 | ugumaguumaaaauccggguuTT | 10 |
| AL-DP-6047 | umgumgcmaumgacmcmcmgaacmumgaTT | 11 | ucmaguucggucmaugcmacmaTT | 12 |
| AL-DP-6048 | acmaacmcmagcmgcmaggaumgumcmTT | 13 | gacmauccugcgcugguuguTT | 14 |
| AL-DP-6049 | acmcmcmggaumumumumaacmumacmacmTT | 15 | gugumaguumaaaauccggguTT | 16 |
| AL-DP-6050 | cmaumcmcmumaumgaacmcmaaumagcmTT | 17 | gcumauuggucmaumaggaugTT | 18 |
| AL-DP-6051 | cmumumacmaacmcmagcmgcmaggaumTT | 19 | auccugcgcugguugumaagTT | 20 |
| AL-DP-6052 | umumumaacmumacmacmcmagcmumumumgTT | 21 | cmaaagcugguguumaguumaaaTT | 22 |
| AL-DP-6053 | gumgumgcmaumgacmcmcmgaacmumgTT | 23 | cmaguucgggucmaugcmacmacTT | 24 |
| AL-DP-6202 | cmggaumumumumaacmumacmacmcmagTT | 25 | cuggugumaguumaaaauccgTT | 26 |

TABLE 1-continued siRNAs specific for Nav1.8

| duplex name | sense strand sequence (5'-3') | SEQ ID NO: | antisense strand sequence (5'-3') | SEQ ID NO: |
|---|---|---|---|---|
| AL-DP-6203 | umacmaacmcmagcmgcmaggaumgumTT | 27 | acmauccugcgcugguugumaTT | 28 |
| AL-DP-6204 | ggumcmumcmumgumgcmcmcmaumumgcmumTT | 29 | agcmaaugggcmacmagagaccTT | 30 |
| AL-DP-6205 | cmcmcmaagumumcmumaumggumgagcmTT | 31 | gcucmaccmaumagaacuugggTT | 32 |
| AL-DP-6206 | cmaagumumcmumaumggumgagcmumcmTT | 33 | gagcucmaccmaumagaacuugTT | 34 |
| AL-DP-6207 | cmumacmagcmacmacmacmcmggacmaTT | 35 | uguccggugugugcugumagTT | 36 |
| AL-DP-6208 | aagumumcmumaumggumgagcmumcmcmTT | 37 | ggagcucmaccmaumagaacuuTT | 38 |
| AL-DP-6209 | umumumumgumcmumaaaumgagumumcmaTT | 39 | ugaacucmauuumagacmaaaaTT | 40 |
| AL-DP-6210 | cmcmumcmumcmacmumgumumcmcmgcmcmumcmTT | 41 | gaggcggaacmagugagaggTT | 42 |
| AL-DP-6211 | aacmcmagumumcmumumumgumggcmcmgTT | 43 | cggccmacmaaagaacugguuTT | 44 |
| AL-DP-6212 | cmumcmacmumgumumcmcmgcmcmumcmaumgTT | 45 | cmaugaggcggaacmagugagTT | 46 |
| AL-DP-6213 | cmcmaagumumcmumaumggumgagcmumTT | 47 | agcucmaccmaumagaacuugggTT | 48 |
| AL-DP-6214 | cmagumumcmumumumgumggcmcmgumcmumTT | 49 | agacggccmacmaaagaacugTT | 50 |
| AL-DP-6215 | ggcmumggcmaggumgcmgcmaagaTT | 51 | ucuugcgcmaccugccmagccTT | 52 |
| AL-DP-6216 | cmumcmcmumcmumgagggcmagcmacmgTT | 53 | cgugcugcccucmagaggagTT | 54 |
| AL-DP-6217 | gumcmumumcmacmumgumcmaumumumacmaTT | 55 | ugumaaaugacmagugaagacTT | 56 |
| AL-DP-6218 | cmaacmcmagcmgcmaggaumgumcmumTT | 57 | agacmauccugcgcugguugTT | 58 |
| AL-DP-6219 | agaagumaumcmumgaumcmumgggaTT | 59 | ucccmagaucmagaumacuucuTT | 60 |
| AL-DP-6220 | umcmumacmagcmacmacmacmcmggacmTT | 61 | guccggugugugcugumagaTT | 62 |
| AL-DP-6221 | agumumcnumaumggumgagcmumcmcmcmTT | 63 | gggagcucmaccmaumagaacuTT | 64 |
| AL-DP-6222 | umcmumaumggumgagcmumcmcmcmagcmTT | 65 | gcugggagcucmaccmaumagaTT | 66 |
| AL-DP-6223 | agumcmumumumumgumggcmcmgumcmumumTT | 67 | aagacggccmacmaaagaacuTT | 68 |
| AL-DP-6224 | umcmacmumgumumcmcmgcmcmumcmaumgaTT | 69 | ucmaugaggcggaacmagugaTT | 70 |
| AL-DP-6225 | ggaumumumumaacmumacmacmcmagcmTT | 71 | gcuggugumaguumaaaauccTT | 72 |

TABLE 4

Further siRNAs specific for Nav1.8

| duplex name | Sense strand sequence (5'-3') | SEQ ID NO: | Antisense strand sequence (5'-3') | SEQ ID NO: | Remaining Luc activity [% of controls] |
|---|---|---|---|---|---|
| AD-11159 | ccgcuugcugcgcguauucTT | 73 | gaauacgcgcagcaagcggTT | 74 | 26 ± 2 |
| AD-11160 | cuugcuaccguaucguggaTT | 75 | uccacgauacgguagcaagTT | 76 | 52 ± 4 |
| AD-11161 | gacuucaucgcuaauccgaTT | 77 | ucggauuagcgaugaagucTT | 78 | 29 ± 4 |
| AD-11162 | uggauuuuagcgucauuacTT | 79 | guaaugacgcuaaaauccaTT | 80 | 70 ± 6 |
| AD-11163 | cgcuugcugcgcguauucaTT | 81 | ugaauacgcgcagcaagcgTT | 82 | 31 ± 5 |
| AD-11164 | caacuuccgucgcuuuacuTT | 83 | aguaaagcgacggaaguugTT | 84 | 24 ± 2 |
| AD-11165 | gucgcuuuacucccggagucTT | 85 | gacuccggaguaaagcgacTT | 86 | 20 ± 3 |

TABLE 4-continued

Further siRNAs specific for Nav1.8

| duplex name | Sense strand sequence (5'-3') | SEQ ID NO: | Antisense strand sequence (5'-3') | SEQ ID NO: | Remaining Luc activity [% of controls] |
|---|---|---|---|---|---|
| AD-11166 | aaugaguucacguaccugaTT | 87 | ucagguacgugaacucauuTT | 88 | 17 ± 3 |
| AD-11167 | agacuugcuaccguaucguTT | 89 | acgauacgguagcaagucuTT | 90 | 38 ± 2 |
| AD-11168 | aguuuauuuauuacggucaTT | 91 | ugaccguaauaaauaaacuTT | 92 | 63 ± 7 |
| AD-11169 | aaaugaguucacguaccugTT | 93 | cagguacgugaacucauuuTT | 94 | 46 ± 4 |
| AD-11170 | ugucucggcauucgaugcaTT | 95 | ugcaucgaaugccgagacaTT | 96 | 72 ± 5 |
| AD-11171 | ucaaagcccuucgaacccuTT | 97 | aggguucgaagggcuuugaTT | 98 | 96 ± 4 |
| AD-11172 | gcgggcucuuucucgauuuTT | 99 | aaaucgagaaagagcccgcTT | 100 | 34 ± 4 |
| AD-11173 | ccuuguaccuuugucgauuTT | 101 | aaucgacaaagguacaaggTT | 102 | 17 ± 2 |
| AD-11174 | gugguucucuccauugcgaTT | 103 | ucgcaauggagagaaccacTT | 104 | 24 ± 3 |
| AD-11175 | caaaaggccuaucggagcuTT | 105 | agcuccgauaggccuuuugTT | 106 | 46 ± 3 |
| AD-11176 | aaaggccuaucggagcuauTT | 107 | auagcuccgauaggccuuuTT | 108 | 48 ± 5 |
| AD-11177 | ggugcaucaacuauaccgaTT | 109 | ucgguauaguugaugcaccTT | 110 | 21 ± 2 |
| AD-11178 | aacuaccguaacaaccgaaTT | 111 | uucgguuguuacgguaguuTT | 112 | 42 ± 8 |
| AD-11179 | ucgcuuuacuccggagucaTT | 113 | ugacuccggaguaaagcgaTT | 114 | 17 ± 1 |
| AD-11180 | gaaaacgccgggcuagucaTT | 115 | ugacuagcccggcguuuucTT | 116 | 36 ± 8 |
| AD-11181 | accgaaaaaauaucuccgcTT | 117 | gcggagauauuuuuuugguTT | 118 | 105 ± 15 |
| AD-11182 | uucaucgcuaauccgacugTT | 119 | cagucggauuagcgaugaaTT | 120 | 87 ± 14 |
| AD-11183 | uccgucgcuuuacuccggaTT | 121 | uccggaguaaagcgacggaTT | 122 | 33 ± 3 |
| AD-11184 | gcuuuacuccggagucacuTT | 123 | agugacuccggaguaaagcTT | 124 | 14 ± 1 |
| AD-11185 | ggaaaacgccgggcuagucTT | 125 | gacuagcccggcguuuuccTT | 126 | 50 ± 5 |
| AD-11186 | acuaccguaacaaccgaaaTT | 127 | uuucgguuguuacgguaguTT | 128 | 41 ± 5 |
| AD-11187 | uggccaucguaccaaacagTT | 129 | cuguuugguacgauggccaTT | 130 | 85 ± 7 |
| AD-11188 | acuugcuaccguaucguggTT | 131 | ccacgauacgguagcaaguTT | 132 | 109 ± 15 |
| AD-11189 | gauaagucucacagcgaagTT | 133 | cuucgcugugagacuuaucTT | 134 | 29 ± 4 |
| AD-11190 | auaagucucacagcgagaTT | 135 | ucuucgcugugagacuuauTT | 136 | 34 ± 4 |
| AD-11191 | aagcccuucgaacccuucgTT | 137 | cgaaggguucgaagggcuuTT | 138 | 86 ± 10 |
| AD-11192 | agcccuucgaacccuucgcTT | 139 | gcgaaggguucgaagggcuTT | 140 | 98 ± 16 |
| AD-11193 | cccuucgaacccuucgcgcTT | 141 | gcgcgaaggguucgaagggTT | 142 | 64 ± 4 |
| AD-11194 | aacccaaucgaaauauacuTT | 143 | aguauauuucgauuggguuTT | 144 | 40 ± 4 |
| AD-11195 | cgcuuuacuccggagucacTT | 145 | gugacuccggaguaaagcgTT | 146 | 17 ± 2 |
| AD-11196 | gaccauucccgguuuaguTT | 147 | acuaaaccgggaaauggucTT | 148 | 77 ± 4 |
| AD-11197 | cgguuuagugccacucgggTT | 149 | cccgagugggcacuaaaccgTT | 150 | 58 ± 6 |
| AD-11198 | cacagcaauagaucuccguTT | 151 | acggagaucuauugcugugTT | 152 | 34 ± 4 |
| AD-11199 | acuagggauugacacaaccTT | 153 | gguuguguccaaucccuaguTT | 154 | 86 ± 3 |
| AD-11200 | cccacaauggaucaccuuuTT | 155 | aaaggugauccauugugggTT | 156 | 22 ± 0 |
| AD-11201 | ugucuuuucuaggccucgcTT | 157 | gcgaggccuagaaaagacaTT | 158 | 91 ± 10 |

TABLE 4-continued

Further siRNAs specific for Nav1.8

| duplex name | Sense strand sequence (5'-3') | SEQ ID NO: | Antisense strand sequence (5'-3') | SEQ ID NO: | Remaining Luc activity [% of controls] |
|---|---|---|---|---|---|
| AD-11202 | agcugucgaugucucggcaTT | 159 | ugccgagacaucgacagcuTT | 160 | 42 ± 2 |
| AD-11203 | gucucggcauucgaugcagTT | 161 | cugcaucgaaugccgagacTT | 162 | 62 ± 5 |
| AD-11204 | ucaaaaucauugccuucgaTT | 163 | ucgaaggcaaugauuuugaTT | 164 | 42 ± 7 |
| AD-11205 | cccgcuggcacaugcacgaTT | 165 | ucgugcaugugccagcgggTT | 166 | 42 ± 4 |
| AD-11206 | ucauugucuuccguauccuTT | 167 | aggauacggaagacaaugaTT | 168 | 79 ± 11 |
| AD-11207 | uuggccaucguaccaaacaTT | 169 | uguuugguacgauggccaaTT | 170 | 59 ± 8 |
| AD-11208 | gcacgguggacugccuagaTT | 171 | ucuaggcaguccaccgugcTT | 172 | 95 ± 12 |
| AD-11209 | gcccuucgaacccuucgcgTT | 173 | cgcgaagggcuucgaagggcTT | 174 | 48 ± 4 |
| AD-11210 | ugcgggcucuuucucgauuTT | 175 | aaucgagaaagagcccgcaTT | 176 | 35 ± 5 |
| AD-11211 | gaggugcaucaacuauaccTT | 177 | gguauaguugaugcaccucTT | 178 | 36 ± 4 |
| AD-11212 | caucaacuauaccgauggaTT | 179 | uccaucgguauaguugaugTT | 180 | 58 ± 4 |
| AD-11213 | aaaucauccuaugaaccaaTT | 181 | uugguucauaggaugauuuTT | 182 | 26 ± 2 |
| AD-11214 | aaggccuaucggagcuaugTT | 183 | cauagcuccgauaggccuuTT | 184 | 63 ± 4 |
| AD-11215 | uguacucccagacaaaucuTT | 185 | agauuugucugggagaacaTT | 186 | 40 ± 3 |
| AD-11216 | aggacaucuagcucaauacTT | 187 | guauugagcuagauguccuTT | 188 | 29 ± 2 |
| AD-11217 | ccgguuuagugccacucggTT | 189 | ccgaguggcacuaaaccggTT | 190 | 22 ± 2 |
| AD-11218 | caucgcuaauccgacugugTT | 191 | cacagucggauuagcgaugTT | 192 | 51 ± 2 |
| AD-11219 | aaacuaccguaacaaccgaTT | 193 | ucgguuguuacgguaguuuTT | 194 | 29 ± 3 |
| AD-11220 | aucgcuaauccgacuguguTT | 195 | acacagucggauuagcgauTT | 196 | 52 ± 1 |
| AD-11221 | cccgguuuagugccacucgTT | 197 | cgaguggcacuaaaccgggTT | 198 | 60 ± 1 |
| AD-11222 | uuuagcgucauuacccuggTT | 199 | ccaggguaaugacgcuaaaTT | 200 | 105 ± 3 |
| AD-11223 | aauaagcgaggcacuucugTT | 201 | cagaagugccucgcuuauuTT | 202 | 66 ± 5 |
| AD-11224 | cuaccguaacaaccgaaaaTT | 203 | uuuucgguuguuacgguagTT | 204 | 25 ± 3 |
| AD-11225 | ucgcuaauccgacuguguGTT | 205 | cacacagucggauuagcgaTT | 206 | 70 ± 5 |
| AD-11226 | ucccucgaaacuaacaacuTT | 207 | aguuguuaguuucgagggaTT | 208 | 24 ± 3 |
| AD-11227 | cuuccgucgcuuuacuccgTT | 209 | cggaguaaagcgacggaagTT | 210 | 31 ± 0 |
| AD-11228 | uuucccgguuuagugccacTT | 211 | guggcacuaaaccgggaaaTT | 212 | 101 ± 2 |
| AD-11229 | gguuuagugccacucgggcTT | 213 | gcccgaguggcacuaaaccTT | 214 | 67 ± 1 |
| AD-11230 | acaacccggauuuuaacuaTT | 215 | uaguuaaaauccgguuguTT | 216 | 48 ± 3 |
| AD-11231 | cuagggauugacacaaccuTT | 217 | agguugugucaaucccuagTT | 218 | 39 ± 2 |
| AD-11232 | ugucgauugugaauaacaaTT | 219 | uuguuauucacaaucgacaTT | 220 | 25 ± 3 |
| AD-11233 | caucgugaccagacaagcuTT | 221 | agcuugucuggucacgaugTT | 222 | 47 ± 4 |
| AD-11234 | ccuaucggagcuaugugcuTT | 223 | agcacauagcuccgauaggTT | 224 | 58 ± 7 |
| AD-11235 | uuagcgucauuacccuggcTT | 225 | gccaggguaaugacgcuaaTT | 226 | 92 ± 7 |
| AD-11236 | agcaauagaucuccguggGTT | 227 | cccacggagaucuauugcuTT | 228 | 83 ± 4 |

TABLE 4-continued

Further siRNAs specific for Nav1.8

| duplex name | Sense strand sequence (5'-3') | SEQ ID NO: | Antisense strand sequence (5'-3') | SEQ ID NO: | Remaining Luc activity [% of controls] |
|---|---|---|---|---|---|
| AD-11237 | aucgaaauauacugauccaTT | 229 | uggaucaguauauuucgauTT | 230 | 57 ± 3 |
| AD-11238 | ggaucccucgaaacuaacaTT | 231 | uguuaguuucgagggauccTT | 232 | 18 ± 1 |
| AD-11239 | acaccggacauuuauggugTT | 233 | caccauaaauguccggugTT | 234 | 96 ± 2 |
| AD-11240 | guuuagugccacucgggccTT | 235 | ggcccgaguggcacuaaacTT | 236 | 95 ± 17 |
| AD-11241 | augacccgaacugaccuucTT | 237 | gaaggucaguucgggucauTT | 238 | 80 ± 7 |
| AD-11242 | auuuuagcgucauuacccuTT | 239 | aggguaaugacgcuaaaauTT | 240 | 70 ± 5 |
| AD-11243 | uuuuagcgucauuacccugTT | 241 | caggguaaugacgcuaaaaTT | 242 | 77 ± 8 |
| AD-11244 | gcaauagaucuccgugggaTT | 243 | ucccacggagaucuauugcTT | 244 | 23 ± 1 |
| AD-11245 | aaauaagcgaggcacuucuTT | 245 | agaagugccucgcuuauuuTT | 246 | 38 ± 3 |
| AD-11246 | auaagcgaggcacuucugaTT | 247 | ucagaagugccucgcuuauTT | 248 | 32 ± 2 |
| AD-11247 | ugauccuuacaaccagcgcTT | 249 | gcgcugguuguaaggaucaTT | 250 | 78 ± 2 |
| AD-11248 | uggccgagauaucucacucTT | 251 | gagugagauaucucggccaTT | 252 | 66 ± 1 |
| AD-11249 | caaccgccgcccacuagugTT | 253 | cacuaguggcggcgguugTT | 254 | 71 ± 4 |
| AD-11250 | uuagaugaaccuuuccgggTT | 255 | cccggaaagguucaucuaaTT | 256 | 90 ± 3 |
| AD-11251 | aaccuuuccgggcccaaagTT | 257 | cuuugggcccggaaagguuTT | 258 | 99 ± 7 |
| AD-11252 | auaaccuccguccuugaggTT | 259 | ccucaaggacggagguuauTT | 260 | 105 ± 2 |
| AD-11253 | cuugugacggaucccuuugTT | 261 | caaagggauccgucacaagTT | 262 | 62 ± 5 |
| AD-11254 | ccuaccuucgaagccaugcTT | 263 | gcauggcuucgaagguagTT | 264 | 84 ± 6 |
| AD-11255 | aaaucauugccuucgacccTT | 265 | gggucgaaggcaaugauuuTT | 266 | 92 ± 6 |
| AD-11256 | cauugccuucgacccauacTT | 267 | guaugggucgaaggcaaugTT | 268 | 42 ± 2 |
| AD-11257 | cuucgacccauacuauuauTT | 269 | auaauagauggggucgaagTT | 270 | 35 ± 2 |
| AD-11258 | ucaucgcuaauccgacuguTT | 271 | acagucggauuagcgaugaTT | 272 | 76 ± 2 |
| AD-11259 | aauccgacugugugggucuTT | 273 | agacccacacagucggauuTT | 274 | 87 ± 5 |
| AD-11260 | agcacggguggacugccuagTT | 275 | cuaggcaguccaccgugcuTT | 276 | 75 ± 7 |
| AD-11261 | ggugcgcaagacuugcuacTT | 277 | guagcaagucuugcgcaccTT | 278 | 34 ± 3 |
| AD-11262 | aggugcaucaacuauaccgTT | 279 | cgguauaguugaugcaccuTT | 280 | 59 ± 5 |
| AD-11263 | aucaacuauaccgauggagTT | 281 | cuccaucgguauaguugauTT | 282 | 113 ± 10 |
| AD-11264 | uugucgauugugaauaacaTT | 283 | uguuauucacaaucgacaaTT | 284 | 36 ± 5 |
| AD-11265 | aauggguuaccuugcacuuTT | 285 | aagugcaagguaacccauuTT | 286 | 70 ± 6 |
| AD-11266 | aggccuaucggagcuauguTT | 287 | acauagcuccgauaggccuTT | 288 | 72 ± 4 |
| AD-11267 | ggccuaucggagcuaugugTT | 289 | cacauagcuccgauaggccTT | 290 | 65 ± 7 |
| AD-11268 | uaucggagcuaugugcugcTT | 291 | gcagcacauagcuccgauaTT | 292 | 110 ± 10 |
| AD-11269 | ccguccuaugagagugucaTT | 293 | ugacacucucauaggacggTT | 294 | 50 ± 3 |
| AD-11270 | ccauuggaucccucgaaacTT | 295 | guuucgagggauccaauggTT | 296 | 18 ± 3 |
| AD-11271 | cauuggaucccucgaaacuTT | 297 | aguuucgagggauccaaugTT | 298 | 23 ± 3 |
| AD-11272 | aucccucgaaacuaacaacTT | 299 | guuguuaguuucgagggauTT | 300 | 76 ± 5 |

TABLE 4-continued

Further siRNAs specific for Nav1.8

| duplex name | Sense strand sequence (5'-3') | SEQ ID NO: | Antisense strand sequence (5'-3') | SEQ ID NO: | Remaining Luc activity [% of controls] |
|---|---|---|---|---|---|
| AD-11273 | gaaacuaacaacuuccgucTT | 301 | gacggaaguuguuaguuucTT | 302 | 21 ± 3 |
| AD-11274 | uuccgucgcuuuacuccggTT | 303 | ccggaguaaagcgacggaaTT | 304 | 87 ± 6 |
| AD-11275 | ccgucgcuuuacuccggagTT | 305 | cuccggaguaaagcgacggTT | 306 | 29 ± 2 |
| AD-11276 | ggaucuagauccguucuacTT | 307 | guagaacggaucuagauccTT | 308 | 22 ± 3 |
| AD-11277 | cacacaccggacauuuaugTT | 309 | cauaaauguccggugugugTT | 310 | 57 ± 2 |
| AD-11278 | cacaccggacauuuaugguTT | 311 | accauaaauguccggugugTT | 312 | 101 ± 1 |
| AD-11279 | ggaccauuucccgguuuagTT | 313 | cuaaaccgggaaauggcccTT | 314 | 45 ± 4 |
| AD-11280 | accauuucccgguuuagugTT | 315 | cacuaaaccgggaaaugguTT | 316 | 89 ± 2 |
| AD-11281 | auuucccgguuuagugccaTT | 317 | uggcacuaaaccgggaaauTT | 318 | 100 ± 4 |
| AD-11282 | aaccugaucagaagaacggTT | 319 | ccguucuucugaucagguuTT | 320 | 66 ± 5 |
| AD-11283 | ucaguuuauuuauuacgguTT | 321 | accguaauaaauaaacugaTT | 322 | 76 ± 4 |
| AD-11284 | gugcaugacccgaacugacTT | 323 | gucaguucgggucaugcacTT | 324 | 29 ± 1 |
| AD-11285 | augaguucacguaccugaTT | 325 | cucaggacgugaacucauTT | 326 | 37 ± 4 |
| AD-11286 | agcgucauuacccuggcauTT | 327 | augccagggduaaugacgcuTT | 328 | 31 ± 1 |
| AD-11287 | gcgucauuacccuggcauaTT | 329 | uaugccagggduaaugacgcTT | 330 | 16 ± 1 |
| AD-11288 | gucauuacccuggcauaugTT | 331 | cauaugccagggduaaugacTT | 332 | 21 ± 1 |
| AD-11289 | acagcaauagaucuccgugTT | 333 | cacggagaucuauugcuguTT | 334 | 64 ± 4 |
| AD-11290 | ggacauucagaguucuuagTT | 335 | cuaagaacucugaaugaccTT | 336 | 26 ± 1 |
| AD-11291 | ucuacauaaauaagcgaggTT | 337 | ccucgcuuauuuauguagaTT | 338 | 88 ± 15 |
| AD-11292 | uaaauaagcgaggcacuucTT | 339 | gaagugccucgcuuauuuaTT | 340 | 68 ± 2 |
| AD-11293 | ugcccugaugguuauaucuTT | 341 | agauauaaccaucagggcaTT | 342 | 39 ± 3 |
| AD-11294 | caacccggauuuuaacuacTT | 343 | guaguuaaaauccggguugTT | 344 | 26 ± 2 |
| AD-11295 | gggaaaaucuauaugaucuTT | 345 | agaucauauagauuuucccTT | 346 | 15 ± 1 |
| AD-11296 | gcccucgagaugcuccggaTT | 347 | uccggagcaucucgagggcTT | 348 | 54 ± 9 |
| AD-11297 | agggauugacacaaccucuTT | 349 | agagguugugucaauccTT | 350 | 22 ± 1 |
| AD-11298 | gggauugacacaaccucucTT | 351 | gagagguugugucaaucccTT | 352 | 22 ± 2 |
| AD-11299 | cacaauggaucaccuuuaaTT | 353 | uuaaaggugauccauugugTT | 354 | 23 ± 0 |
| AD-11300 | ccgcucugauccuuacaacTT | 355 | guuguaaggaucagagcggTT | 356 | 34 ± 2 |
| AD-11301 | auccuuacaaccagcgcagTT | 357 | cugcgcugguuguaaggauTT | 358 | 90 ± 5 |
| AD-11302 | agcgcaggaugucuuuucuTT | 359 | agaaaagacauccugcgcuTT | 360 | 46 ± 3 |
| AD-11303 | cuuuucuaggccucgccucTT | 361 | gaggcgaggccuagaaaagTT | 362 | 94 ± 10 |
| AD-11304 | cuggaaaacgccgggcuagTT | 363 | cuagcccggcguuuuccagTT | 364 | 57 ± 2 |
| AD-11305 | aaacgccgggcuagucaugTT | 365 | caugacuagcccggcguuuTT | 366 | 95 ± 7 |
| AD-11306 | aacgccgggcuagucauggTT | 367 | ccaugacuagcccggcguuTT | 368 | 101 ± 5 |
| AD-11307 | agaccacgaaagccaucggTT | 369 | ccgauggcuuucgguggcuTT | 370 | 89 ± 6 |

TABLE 4-continued

Further siRNAs specific for Nav1.8

| duplex name | Sense strand sequence (5'-3') | SEQ ID NO: | Antisense strand sequence (5'-3') | SEQ ID NO: | Remaining Luc activity [% of controls] |
|---|---|---|---|---|---|
| AD-11308 | cucccuagaagcccucuucTT | 371 | gaagagggcuucuagggagTT | 372 | 50 ± 3 |
| AD-11309 | agaugaacaccaaccgccgTT | 373 | cggcgguuggguguucaucuTT | 374 | 62 ± 7 |
| AD-11310 | augaacaccaaccgccgccTT | 375 | ggcggcgguuggguguucauTT | 376 | 99 ± 6 |
| AD-11311 | aaccgccgcccacuagugaTT | 377 | ucacuagugggcggcgguuTT | 378 | 72 ± 2 |
| AD-11312 | accgccgcccacuagugagTT | 379 | cucacuagugggcggcgguTT | 380 | 99 ± 13 |
| AD-11313 | gcugucgaugucucggcauTT | 381 | augccgagacaucgacagcTT | 382 | 67 ± 8 |
| AD-11314 | ucgaugucucggcauucgaTT | 383 | ucgaaugccgagacaucgaTT | 384 | 36 ± 2 |
| AD-11315 | ucucggcauucgaugcaggTT | 385 | ccugcaucgaaugccgagaTT | 386 | 99 ± 5 |
| AD-11316 | ggcauucgaugcaggacaaTT | 387 | uuguccugcaucgaaugccTT | 388 | 48 ± 5 |
| AD-11317 | gcauucgaugcaggacaaaTT | 389 | uuuguccugcaucgaaugcTT | 390 | 56 ± 5 |
| AD-11318 | cuuagaugaaccuuuccggTT | 391 | ccggaaagguucaucuaagTT | 392 | 47 ± 3 |
| AD-11319 | gaguguugucaguaucauaTT | 393 | uaugauacugacaacacucTT | 394 | 22 ± 2 |
| AD-11320 | caguaucauaaccuccgucTT | 395 | gacggagguuaugauacugTT | 396 | 27 ± 2 |
| AD-11321 | cucgaggagucugaacagaTT | 397 | ucuguucagacuccucgagTT | 398 | 32 ± 2 |
| AD-11322 | guaucugaucugggauugcTT | 399 | gcaaucccagaucagauacTT | 400 | 65 ± 3 |
| AD-11323 | agacaauucucuuugggcuTT | 401 | agcccaaagagaauugucuTT | 402 | 73 ± 2 |
| AD-11324 | caccuugugcaucguggugTT | 403 | caccacgaugcacaaggugTT | 404 | 47 ± 4 |
| AD-11325 | gcaugagcccuaccuucgaTT | 405 | ucgaagguagggcucaugcTT | 406 | 25 ± 1 |
| AD-11326 | uaccuucgaagccaugcucTT | 407 | gagcauggcuucgaagguaTT | 408 | 71 ± 2 |
| AD-11327 | caaaaucauugccuucgacTT | 409 | gucgaaggcaaugauuuugTT | 410 | 33 ± 3 |
| AD-11328 | aucauugccuucgacccauTT | 411 | augggucgaaggcaaugauTT | 412 | 38 ± 2 |
| AD-11329 | ucauugccuucgacccauaTT | 413 | uaugggucgaaggcaaugaTT | 414 | 29 ± 1 |
| AD-11330 | auugccuucgacccauacuTT | 415 | aguaugggucgaaggcaauTT | 416 | 77 ± 7 |
| AD-11331 | ucgacccauacuauuauuuTT | 417 | aaauaauaguaugggucgaTT | 418 | 55 ± 3 |
| AD-11332 | caucaucgucacugugaguTT | 419 | acucacagugacgaugaugTT | 420 | 31 ± 3 |
| AD-11333 | caucgucacugugagucugTT | 421 | cagacucacagugacgaugTT | 422 | 33 ± 4 |
| AD-11334 | ucgucacugugagucugcuTT | 423 | agcagacucacagugacgaTT | 424 | 44 ± 4 |
| AD-11335 | ggaaaacuaccguaacaacTT | 425 | guuguuacgguaguuuuccTT | 426 | 34 ± 1 |
| AD-11336 | uaccguaacaaccgaaaaaTT | 427 | uuuuucgguuguuacgguaTT | 428 | 21 ± 3 |
| AD-11337 | cguaacaaccgaaaaaauaTT | 429 | uauuuuucgguuguuacgTT | 430 | 29 ± 2 |
| AD-11338 | aaaauccauaugccucaucTT | 431 | gaugaggcauauggauuuuTT | 432 | 87 ± 4 |
| AD-11339 | cuguucaucgcccugcuauTT | 433 | auagcagggcgaugaacagTT | 434 | 40 ± 2 |
| AD-11340 | uguucaucgcccugcuauuTT | 435 | aauagcagggcgaugaacaTT | 436 | 26 ± 1 |
| AD-11341 | cccugcuauugaacucuuuTT | 437 | aaagaguucaauagcagggTT | 438 | 29 ± 1 |
| AD-11342 | ggccaucguaccaaacaggTT | 439 | ccguuuugguacgauggccTT | 440 | 41 ± 2 |
| AD-11343 | ccaucguaccaaacaggcuTT | 441 | agccuguuuugguacgauggTT | 442 | 47 ± 2 |

TABLE 4-continued

Further siRNAs specific for Nav1.8

| duplex name | Sense strand sequence (5'-3') | SEQ ID NO: | Antisense strand sequence (5'-3') | SEQ ID NO: | Remaining Luc activity [% of controls] |
|---|---|---|---|---|---|
| AD-11344 | cagugacuucaucgcuaauTT | 443 | auuagcgaugaagucacugTT | 444 | 33 ± 2 |
| AD-11345 | cuucaucgcuaauccgacuTT | 445 | agucggauuagcgaugaagTT | 446 | 36 ± 2 |
| AD-11346 | uaauccgacuguguggucTT | 447 | gacccacacagucggauuaTT | 448 | 97 ± 3 |
| AD-11347 | gaaucugaucuugaugacuTT | 449 | agucaucaagaucagauucTT | 450 | 45 ± 2 |
| AD-11348 | aagaguccaugggaugugGTT | 451 | ccacaucccauggacucuuTT | 452 | 100 ± 2 |
| AD-11349 | gcaggugcgcaagacuugcTT | 453 | gcaagucuugcgcaccugcTT | 454 | 39 ± 3 |
| AD-11350 | gcgcaagacuugcuaccguTT | 455 | acgguagcaagucuugcgcTT | 456 | 29 ± 1 |
| AD-11351 | aagacuugcuaccguaucgTT | 457 | cgauacgguagcaagucuuTT | 458 | 82 ± 2 |
| AD-11352 | gacuugcuaccguaucgugTT | 459 | cacgauacgguagcaagucTT | 460 | 56 ± 2 |
| AD-11353 | cucauugugaauaucucacTT | 461 | gugagauauuucacaaugagTT | 462 | 54 ± 3 |
| AD-11354 | ugauaagucucacagcgaaTT | 463 | uucgcugugagacuuaucaTT | 464 | 31 ± 1 |
| AD-11355 | aucaaagcccuucgaacccTT | 465 | ggguucgaagggcuuugauTT | 466 | 87 ± 8 |
| AD-11356 | aaagcccuucgaacccuucTT | 467 | gaagggguucgaagggcuuuTT | 468 | 83 ± 3 |
| AD-11357 | ccuucgaacccuucgcgcuTT | 469 | agcgcgaagggguucgaaggTT | 470 | 50 ± 1 |
| AD-11358 | cuucgaacccuucgcgcucTT | 471 | gagcgcgaaggguucgaagTT | 472 | 55 ± 4 |
| AD-11359 | ugcaucaacuauaccgauGTT | 473 | caucgguauaguugaugcaTT | 474 | 59 ± 7 |
| AD-11360 | cccuuguaccuuugucgauTT | 475 | aucgacaaaggguacaagggTT | 476 | 24 ± 3 |
| AD-11361 | uuguaccuuugucgauuguTT | 477 | acaaucgacaaagguacaaTT | 478 | 39 ± 6 |
| AD-11362 | uuugauaauguuugcaauggTT | 479 | ccauugcaacauuaucaaaTT | 480 | 110 ± 14 |
| AD-11363 | gcaaugggguuaccuugcacTT | 481 | gugcaagguaacccauugcTT | 482 | 93 ± 6 |
| AD-11364 | uggguuaccuugcacuucuTT | 483 | agaagugcaagguaacccaTT | 484 | 54 ± 11 |
| AD-11365 | gcuguugauucccgggaggTT | 485 | ccucccgggaaucaacagcTT | 486 | 36 ± 1 |
| AD-11366 | aucgugaccagacaagcuuTT | 487 | aagcuugucuggucacgauTT | 488 | 36 ± 5 |
| AD-11367 | cgucuucacaggcgaaugUTT | 489 | acauucgccugugaagacgTT | 490 | 57 ± 2 |
| AD-11368 | ucacaggcgaaugugucauTT | 491 | augacacauucgccugugaTT | 492 | 76 ± 5 |
| AD-11369 | cacaggcgaaugugucaugTT | 493 | caugacacauucgccugugTT | 494 | 75 ± 4 |
| AD-11370 | caggcgaaugugucaugaaTT | 495 | uucaugacacauucgccugTT | 496 | 32 ± 5 |
| AD-11371 | aggcgaaugugucaugaagTT | 497 | cuucaugacacauucgccuTT | 498 | 48 ± 6 |
| AD-11372 | uguucgcuuugaggcaguaTT | 499 | uacugccucaaagcgaacaTT | 500 | 36 ± 4 |
| AD-11373 | gcaguacuacuucacaaauTT | 501 | auuugugaaguaguacugcTT | 502 | 27 ± 2 |
| AD-11374 | uccauugcgagccugauuuTT | 503 | aaaucaggcucgcaauggaTT | 504 | 24 ± 2 |
| AD-11375 | ccauugcgagccugauuuuTT | 505 | aaaaucaggcucgcaauggTT | 506 | 21 ± 3 |
| AD-11376 | aucgggcuguugcuauuccTT | 507 | ggaauagcaacagcccgauTT | 508 | 78 ± 11 |
| AD-11377 | aaaacccaaucgaaauauaTT | 509 | uauauuucgauuggguuuuTT | 510 | 33 ± 4 |
| AD-11378 | caaucgaaauauacugaucTT | 511 | gaucaguauauuucgauugTT | 512 | 66 ± 8 |

TABLE 4-continued

Further siRNAs specific for Nav1.8

| duplex name | Sense strand sequence (5'-3') | SEQ ID NO: | Antisense strand sequence (5'-3') | SEQ ID NO: | Remaining Luc activity [% of controls] |
|---|---|---|---|---|---|
| AD-11379 | aaucgaaauauacugauccTT | 513 | ggaucaguauauuucgauuTT | 514 | 128 ± 8 |
| AD-11380 | ucgaaauauacugauccagTT | 515 | cuggaucaguauauuucgaTT | 516 | 119 ± 7 |
| AD-11381 | aaucauccuaugaaccaauTT | 517 | auugguucauaggaugauuTT | 518 | 39 ± 3 |
| AD-11382 | uaugaaccaauagcaaccaTT | 519 | ugguugcuauugguucauaTT | 520 | 61 ± 4 |
| AD-11383 | cacucuccgauggaagcaaTT | 521 | uugcuuccaucggagagugTT | 522 | 69 ± 5 |
| AD-11384 | cuaucggagcuaugugcugTT | 523 | cagcacauagcuccgauagTT | 524 | 95 ± 10 |
| AD-11385 | agcaaaugaaaauguguaTT | 525 | uacacaauuuucauuugcuTT | 526 | 79 ± 6 |
| AD-11386 | uacucccagacaaaucugaTT | 527 | ucagauuugucugggaguaTT | 528 | 36 ± 4 |
| AD-11387 | agagugucacuagaggccuTT | 529 | aggccucuagugacacucuTT | 530 | 36 ± 1 |
| AD-11388 | ggccuuagugauagagucaTT | 531 | ugacucuaucacuaaggccTT | 532 | 35 ± 4 |
| AD-11389 | agugauagagucaacaugaTT | 533 | ucauguugacucuaucacuTT | 534 | 29 ± 5 |
| AD-11390 | gauagagucaacaugaggaTT | 535 | uccucauguugacucuaucTT | 536 | 32 ± 3 |
| AD-11391 | caucuagcucaauacaaaaTT | 537 | uuuuguauugagcuagaugTT | 538 | 23 ± 3 |
| AD-11392 | cuagcucaauacaaaaugaTT | 539 | ucauuuuguauugagcuagTT | 540 | 28 ± 5 |
| AD-11393 | aguauggagcugauugcccTT | 541 | gggcaaucagcuccauacuTT | 542 | 108 ± 8 |

Example 2

Optimization of siRNAs by Chemical Modification

As has been experienced by those working in the antisense field, ribonucleic acids are often quickly degraded by a range of nucleases present in virtually all biological environments, e.g. endonucleases, exonucleases etc. This vulnerability may be circumvented by chemically modifying these oligonucleotides such that nucleases may no longer attack. Consequently, siRNAs in Table 1 represent chemically modified oligonucleotides; these chemically modified siRNAs were tested for inhibitory activity on Nav1.8 gene expression (Nav1.8 mRNA levels).

dsRNA Synthesis
Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 μmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol or -sChol, depending on whether the link to the cholesteryl group is effected via a phosphodiester or a phosporothioate diester group), an appropriately modified solid support was used for RNA synthesis. The modified solid support was prepared as follows:

Diethyl-2-azabutane-1,4-dicarboxylate AA

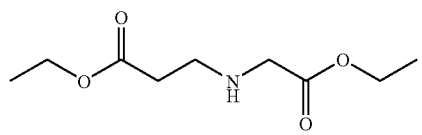

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

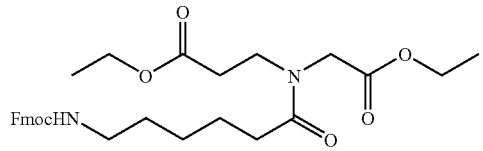

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

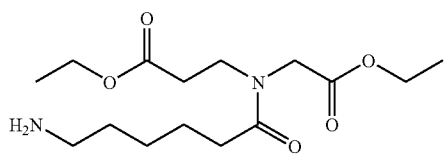

3-{Ethoxycarbonylmethyl-[6-(9H-fluoren-9-ylmethoxycarbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

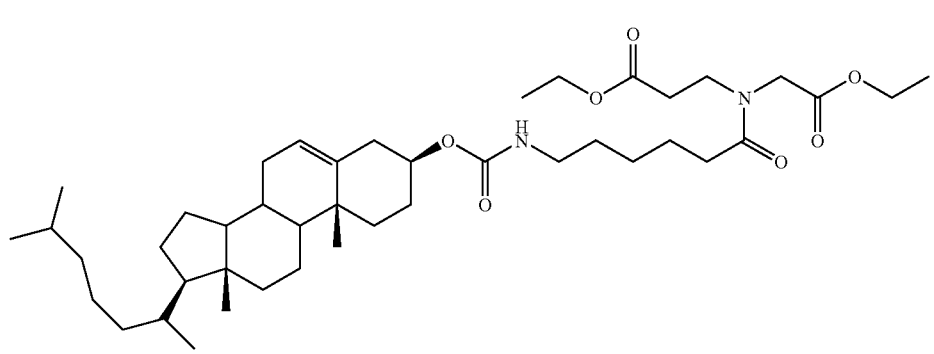

The hydrochloride salt of 3-[(6-Amino-hexanoyl)-ethoxy-carbonylmethyl-amino]-propionic acid ethyl ester AC (4.7 g, 14.8 mmol) was taken up in dichloromethane. The suspension was cooled to 0° C. on ice. To the suspension diisopropyl-ethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1-{6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}-4-oxo-pyrrolidine-3-carboxylic acid ethyl ester AE and 1 mL of glacial acetic acid was added, immediately followed by 4 g of NaH$_2$PO4.H$_2$O in 40 mL of water The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-ketoester (39%).

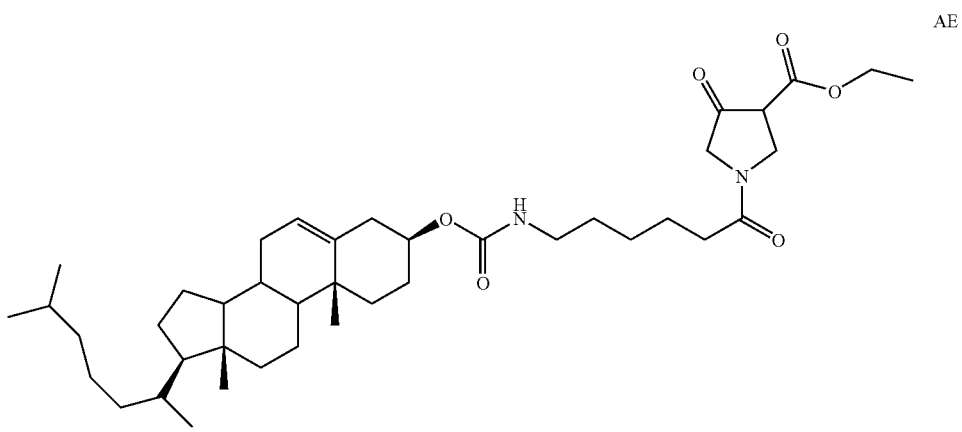

Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C.

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

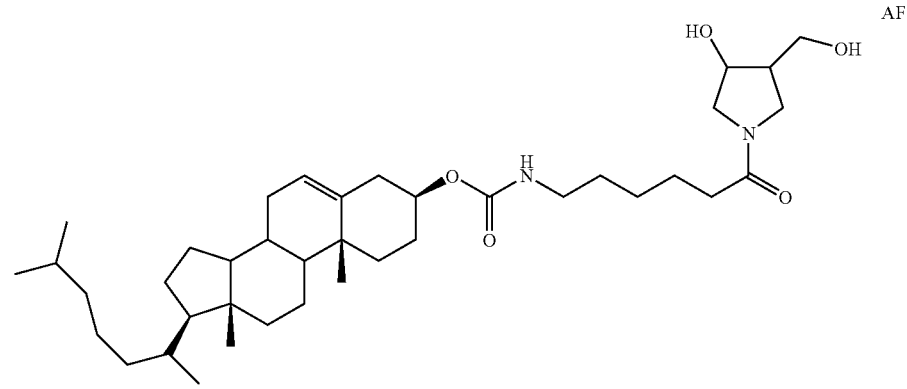

Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated under vacuum to yield the product which was purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

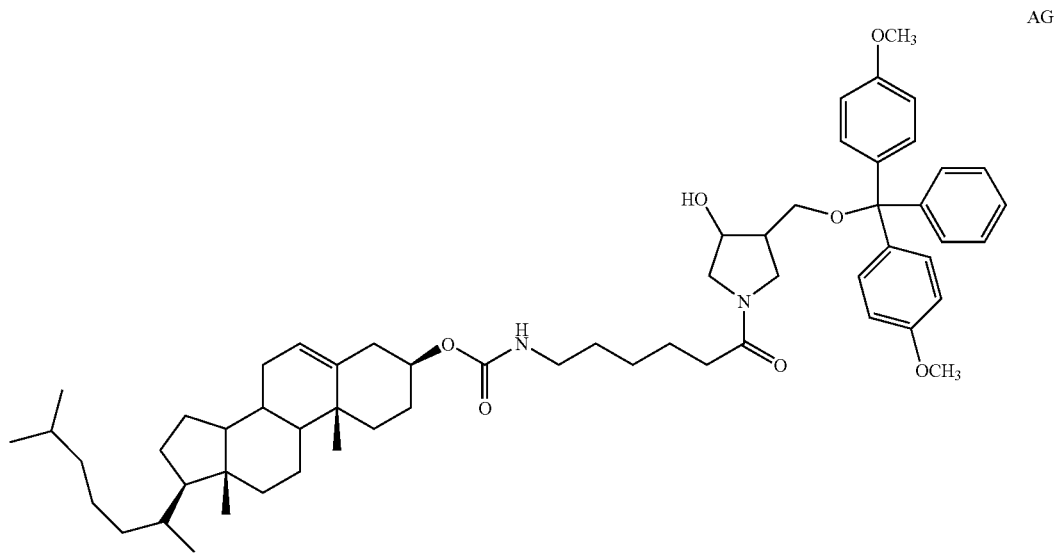

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated under vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl$_3$) (1.75 g, 95%).

Succinic acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

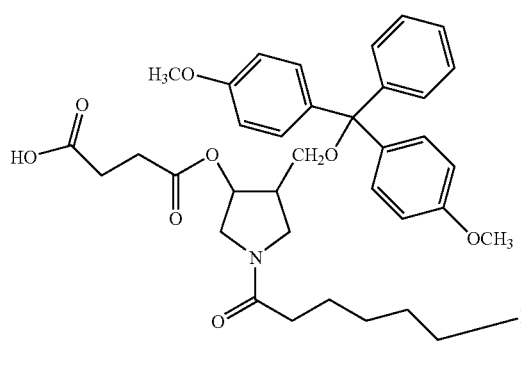
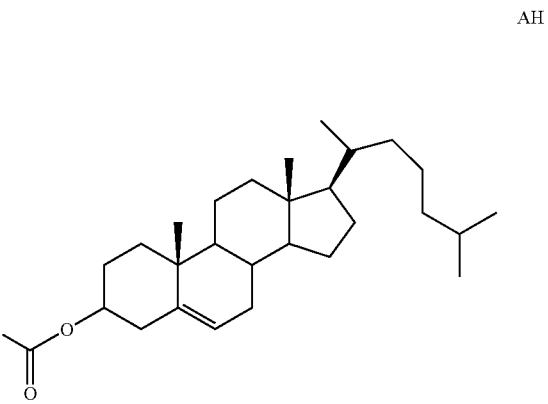

AH

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt%, 30 mL) and water (2×20 mL). The organic phase was dried over anhydrous sodium sulfate and concentrated to dryness. The residue was used as such for the next step.

Cholesterol derivatised CPG AI

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using a wrist-action shaker (5 mins). Long chain alkyl amine-CPG (LCAA-CPG) (1.5 g, 61 mM) was added. The suspension was agitated for 2 h. The CPG was filtered through a sintered funnel and washed with acetonitrile, dichloromethane and ether successively. Unreacted amino groups were masked using acetic anhydride/pyridine. The achieved loading of the CPG was measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except that, for the cholesteryl derivative, the oxidation step was performed using the Beaucage reagent in order to intro-

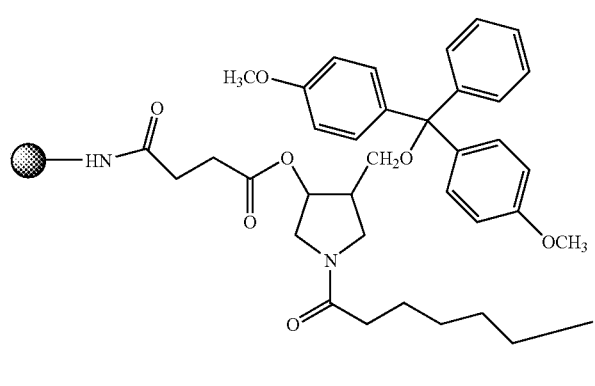

AI duce a phosphorothioate linkage at the 5'-end of the nucleic acid oligomer.

Nucleic acid sequences are represented below using standard nomenclature, and specifically the abbreviations of Table 2.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation[a] | Nucleotide(s) |
|---|---|
| A, a | 2'-deoxy-adenosine-5'-phosphate, adenosine-5'-phosphate |
| C, c | 2'-deoxy-cytidine-5'-phosphate, cytidine-5'-phosphate |
| G, g | 2'-deoxy-guanosine-5'-phosphate, guanosine-5'-phosphate |
| T, t | 2'-deoxy-thymidine-5'-phosphate, thymidine-5'-phosphate |
| U, u | 2'-deoxy-uridine-5'-phosphate, uridine-5'-phosphate |
| N, n | any 2'-deoxy-nucleotide/nucleotide (G, A, C, or T, g, a, c or u) |
| Am | 2'-O-methyladenosine-5'-phosphate |
| Cm | 2'-O-methylcytidine-5'-phosphate |
| Gm | 2'-O-methylguanosine-5'-phosphate |
| Tm | 2'-O-methyl-thymidine-5'-phosphate |
| Um | 2'-O-methyluridine-5'-phosphate |
| Af | 2'-fluoro-2'-deoxy-adenosine-5'-phosphate |
| Cf | 2'-fluoro-2'-deoxy-cytidine-5'-phosphate |
| Gf | 2'-fluoro-2'-deoxy-guanosine-5'-phosphate |
| Tf | 2'-fluoro-2'-deoxy-thymidine-5'-phosphate |
| Uf | 2'-fluoro-2'-deoxy-uridine-5'-phosphate |
| A, C, G, T, U, a, c, g, t, u | underlined: nucleoside-5'-phosphorothioate |
| am, cm, gm, tm, um | underlined: 2-O-methyl-nucleoside-5'-phosphorothioate |

[a] capital letters represent 2'-deoxyribonucleotides (DNA), lower case letters represent ribonucleotides (RNA)

Single-Dose Screen of Nav1.8 siRNAs against mRNA Expression of Transfected Human Nav1.8 in Cos-7 Cells.

All Nav1.8 siRNAs in Table 1 and Table 4 were tested initially at a single dose of 100 nM (Table 1) or 50 nM (Table 4) for activity in reducing mRNA expression of transfected human Nav1.8 in Cos-7 cells. One day before transfection, Cos-7 cells (DSMZ, Braunschweig, Germany) were seeded at $1.5 \times 10^4$ cells/well on 96-well plates (Greiner Bio-One GmbH, Frickenhausen, Germany) in 100 µl of growth medium (Dulbecco's MEM, 10% fetal calf serum, 2 mM L-glutamine, 1.2 µg/ml sodium bicarbonate, 100 u penicillin/100 µg/ml streptomycin, all from Biochrom AG, Berlin, Germany). Four hours prior to siRNA transfection, 20 ng of plasmid/well (Table 1) or 50 ng/well (Table 4) were transfected with Lipofectamine2000 (Invitrogen) as described below for the siRNAs, with the plasmid diluted in Opti-MEM to a final volume of 12.5 µl/well, prepared as a mastermix for the whole plate.

siRNA transfections were performed in triplicate. For each well, 0.5 µl Lipofectamine2000 (Invitrogen GmbH, Karlsruhe, Germany) was mixed with 12 µl Opti-MEM (Invitrogen) and incubated for 15 min at room temperature. For an siRNA concentration of 100 nM in a transfection volume of 100 µl, 2 µl of a 5 µM siRNA were mixed with 10.5 µl Opti-MEM per well, combined with the Lipofectamine2000-Opti-MEM mixture and again incubated for 15 minutes at room temperature. During that incubation time, growth medium was removed from cells and replaced by 75 µl/well of fresh medium. In six wells, growth medium was replaced by 100 µl of fresh medium and cells were lysed immediately by adding lysis mixture, as described below, in order to analyse the background value in the bDNA-assay caused by the Nav1.8-cDNA in the plasmid. siRNA-Lipofectamine2000-complexes were applied completely (25 µl each per well) to the cells and cells were incubated for 24 h at 37° C. and 5% $CO_2$ in a humidified incubator (Heraeus GmbH, Hanau, Germany).

Cells were harvested by applying 50 µl of lysis mixture (from the QuantiGene bDNA-kit from Genospectra, Fremont, USA) to each well and were lysed at 53° C. for 30 min. Afterwards, 50 µl of the lysates were incubated with probesets specific to human Nav1.8 and human GAPDH (sequence of probesets see below) and processed according to the manufacturer's protocol for QuantiGene. Chemoluminescence was measured in a Victor2-Light (Perkin Elmer, Wiesbaden, Germany) as RLUs (relative light units) and values obtained with the human Nav1.8 probeset were normalized to the respective human GAPDH (GAPDH sequence of *Cercopithecus aethiops* so far unknown) values for each well. Values obtained with cells lysed 4 h after plasmid transfection were subtracted from the values obtained with cells lysed 24 h after siRNA transfection. Values acquired with siRNAs directed against Nav1.8 were further normalized relative to the value obtained with an unrelated siRNA (directed against hepatitis C virus) which was set to 100%.

FIG. 1 provides the results from a representative experiment where siRNAs from Table 1 were tested at a single dose of 100 nM and Table 4 provides the results for additional siRNAs at a dose of 50 nM. Several siRNAs (in Tables 1 and 4) were effective at the dose tested in reducing Nav1.8 mRNA levels by at least 50% in COS-7 cells transfected with Nav1.8.

Dose-Response Curves for Selected siRNAs against mRNA Expression of Transfected Human Nav1.8 in Cos-7 Cells Several effective siRNAs against Nav1.8 from the single dose screen (results in FIG. 1) were further characterized by dose response curves. For dose response curves, transfections were performed as for the single dose screen above, but with the following concentrations of siRNA (nM): 100, 33, 11, 3.7, 1.2, 0.4, 1, 0.14, 0.05, 0.015, 0.005 and mock (no siRNA). siRNAs were diluted with Opti-MEM to a final volume of 12.5 µl according to the above protocol.

Three independent dose response experiments were carried out to generate dose response curves (DRCs). The dose response curves were repeated, and a summary of the results are provided in Table 3.

TABLE 3

IC50 values for selected siRNAs targeting Nav1.8

| IC50-values [nM]: | 1st DRC screen | 2nd DRC screen |
|---|---|---|
| AL-DP-6218 | 0.0068 | 0.021 |
| AL-DP-6217 | 0.036 | 0.0021 |
| AL-DP-6050 | 0.013 | 0.16 |
| AL-DP-6209 | 0.060 | 0.012 |
| AL-DP-6042 | nd | 0.016 |
| AL-DP-6049 | 0.24 | 0.0010 |
| AL-DP-6219 | 0.13 | 0.0069 |
| AL-DP-6223 | 73140 | 22 |
| AL-DP-6225 | 0.70 | 8.07 |

Specificity Testing of the Nav1.8 siRNAs against Nav1.5 MRNA

Nav1.5 is an NaV subtype that is closely related to Nav1.8, but has an important role in normal cardiac function. Therefore, it is important to confirm that siRNAs selective for Nav1.8 do not inhibit Nav1.5 expression. Several siRNAs were tested for specificity towards Nav1.8 by transfecting SW620 cells, which express endogenous human Nav1.5, with these siRNAs, and assessing Nav1.5 mRNA levels. A control unrelated siRNA (AL-DP-5002) was also transfected into SW620 cells. siRNAs targeting Nav1.8 were tested at the following doses: 1200 nM, 400 nM, 133.3 nM, 44.4 nM, 14.8 nM, 4.9 nM, 1.6 nM, and mock (without siRNA). One siRNA targeting Nav1.8 (AL-DP-6217) was tested at 1 nM, 10 nM, 100 nM and 1 uM. The expression of Nav1.5 mRNA, which encodes the protein with the highest homology to Nav1.8 in the Nav-family, was then quantified.

One day before transfection, SW620 cells (LCG Promochem, Wesel, Germany) were seeded at $1.5 \times 10^4$ cells/well on 96-well plates (Greiner Bio-One GmbH, Frickenhausen, Germany) in 100 µl of growth medium (Leibowitz L-15 Medium, 10% fetal calf serum, 2 mM L-glutamine, 100 u penicillin/ 100 µg/ml streptomycin, all from Biochrom AG, Berlin, Germany).

siRNA transfections were performed in triplicate. For each well, 0.6 µl Oligofectamine (Invitrogen GmbH, Karlsruhe, Germany) was mixed with 2.4 µl Opti-MEM (Invitrogen) and incubated for 10 min at room temperature. For an siRNA concentration of 1200 nM in 100 µl transfection volume, 5 µl of 24 µM siRNA was mixed with 12 µl Opti-MEM per well, combined with the Oligofectamine-Opti-MEM mixture and again incubated for 20 minutes at room temperature. During that incubation time, growth medium was removed from cells and replaced by 80 µl/well of fresh growth medium without serum. siRNA-Oligofectamine-complexes were applied completely (20 µl each per well) to the cells and cells were incubated for 24 h at 37° C. without $CO_2$ in a humidified incubator (Heraeus GmbH, Hanau, Germany).

Cells were harvested by applying 50 µl of lysis mixture (content of the QuantiGene bDNA-kit from Genospectra, Fremont, USA) to each well and were lysed at 53° C. for 30 min. Afterwards, 50 µl of the lysates were incubated with probesets specific to human Nav1.5 and human GAPDH (sequence of probesets see below) and processed according to the manufacturer's protocol for QuantiGene. Chemoluminescence was measured in a Victor2-Light (Perkin Elmer, Wiesbaden, Germany) as RLUs (relative light units) and values obtained with the human Nav1.5 probeset were normalized to the respective human GAPDH values for each well.

An unrelated control siRNA (directed against hepatitis C virus) was used as a negative control.

Figure 2:
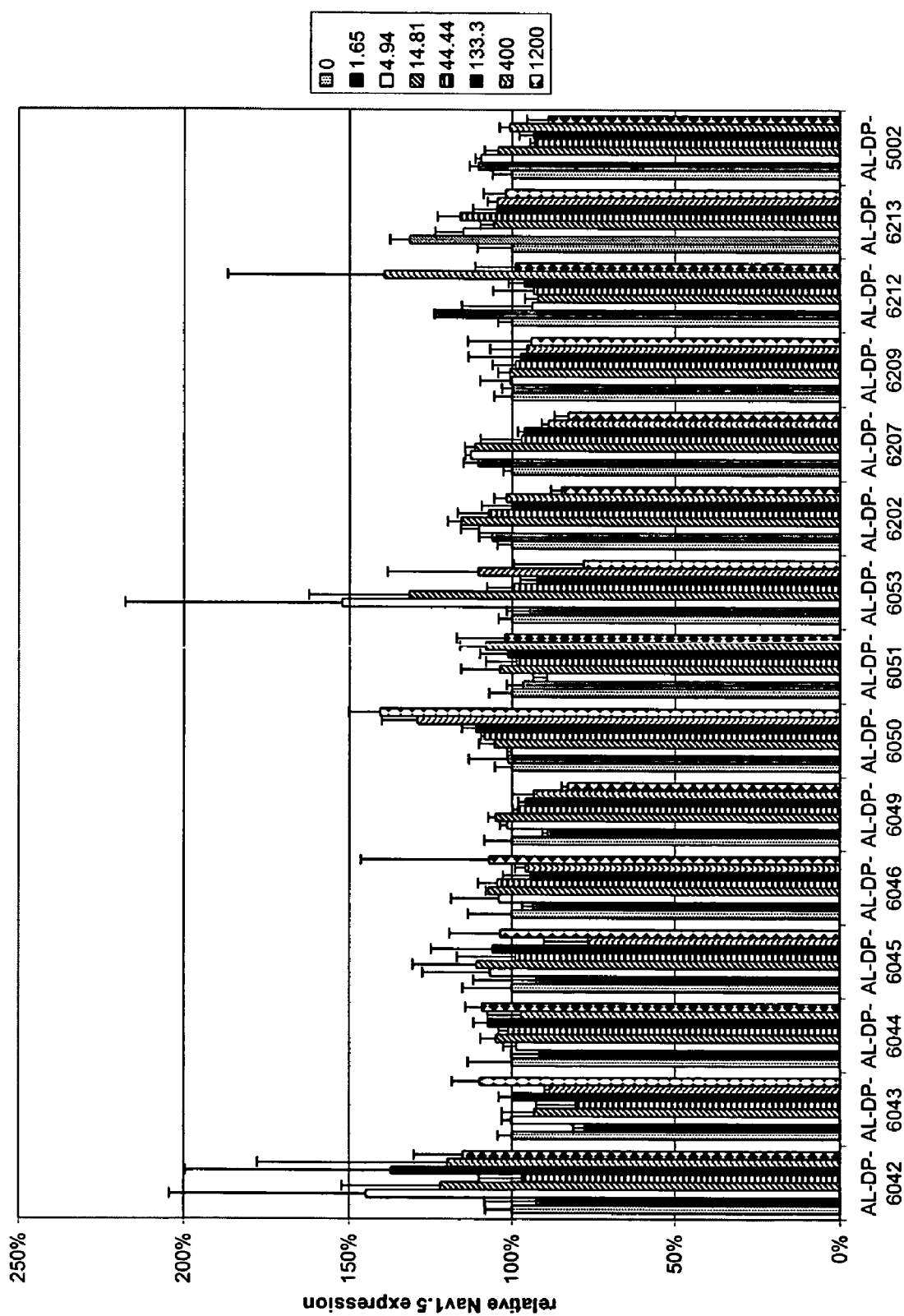
FIG. 2. Lack of cross reactivity of Nav1.8 dsRNAs to endogenous Nav1.5 mRNA in SW620 cells in vitro.

FIG. 2 provides the results. At the concentrations tested, the selected siRNAs targeting Nav1.8, did not exhibit significant dose-dependent inhibition of Nav1.5 mRNA as compared with the unrelated control siRNA (AL-DP-5002), confirming the specificity of these Nav1.8 siRNAs for Nav1.8 over Nav1.5.

In addition, at concentrations up to 1 uM, AL-DP-6217 exhibited no significant inhibition of Nav1.5 mRNA (data not shown), confirming the specificity of this Nav1.8 siRNA for Nav1.8 over Nav1.5.

TABLE 5 bDNA Probesets for the quantitation of human Nav1.8, Nav1.5 and GAPDH

| FPL Name | Function | Sequence | SEQ ID NO: |
|---|---|---|---|
| Human Nav1.8 probeset: | | | |
| hNa182001 | CE | TTTGGAGGTTAAAGGTGATCCATTTTTTCTCTTGGAAAGAAAGT | 543 |
| hNa182002 | CE | GGCGTTTTCCAGAGGCGAGTTTTTCTCTTGGAAAGAAAGT | 544 |
| hNa182003 | CE | CCAGCAGCAGAGAGCCCCTTTTTCTCTTGGAAAGAAAGT | 545 |
| hNa182004 | CE | CTGGGTTGAGGAAGAGGGCTTTTTTCTCTTGGAAAGAAAGT | 546 |
| hNa182005 | CE | AACACTCATTGCCCTTTGGGTTTTTCTCTTGGAAAGAAAGT | 547 |
| hNa182006 | CE | AAGGACGGAGGTTATGATACTGACTTTTTCTCTTGGAAAGAAAGT | 548 |
| hNa182007 | CE | TGTTCAGACTCCTCGAGTTCCTCTTTTTCTCTTGGAAAGAAAGT | 549 |
| hNa182008 | LE | CTATGCCTTCTCTCACTGGCATTTTTTAGGCATAGGACCCGTGTCT | 550 |
| hNa182009 | LE | CTGGTTGTAAGGATCAGAGCGGTTTTTAGGCATAGGACCCGTGTCT | 551 |
| hNa182010 | LE | AACACACTGCCATGACTAGCCCTTTTTAGGCATAGGACCCGTGTCT | 552 |
| hNa182011 | LE | GATGGCTTTCGTGGTCTCCATTTTTAGGCATAGGACCCGTGTCT | 553 |
| hNa182012 | LE | CTGGCCAGCACCCCCACTTTTTAGGCATAGGACCCGTGTCT | 554 |
| hNa182013 | LE | CATGCCTGGAGTCAGGGTTGTTTTTAGGCATAGGACCCGTGTCT | 555 |
| hNa182014 | LE | AGACATCGACAGCTCCAGGGTTTTTAGGCATAGGACCCGTGTCT | 556 |
| hNa182015 | LE | GTCCTGCATCGAATGCCGTTTTTAGGCATAGGACCCGTGTCT | 557 |
| hNa182016 | LE | CAAGCAGGGTGGGCACTTCTTTTTAGGCATAGGACCCGTGTCT | 558 |
| hNa182017 | BL | TGTGGGAGTGGAGAGAGGTTG | 559 |
| hNa182018 | BL | CCCTCTGACACTCTTGGCTTTATT | 560 |
| hNa182019 | BL | GGTGATTTGTTGTCTTCTGTGGAG | 561 |

TABLE 5-continued bDNA Probesets for the quantitation of
human Nav1.8, Nav1.5 and GAPDH

| FPL Name | Function | Sequence | SEQ ID NO: |
|---|---|---|---|
| hNa182020 | BL | GCCTAGAAAAGACATCCTGCG | 562 |
| hNa182021 | BL | GCCAGGGGACCGGAAATGG | 563 |
| hNa182022 | BL | CCCTCAGGGAGTGAGATATCTCG | 564 |
| hNa182023 | BL | GGAAAGACTCCATCATCTGTGACT | 565 |
| hNa182024 | BL | TCTAGGGAGGGGGCCTTG | 566 |
| hNa182025 | BL | GCGGTTGGTGTTCATCTTCTC | 567 |
| hNa182026 | BL | GCAAGCTCACTAGTGGGCG | 568 |
| hNa182027 | BL | TCTGCTGACAAGAAAGTCTTCTTTT | 569 |
| hNa182028 | BL | CCCGGAAAGGTTCATCTAAGTAT | 570 |
| Human GAPDH probeset: | | | |
| hGAP001 | CE | GAATTTGCCATGGGTGGAATTTTTCTCTTGGAAAGAAAGT | 571 |
| hGAP002 | CE | GGAGGGATCTCGCTCCTGGATTTTTCTCTTGGAAAGAAAGT | 572 |
| hGAP003 | CE | CCCCAGCCTTCTCCATGGTTTTTTCTCTTGGAAAGAAAGT | 573 |
| hGAP004 | CE | GCTCCCCCCTGCAAATGAGTTTTTCTCTTGGAAAGAAAGT | 574 |
| hGAP005 | LE | AGCCTTGACGGTGCCATGTTTTTAGGCATAGGACCCGTGTCT | 575 |
| hGAP006 | LE | GATGACAAGCTTCCCGTTCTCTTTTTAGGCATAGGACCCGTGTCT | 576 |
| hGAP007 | LE | AGATGGTGATGGGATTTCCATTTTTTAGGCATAGGACCCGTGTCT | 577 |
| hGAP008 | LE | GCATCGCCCCACTTGATTTTTTTTAGGCATAGGACCCGTGTCT | 578 |
| hGAP009 | LE | CACGACGTACTCAGCGCCATTTTTAGGCATAGGACCCGTGTCT | 579 |
| hGAP010 | LE | GGCAGAGATGATGACCCTTTTGTTTTTAGGCATAGGACCCGTGTCT | 580 |
| hGAP011 | BL | GGTGAAGACGCCAGTGGACTC | 581 |
| Human Nav1.5 probeset: | | | |
| hNa15001 | CE | CGTTTTCTCCTCTTGCTTCTTCTCTTTTTCTCTTGGAAAGAAAGT | 582 |
| hNa15002 | CE | GGGAGCCTGTCCTCCCCATTTTTCTCTTGGAAAGAAAGT | 583 |
| hNa15003 | CE | TCGCCTGCGAAAGGTGAATTTTTCTCTTGGAAAGAAAGT | 584 |
| hNa15004 | CE | CTCTCGCTCTCCCCCGCTTTTTCTCTTGGAAAGAAAGT | 585 |
| hNa15005 | CE | CCGGGACTGGGCTGTCCTTTTTCTCTTGGAAAGAAAGT | 586 |
| hNa15006 | CE | TTTTGCCATGGAGGGCGTTTTTTCTCTTGGAAAGAAAGT | 587 |
| hNa15007 | LE | GGCTGAGATGATTCATTGCTCTGTTTTTAGGCATAGGACCCGTGTCT | 588 |
| bNa15008 | LE | GCTGAGGCCACGGGTGATTTTTAGGCATAGGACCCGTGTCT | 589 |
| bNa15009 | LE | AATGCTCCCGCGGCTGGTTTTTAGGCATAGGACCCGTGTCT | 590 |
| hNa15010 | LE | CTGGGCACTGGTCCGGCTTTTTAGGCATAGGACCCGTGTCT | 591 |
| hNa15011 | LE | GGCCAGGAGCCGAGGTTTTTTAGGCATAGGACCCGTGTCT | 592 |
| bNa15012 | LE | CCCAGTAATGAGACCACCCCATTTTTAGGCATAGGACCCGTGTCT | 593 |
| hNa15013 | LE | CCTCTGGGTCGCCTGCCTTTTTAGGCATAGGACCCGTGTCT | 594 |
| hNa15014 | BL | CACTCCTCAGTTCCTGAAGACATC | 595 |

TABLE 5-continued bDNA Probesets for the quantitation of
human Nav1.8, Nav1.5 and GAPDH

| FPL Name | Function | Sequence | SEQ ID NO: |
|---|---|---|---|
| hNa15015 | BL | GGACCATCTTCTGAGTCAGACTTG | 596 |
| hNa15016 | BL | AACGTGGCTTCATAGAAGTCCT | 597 |
| hNa15017 | BL | AATCTGCTTCAGAACCCAGGTC | 598 |
| hNa15018 | BL | TGTGCTGTTTTCATCATCTGCAA | 599 |
| hNa15019 | BL | CCAGCAGTGATGTGTGGTGG | 600 |
| hNa15020 | BL | GCAGGGGCCAGGGCA | 601 |
| hNa15021 | BL | TGCAGTCCACAGTGCTGTTCT | 602 |
| hNa15022 | BL | GGCTTCCTGGGGATGTGG | 603 |

Single-Dose Screen of Nav1.8 siRNAs against mRNA Expression of Endogenous Nav1.8 in Primary Cultures of Rat Dorsal Root Ganglion Cells.

To confirm and extend the results obtained on mRNA expression of transfected human Nav1.8 in Cos-7 cells, Nav1.8 siRNAs from Table 1 were tested at a single dose of 200 nM for activity in reducing mRNA expression of endogenous Nav1.8 in primary cultures of rat dorsal root ganglion (DRG) cells.

DRG cells were isolated from Sprague-Dawley rats at postnatal day 3 to 6. DRGs were dissected and cells dissociated into single cells by incubation with 0.28 Wunsch units/ml Liberase Blendzyme (Roche) in S-MEM (Gibco) at 37° C. for 35 min. The cell suspension was pre-plated on tissue-culture plates to remove non-neuronal cells. Neurons were then plated onto tissue-culture Biocoat™ PDL Poly-D-Lysine/Laminin 96-well plates (BD Biosciences, Bedford Mass., USA) in F12-HAM's Medium containing glutamine (Invitrogen Gibco, Carlsbad Calif., USA) with 5% fetal bovine serum (FBS, heat inactivated) and 5% horse serum (heat inactivated) (both Invitrogen Gibco, Carlsbad Calif., USA) supplemented with 50 ng/ml mouse nerve growth factor 2.5S (NGF; Promega Corp., Madison Wis., USA) and kept at 37° C., 5% $CO_2$ in a humidified incubator until transfection.

Nav1.8 siRNAs were screened in DRG cultures at 200 nM in duplicate using TransMessenger™ Transfection reagent (Qiagen GmbH, Hilden, Germany, cat. no. 301525) which is based on a lipid formulation, a specific RNA-condensing reagent (Enhancer R™) and an RNA-condensing buffer (Buffer EC-R™), keeping siRNA:Enhancer R™ ratio (µg:µl) constant at 1:2, and siRNA:TransMessenger™ ratio (µg:µl) constant at 1:12.

DRG neurons were transfected 24 h post-plating. For each well, 0.52 µl Enhancer R™ were first mixed with 13.68 µl Buffer EC-R™. 0.8 µl of a 25 µM solution of AL-DP-5987 (0.26 µg) in annealing buffer (20 mM sodium phosphate, pH 6.8; 100 mM sodium chloride), or 0.8 µl of annealing buffer (siRNA-free control) were added and the mixture incubated for 5 min at RT. 3.12 µl TransMessenger™ Transfection Reagent were diluted with 6.88 µl Buffer EC-R™, added to the mixture, and the mixture incubated for another 10 min at room temperature to allow transfection-complex formation. 75 µl serum free F12-HAM's Medium containing glutamine (Invitrogen Gibco, Carlsbad Calif., USA) supplemented with 50 ng/ml NGF 2.5S (Promega Corp., Madison Wis., USA) and 1:50 B27 supplement (Invitrogen Gibco, Carlsbad Calif., USA) were added to the transfection complexes and complete mixing achieved by gently pipetting up and down. The growth medium was removed from the DRG cells, and 90 µl of the above transfection complex mixture were added onto the cells. After 7 to 8 h of incubation at 37° C., 5% $CO_2$ in a humidified incubator supernatant was removed from the cells, fresh F12-HAM's medium containing glutamine supplemented with 5% FBS, 5% horse serum (both Invitrogen Gibco, Carlsbad Calif., USA), 50 ng/ml mouse NGF 2.5S (Promega Corp., Madison Wis., USA) and 1:100 Penicillin/Streptomycin (Invitrogen Gibco, Carlsbad Calif., USA) was added, the cells were incubated for another 16 h at 37° C., 5% $CO_2$ in a humidified incubator, and Nav1.8 mRNA was quantified.

Nav1.8 mRNA levels were measured using the QuantiGene™ bDNA kit (Genospectra, Fremont, USA) according to manufacturer's protocol. Briefly, the supernatant was removed from the DRG cells, and the cells were lysed by addition of 150 µl of Lysis Working Reagent (1 volume of Lysis Mixture plus 2 volumes of medium) and incubation at 52° C. for 30min. 40 µl of the lysates were incubated at 52° C. for 40 min with the probe sets specific to rat Nav1.8 and mouse synuclein (SNCL). Chemoluminescence was read on a Victor$^2$-Light™ (PerkinElmer Life And Analytical Sciences, Inc., Boston Mass., USA) as Relative Light Units (RLU). RLU for Nav1.8 were normalized to SNCL RLU for each well. Normalized Nav1.8/SNCL ratios were then compared to the siRNA-free control, which was set as 100%.

Figure 3:
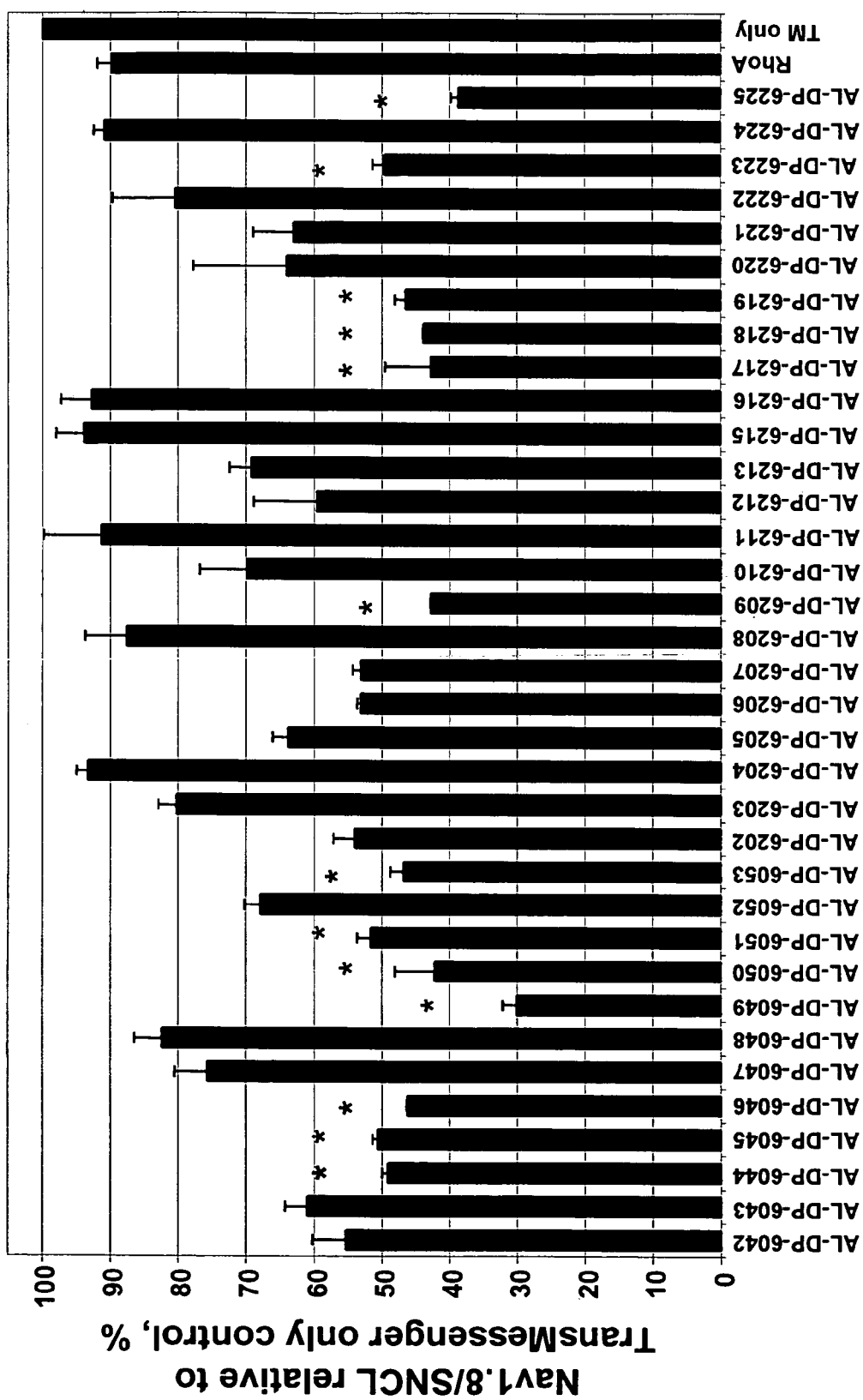
FIG. 3. In vitro activity of the dsRNAs provided in Table 1 against endogenous Nav1.8 mRNA in primary cultures of rat dorsal root ganglion cells.

FIG. 3 provides the results. At 200 nM, at least 13 (indicated by '*') of the Nav1.8 siRNAs tested showed at least 50% Nav1.8 mRNA knock down compared to the siRNA-free control (TransMessenger™ only; TM only), while an unrelated control siRNA against RhoA had no effect.

Dose Response of dsRNA AL-DP-6209 against MRNA Expression of Endogenous Nav1.8 in Primary Cultures of Rat Dorsal Root Ganglion Cells One effective siRNA (AL-DP-6209) against Nav1.8 from the single dose screen in primary cultures of rat dorsal root ganglion cells was further characterized for dose dependence. For the dose response curve, experiments were performed as for the single dose screen in DRG cultures above, but with the following concentrations of siRNA: 175, 88, 44, 22, 11 and 5.5 nM. For all siRNA concentrations, siRNA:Enhancer R ratio (ug:ul) was kept constant at 1:2 and siRNA:TransMessenger ratio (ug/ul) was kept constant at 1:12 (FIG. 4).

Figure 4:
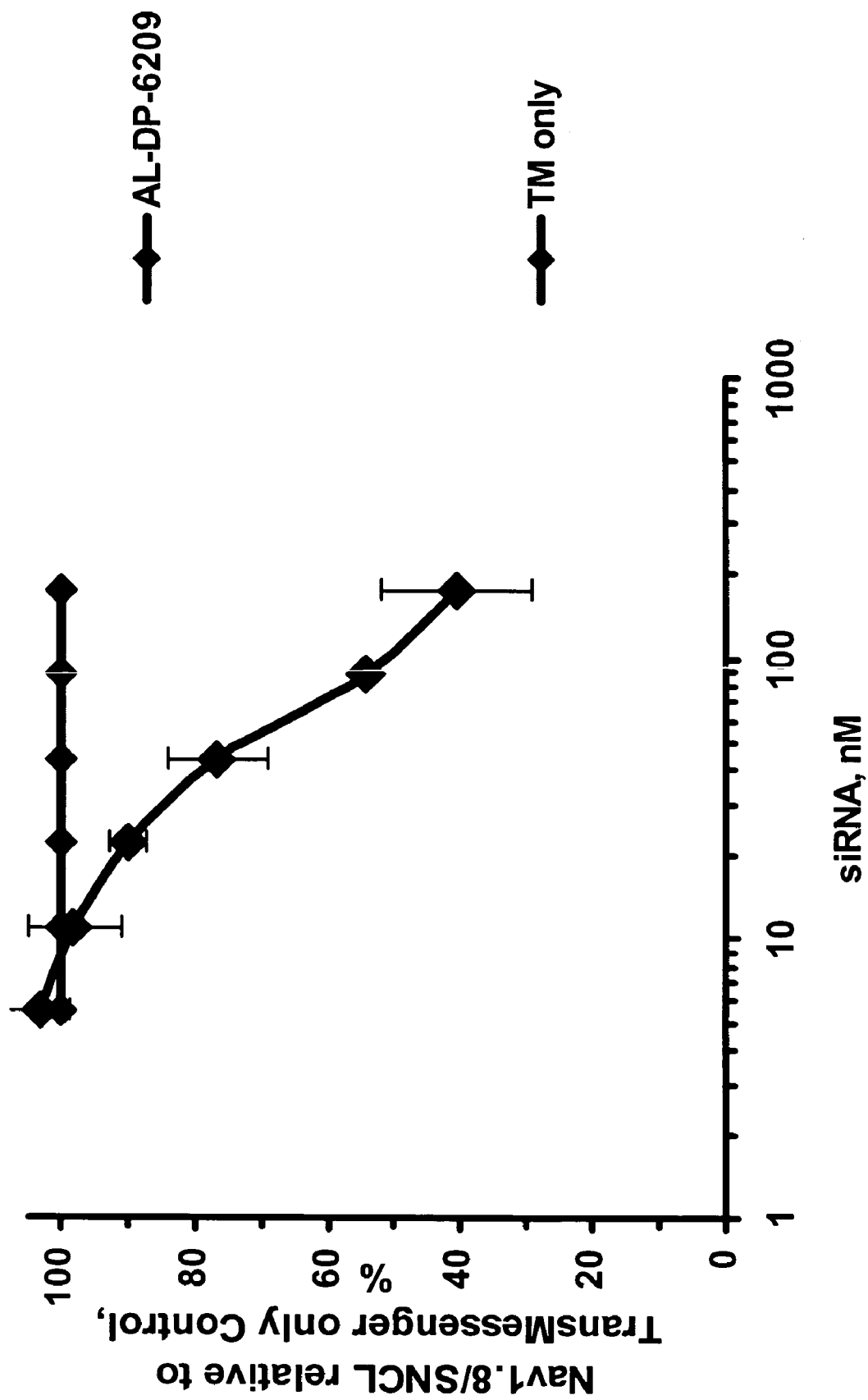
FIG. 4. Dose response of dsRNA AL-DP-6209 against endogenous Nav1.8 mRNA in primary cultures of dorsal root ganglion cells FIG. 5. In vivo efficacy of dsRNA AL-DP-6209 with iFECT against complete Freund's adjuvant—induced tactile hyperalgesia in rats.

FIG. 4 provides the result for the selected siRNA AL-DP-6209 from a dose response experiment. At 5.5 and 11 nM, AL-DP-6209 did not inhibit Nav1.8 mRNA expression relative to SNCL, whereas at 88 and 175 nM, AL-DP-6209 inhibited Nav1.8 mRNA expression relative to SNCL by >40%. Maximal inhibition of Nav1.8 mRNA expression relative to SNCL occurred in this experiment at 175 nM.

Figure 5:
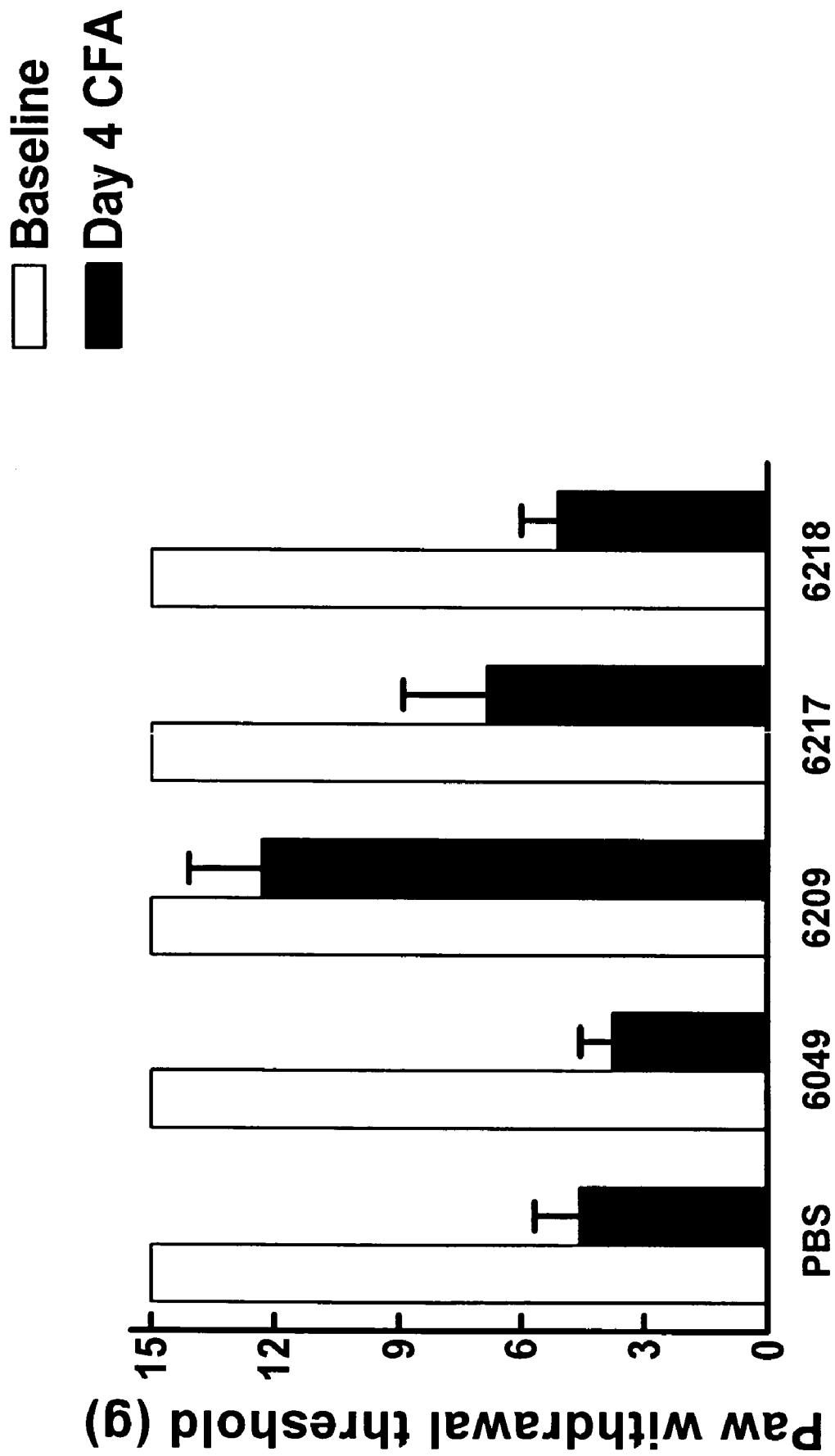

Intrathecal Bolus Administration of siRNAs against Nav1.8 with iFECT Prevents Inflammatory Pain The effect of siRNAs against Nav1.8, formulated with iFECT, on complete Freund's adjuvant-induced tactile hypersensitivity was evaluated in rats (FIG. 5). Adult male Sprague-Dawley rats received an injection of CFA (150 uL) into the hindpaw on day 0. siRNAs against Nav1.8 were then administered by intrathecal bolus to the lumbar region of the spinal cord on days 1, 2 and 3; specifically, for each bolus injection, 2 ug of siRNA was complexed with iFECT transfection reagent (Neuromics, Minneapolis Minn., USA) at a ratio of 1:4 (w:v) in a total volume of 10 uL. Five groups of rats (with 5 rats per group) were treated with either siRNA (AL-DP-6049, AL-DP-6209, AL-DP-6217 or AL-DP-6218; Table 1), or PBS, in the presence of iFECT. Tactile hypersensitivity was expressed as tactile withdrawal thresholds which were measured by probing the hindpaw with 8 calibrated von Frey filaments (Stoelting, Wood Dale Ill., USA) (0.41 g to 15 g). Each filament was applied to the plantar surface of the paw. Withdrawal threshold was determined by sequentially increasing and decreasing the stimulus strength and calculated with a Dixon non-parametric test (see Dixon, W. J. (1980) "Efficient analysis of experimental observations" Annu Rev Pharmacol Toxicol 20:441-462; Chaplan, S. R., F. W. Bach, et al.(1994) "Quantitative assessment of tactile allodynia in the rat paw" J Neurosci Methods 53:55-63). Tactile thresholds were measured before CFA injection to assess baseline thresholds, and then on day 4 after CFA and treatment with test articles. In rats treated with PBS, tactile hypersensitivity was pronounced on day 4, as evidenced by reduced paw withdrawal threshold, as expected. In rats treated with AL-DP-6209, tactile thresholds were nearly normalized on day 4, demonstrating that the Nav1.8 siRNA, AL-DP-6209, is efficacious in vivo against inflammation-induced hyperalgesia. Treatment with the Nav1.8 siRNA, AL-DP-6217, resulted in the average tactile threshold trending towards baseline, with one of five rats demonstrating a normal tactile response. AL-DP-6049 and AL-DP-6218 did not significantly alter tactile thresholds compared to PBS treatment, in this experimental paradigm.

These results demonstrate that siRNAs targeting Nav1.8, formulated with transfection reagent and administered intrathecally, alleviate CFA-induced tactile hyperalgesia, and therefore represent a novel approach to providing effective treatment of clinical inflammatory pain.

Figure 6:
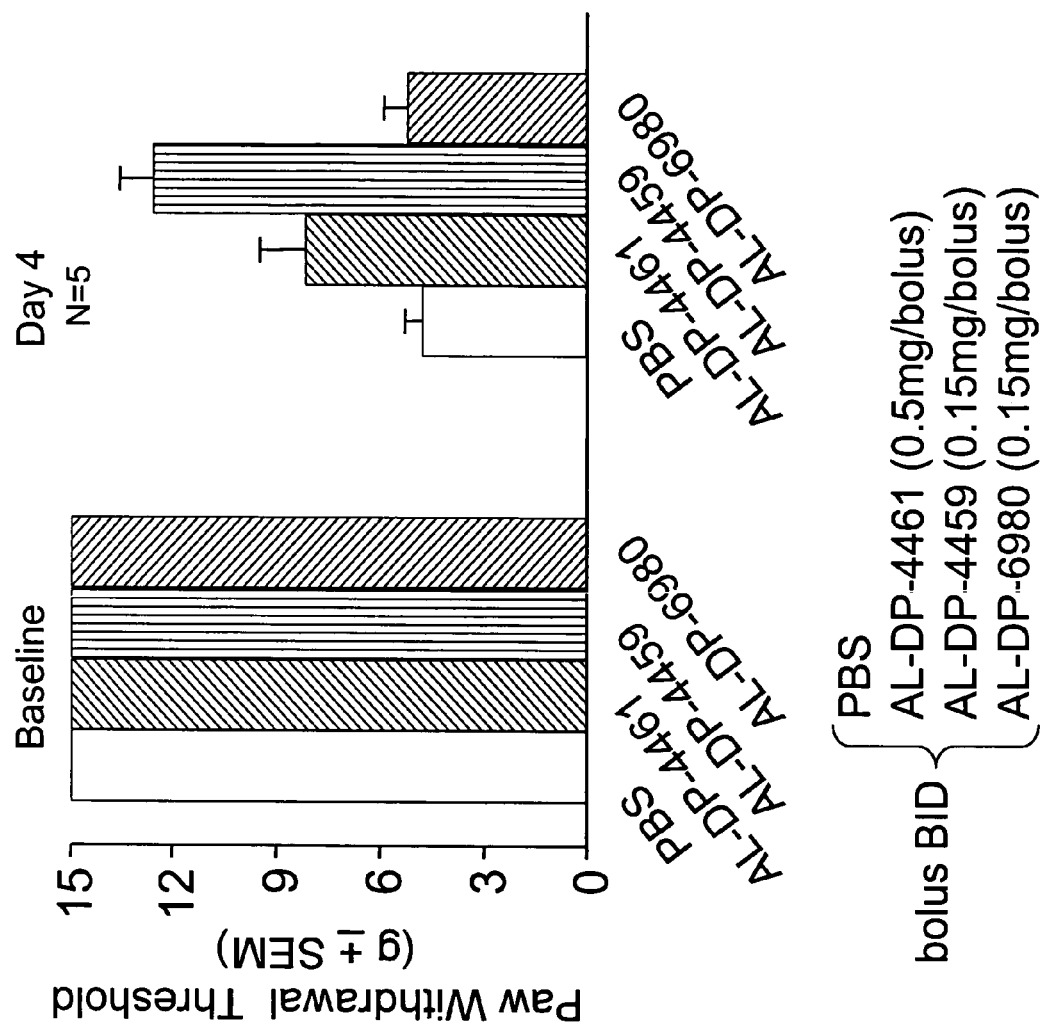
FIG. 6. In vivo efficacy of dsRNA AL-DP-4459 and AL-DP-4461 against complete Freund's adjuvant—induced tactile hyperalgesia in rats.

Intrathecal Bolus Administration of siRNAs against Nav1.8 without Transfection Reagent Alleviates Inflammatory Pain The effect of siRNAs against Nav1.8, formulated in phosphate buffered saline (PBS), on complete Freund's adjuvant (CFA)—induced tactile hypersensitivity was evaluated in rats (FIG. 6). Of 3 Nav1.8 siRNAs tested, 2 siRNAs were efficacious against CFA-induced tactile hypersensitivity: AL-DP-4461, an unconjugated siRNA with different chemical modifications but the same sequence as AL-DP-6050, and AL-DP-4459, a cholesterol-conjugated siRNA with the same chemical modifications and sequence as AL-DP-6050. With the dosing paradigms evaluated in this experiment, AL-DP-6980 (cholesterol-conjugated siRNA with the same chemical modifications and sequence as AL-DP-6209) was not efficacious against CFA-induced tactile hypersensitivity. The sequences of AL-DP-4461, AL-DP-4459 and AL-DP-6980 are shown in Table 6.

TABLE 6

Further modified siRNAs specific for Nav1.8

| Duplex name | sense strand sequence (5'-3') | SEQ ID NO: | anti-sense strand sequence (5'-3') | SEQ ID NO: |
|---|---|---|---|---|
| AL-DP-4461 | cauccuaugaaccaauagceTeT | 604 | gcuauugguucauaggaugeceT | 605 |
| AL-DP-4459 | cmaumcmcmumaumgaacmcmaa umagcmTT-sChol | 606 | gcumauugguucmaumaggaugTT | 607 |
| AL-DP-6980 | umumumumgumcmumaaaumgag umumcmaTT-sChol | 608 | ugaacucmauuumagacmaaaaTT | 609 |

Note:
Prefix e represents 2'-O-(2-methoxyethyl) modified nucleotides

Adult male Sprague-Dawley rats received an injection of CFA into the hindpaw on day 0. Four groups of rats (with 5 rats per group) were treated starting on day 1 after CFA injection with either siRNA against Nav1.8 (AL-DP-4461, AL-DP-4459, or AL-DP-6980), or PBS. siRNAs against Nav1.8 (AL-DP-4461, AL-DP-4459 or AL-DP-6980) or PBS were administered by intrathecal bolus injections (10 uL per injection) to the lumbar level of the spinal cord twice per day (BID) on days 1, 2 and 3. Tactile hypersensitivity was measured as above, both before CFA injection to assess baseline thresholds, and then on day 4 after CFA and treatment with test articles. In rats treated with PBS, tactile hypersensitivity was pronounced on day 4, as evidenced by reduced paw withdrawal threshold, as expected. In rats treated with AL-DP-4461 by bolus BID (0.5 mg/bolus), tactile thresholds were moderately normalized on day 4, demonstrating that the Nav1.8 siRNA, AL-DP-4461, is moderately efficacious with this dosing paradigm in vivo against CFA-induced tactile hyperalgesia. Treatment with the Nav1.8 siRNA, AL-DP-4459, by bolus BID (0.15 mg/bolus), resulted in nearly complete normalization of tactile threshold, with all 5 rats demonstrating substantial recovery of tactile thresholds to more than 10.2 g by day 4. In contract, the Nav1.8 siRNA AL-DP- 6980, by bolus BID (0.15 mg/bolus), did not affect tactile hypersensitivity, showing that not all cholesterol-conjugated siRNAs against a target are equally efficacious or potent, even if efficacious when transfected into cultured cells.

These results suggest that cholesterol conjugation enhances in vivo efficacy of siRNAs for neurological disorders, including chronic pain. Furthermore, these results demonstrate that siRNAs targeting Nav1.8, either with or without cholesterol-conjugation, formulated in saline and administered intrathecally by bolus injection, alleviate CFA-induced tactile hyperalgesia, and therefore represent a novel approach to providing effective treatment of clinical inflammatory pain.

Figure 7:
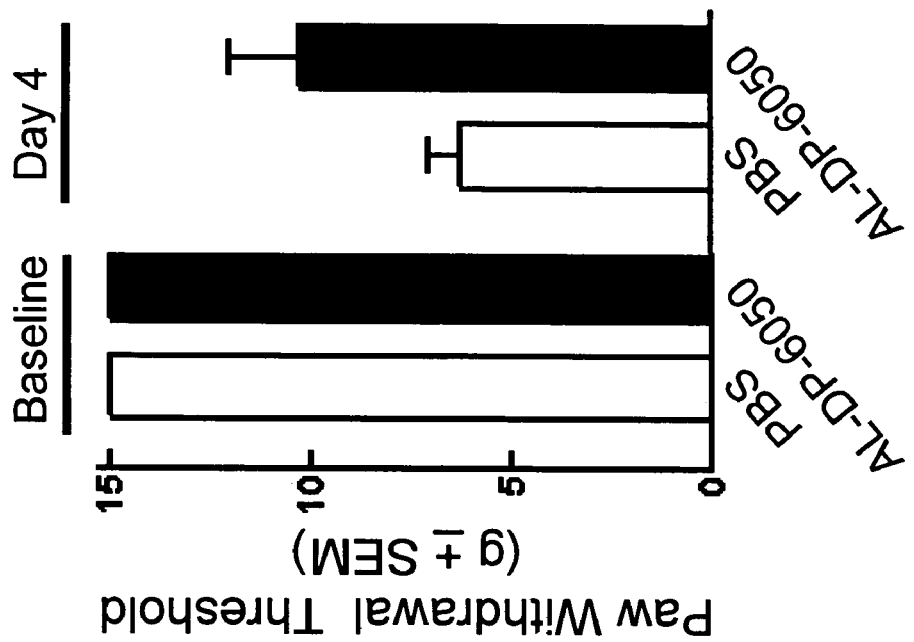
FIG. 7. In vivo efficacy of dsRNA AL-DP-6050 against complete Freund's adjuvant—induced tactile hyperalgesia in rats.
Figure 7:
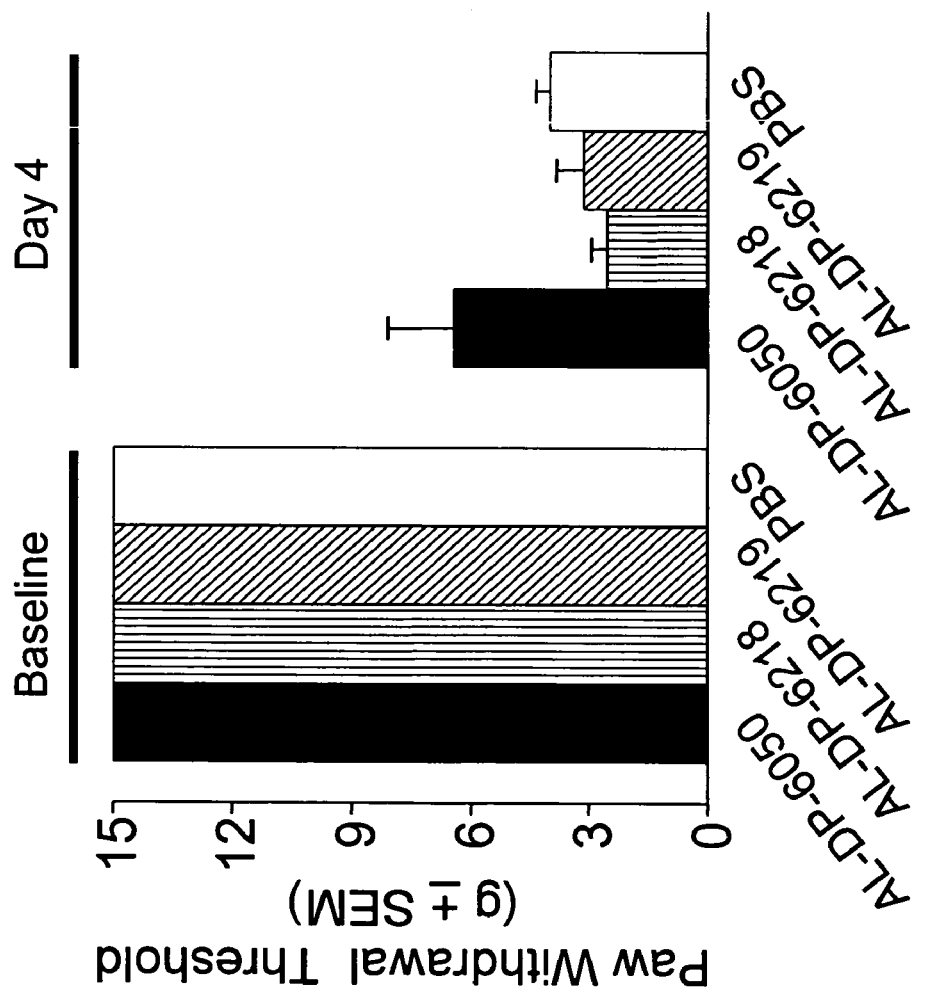

Intrathecal Pump or Bolus Administration of siRNAs against Nav1.8 without Transfection Reagent Alleviates Inflammatory Pain The effect of siRNAs against Nav1.8, formulated in phosphate buffered saline (PBS), on complete Freund's adjuvant (CFA)—induced tactile hypersensitivity was evaluated in rats after intrathecal pump infusion (FIG. 7, left) or intrathecal BID bolus injection (FIG. 7, right). Of 3 Nav1.8 siRNAs tested by continuous intrathecal pump infusion at 0.4 mg/day, 1 siRNA (AL-DP-6050, Table 1) was modestly efficacious against CFA-induced tactile hypersensitivity. AL-DP-6050, when tested by intrathecal BID bolus injection at 0.5 mg/bolus, was efficacious against CFA-induced tactile hypersensitivity.

For evaluating effects of siRNAs against NaV1.8 with continuous intrathecal pump infusion, adult male Sprague-Dawley rats received an injection of CFA into the hindpaw on day 0. Four groups of rats (with 5 rats per group) were treated starting on day 1 after CFA injection with either siRNA against Nav1.8 (AL-DP-6050, AL-DP-6218, or AL-DP-6219), or PBS. In all rats, test articles were intrathecally administered by continuous osmotic mini-pump infusion with an infusion rate of 0.5 uL/hour, beginning on day 1. siRNAs were infused at 0.4 mg/day. Tactile hypersensitivity was measured as above, both before CFA injection to assess baseline thresholds, and then on day 4 after CFA and treatment with test articles (FIG. 7, left). In rats treated with PBS, tactile hypersensitivity was pronounced on day 4, as evidenced by reduced paw withdrawal threshold, as expected. In rats treated with AL-DP-6050 by continuous intrathecal pump infusion (0.4 mg/day), tactile thresholds were modestly normalized on day 4, demonstrating that the Nav1.8 siRNA, AL-DP-6050, is modestly efficacious with this dosing paradigm in vivo against inflammatory pain.

For evaluating effects of siRNAs against NaV1.8 with BID intrathecal bolus injection, adult male Sprague-Dawley rats received an injection of CFA into the hindpaw on day 0. Two groups of rats (with 4 to 5 rats per group) were treated starting on day 1 after CFA injection with either siRNA against Nav1.8 (AL-DP-6050, 0.5 mg/bolus) or PBS. Tactile hypersensitivity was assessed as described above. Tactile thresholds were measured before CFA injection to assess baseline thresholds, and then on day 4 after CFA injection and treatment with test articles (FIG. 7, right). As expected, in rats treated with PBS, tactile hypersensitivity was pronounced on day 4, as evidenced by reduced paw withdrawal threshold. In rats treated with AL-DP-6050 by BID intrathecal bolus injection (0.5 mg/bolus), tactile thresholds were substantially normalized on day 4, demonstrating that the Nav1.8 siRNA, AL-DP-6050, is modestly efficacious with this dosing paradigm in vivo against inflammatory pain.

These results further demonstrate that siRNAs targeting Nav1.8 without cholesterol-conjugation, formulated in saline and administered intrathecally by either bolus injection or continuous pump infusion, alleviate CFA-induced tactile hyperalgesia, and therefore represent a novel approach to providing effective treatment of clinical inflammatory pain.

Figure 8:
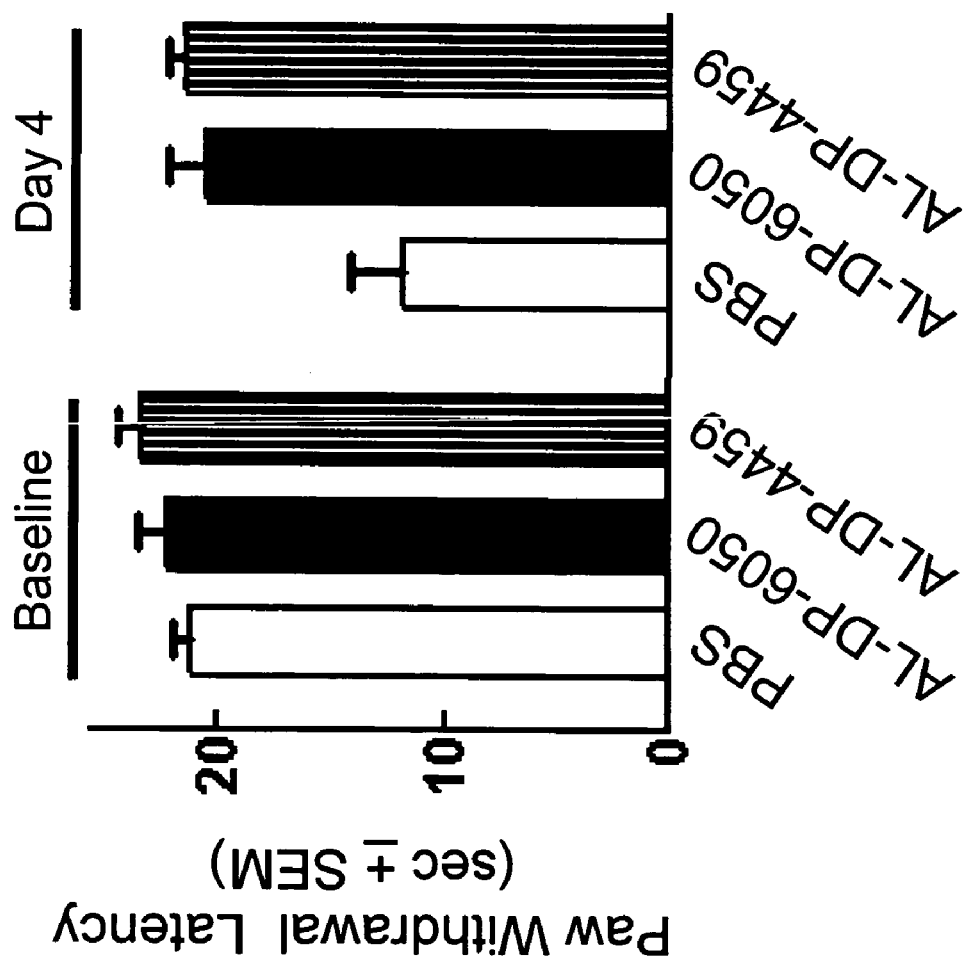
FIG. 8. In vivo efficacy of dsRNAs AL-DP-6050 and AL-DP-4459 against complete Freund's adjuvant—induced thermal hyperalgesia in rats.

Intrathecal Bolus Administration of siRNAs against Nav1.8 without Transfection Reagent Alleviates Inflammatory Pain The effect of siRNAs against Nav1.8, formulated in phosphate buffered saline (PBS), on complete Freund's adjuvant (CFA)—induced thermal hypersensitivity was evaluated in rats (FIG. 8). Both unconjugated dsRNA AL-DP-6050 (Table 1) and cholesterol-conjugated dsRNA AL-DP-4459 (Table 6) were efficacious against CFA-induced thermal hypersensitivity with the BID bolus intrathecal dosing paradigms evaluated.

Adult male Sprague-Dawley rats received an injection of CFA into the hindpaw on day 0. Three groups of rats (with 4 to 5 rats per group) were treated starting on day 1 after CFA injection with either siRNA against Nav1.8 (AL-DP-6050 or AL-DP-4459), or PBS. In all rats, test articles were administered intrathecally by BID bolus injection (10 uL per bolus) beginning on day 1. AL-DP-4459 was dosed at 0.15 mg/bolus whereas AL-DP-6050 was dosed at 0.5 mg/bolus. Thermal hypersensitivity was measured by assessing paw withdrawal latency to a noxious thermal stimulus as described by Hargreaves and colleagues (Hargreaves, K., R. Dubner, et al. (1988) "A new and sensitive method for measuring thermal nociception in cutaneous hyperalgesia" Pain 32:77-88). Latency to withdrawal of a hindpaw in response to noxious radiant heat was determined. A maximal cut-off of 40 sec prevented tissue damage.

Thermal responses were measured before CFA injection to assess baseline thresholds, and then on day 4 after CFA injection and treatment with test articles. As expected, in rats treated with PBS, thermal hypersensitivity was pronounced on day 4, as evidenced by reduced paw withdrawal latency. In rats treated with AL-DP-6050 (0.5 mg/bolus) or AL-DP-4459 (0.15 mg/bolus) by intrathecal BID bolus injection, thermal latencies were normalized on day 4, demonstrating that the unconjugated Nav1.8 siRNA, AL-DP-6050, and the cholesterol-conjugated Nav1.8 siRNA AL-DP-4459 are efficacious with this dosing paradigm in vivo against inflammatory pain.

These results demonstrate that siRNAs targeting Nav1.8, either with or without cholesterol-conjugation, formulated in saline and administered intrathecally by bolus injection, alleviate CFA-induced thermal hyperalgesia, in addition to tactile hyperalgesia (above), and therefore represent a novel approach to providing effective treatment of multiple types of hyperalgesia in clinical inflammatory pain.

Figure 9:
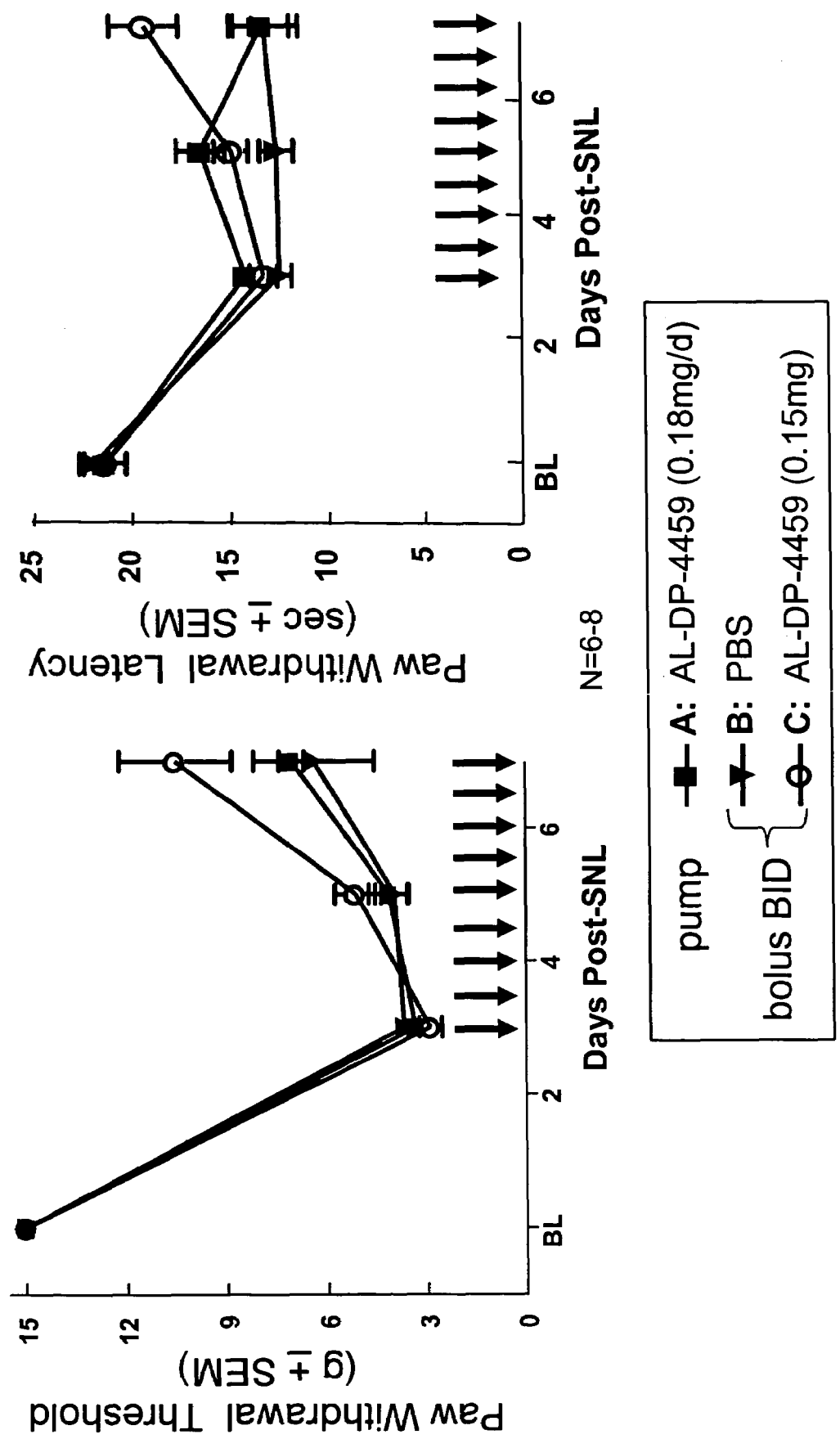
FIG. 9. In vivo efficacy of dsRNA AL-DP-4459 against spinal nerve ligation—induced tactile and thermal hyperalgesia in rats.

Intrathecal Bolus Administration of Cholesterol-Conjugated siRNA against Nav1.8 without Transfection Reagent Alleviates Neuropathic Pain The effect of AL-DP-4459 (Table 6) against Nav1.8, formulated in phosphate buffered saline (PBS), on spinal nerve ligation (SNL)-induced tactile and thermal hypersensitivity was evaluated in rats (FIG. 9). With the bolus intrathecal dosing paradigm evaluated (0.15 mg/bolus, BID), AL-DP-4459 was efficacious against SNL-induced tactile and thermal hypersensitivity.

Adult male Sprague-Dawley rats received unilateral ligation of the L5 and L6 spinal nerves on day 0 (SNL surgery). Three groups of rats (with 6 to 8 rats per group) were treated starting on day 3 after SNL surgery by intrathecal administration of either the siRNA AL-DP-4459 against Nav1.8, or PBS. In 2 of these groups, AL-DP-4459 or PBS was administered by intrathecal bolus injections (5 uL per injection) to the lumbar level of the spinal cord twice per day (BID) on post-SNL days 3 through 7. In one group of rats, AL-DP-4459 was intrathecally administered by continuous osmotic mini-pump infusion at 0.18 mg/day, with an infusion rate of 0.5 uL/hour, on post-SNL days 3 through 7. Tactile and thermal hypersensitivities were assessed as described above.

Tactile (FIG. 9, left) and thermal (FIG. 9, right) responses were measured before SNL surgery to assess baseline responses (BL), and on post-SNL day 3 before treatment with test articles to verify that tactile and thermal hyperalgesia had developed fully. In rats treated with PBS, tactile and thermal hypersensitivities were pronounced, as expected, on post-SNL days 3, 5 and 7 as evidenced by reduced paw withdrawal thresholds and reduced thermal latencies, respectively. The Nav1.8 siRNA AL-DP-4459, when intrathecally administered by continuous pump infusion at 0.18 mg/day, did not affect tactile or hypersensitivity significantly over the timeframe shown. In contrast, in rats treated with AL-DP-4459 by bolus BID (0.15 mg/bolus), tactile thresholds and thermal latencies were substantially normalized on post-SNL day 7 (day 5 of treatment), demonstrating that the Nav1.8 siRNA, AL-DP-4459, is efficacious in vivo against SNL-induced tactile and thermal hyperalgesia.

These results demonstrate that intrathecally administered cholesterol-conjugated siRNAs targeting Nav1.8, formulated in saline, are efficacious against experimental nerve injury-induced chronic pain in rats, and therefore, represent a novel approach to providing effective treatment of clinical neuropathic pain.

Unconjugated and Cholesterol-Conjugated siRNAs Targeting NaV1.8 are Stable in Human Cerebrospinal Fluid at 37° C.

To determine the stability in human cerebrospinal fluid (CSF) of unconjugated and cholesterol-conjugated siRNAs targeting NaV1.8, siRNA duplexes were incubated in human CSF for 48 hours at 37° C., and the single strands were measured by quantitative ion exchange chromatography. In this example, unconjugated siRNAs AL-DP-6050, AL-DP-6209, AL-DP-6217, AL-DP-6218 and AL-DP-6219 (Table 1), and cholesterol-conjugated siRNA AL-DP-4459 (Table 6) were evaluated. 30 µl of human CSF was mixed with 3µl of 50 µM siRNA (150 pmole/well) in a 96-well plate, sealed to avoid evaporation, and incubated for 1 to 48 hours at 37° C. Incubation in 30 µl PBS for 48 hours at 37° C. served as a control for nonspecific degradation. Reactions were stopped by the addition of 4 µl proteinase K (20 mg/ml) and 25µl of proteinase K buffer, and incubation of this mixture for 20 min at 42° C. Samples were spin filtered through a 0.2 µm 96-well filter plate at 3000 rpm for 20 min. Incubation wells were washed with 50 µl Millipore water twice and the combined washing solutions were spin filtered also. A 5 µl aliquot of 50 µM 40-mer RNA was added to each sample to act as an internal standard (IS) for normalization of volume changes in the filtration volume. Samples were analyzed by ion exchange HPLC under denaturing conditions.

1. HPLC System for Analysis of Cholesterol-Conjugated siRNA AL-DP-4459

Column: Dionex DNAPac PA200 (4×250 mm analytical column)

Temp.: 80° C. (denaturing conditions)

Flow: 1 ml/min

Injection: 50 ul

Detection: 260 (reference wavelength 600 nm)

HPLC Eluent A: 25 mM TRIS-HCl; 1 mM EDTA; 50% ACN; pH=8

HPLC Eluent B: 600 mM NaBr in A

Gradient table:

| Time | % A | % B |
|---|---|---|
| 0.00 min | 80 | 20 |
| 1.00 min | 80 | 20 |
| 15.0 min | 30 | 70 |
| 15.5 min | 0 | 100 |
| 17.5 min | 0 | 100 |
| 18.0 min | 80 | 20 |
| 21.0 min | 80 | 20 |

2. HPLC System for unconjugated siRNAs AL-DP-6050, 6209, 6217, 6218, 6219

Column: Dionex DNAPac PA200 (4×250 mm analytical column)

Temp.: 30° C. (denaturing conditions by pH=11)

Flow: 1 ml/min

Injection: 50 ul

Detection: 260 nm (reference wavelength 600 nm)

HPLC Eluent A: 20 mM $Na_3PO_4$ in 10% ACN; pH=11

HPLC Eluent B: 1 M NaBr in A

Gradient table:

| Time | % A | % B |
|---|---|---|
| 0.00 min | 75 | 25 |
| 1.00 min | 75 | 25 |
| 21.0 min | 40 | 60 |
| 21.5 min | 0 | 100 |
| 23.0 min | 0 | 100 |
| 24.5 min | 75 | 25 |
| 28.0 min | 75 | 25 |

Under the denaturing IEX-HPLC conditions, the duplexes eluted as two separated single strands. The internal standard eluted at higher retention times than the single strands of the duplex, and did not interfere with the analysis.

For every injection, the chromatograms were integrated automatically by the Dionex Chromeleon 6.60HPLC software, but were adjusted manually as necessary. All peak areas were corrected by the following equation to the internal standard (IS) peak:

$$CF_{(IS)}=100/PeakArea_{(IS)}; \text{ Corrected } PeakArea_{(s/as)}=CF*PeakArea_{(a/as)}$$

The %-values for the remaining intact FLP at all time points are calculated by the following equation:

$$\%\text{-}FLP_{(s/as)}=(\text{Corrected } PeakArea_{(s/as)}/\text{Corrected } PeakArea_{(s/as); \, t=0min})*100\%$$

All values were normalized to the incubation at t=0 min.

Figure 10:
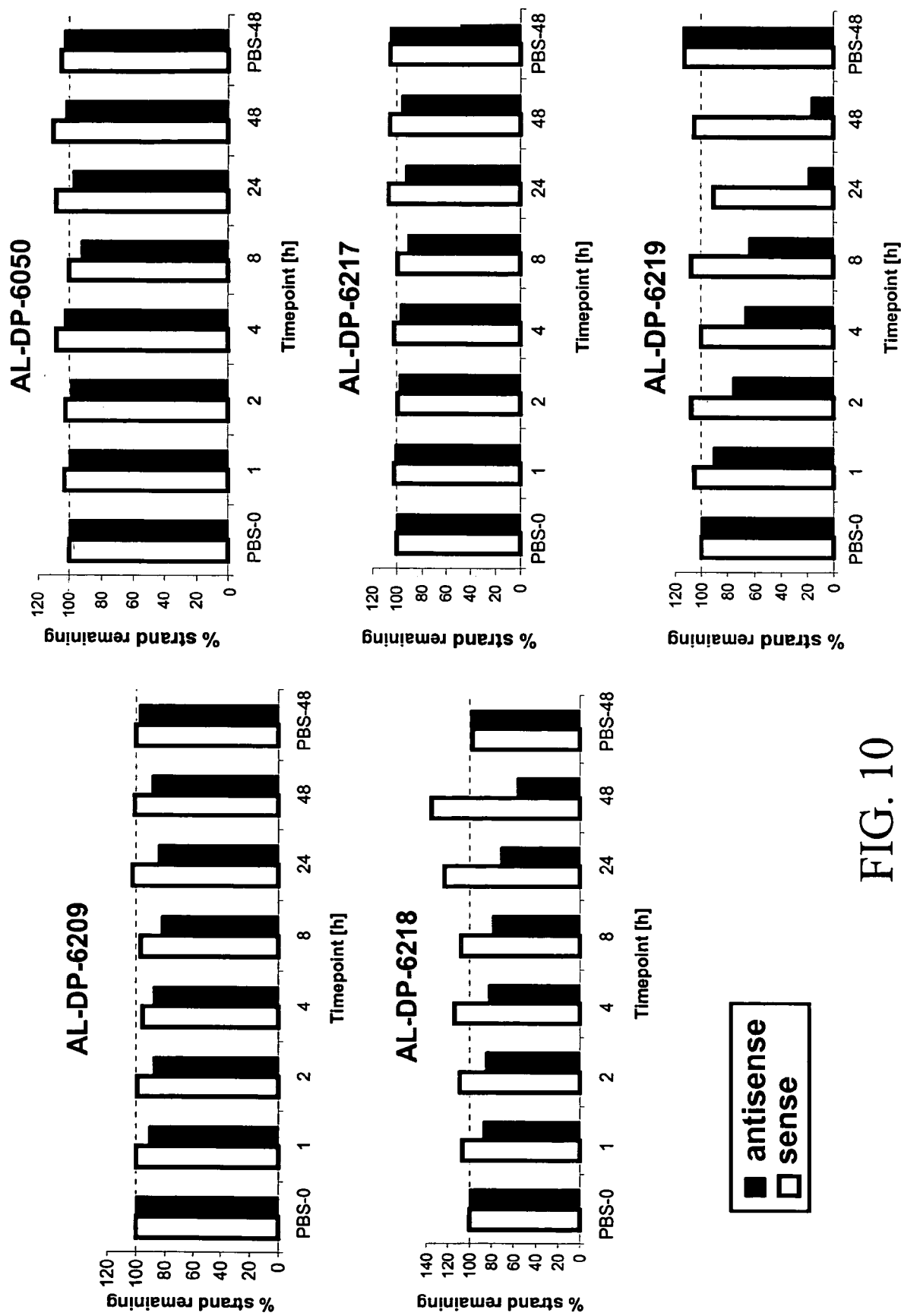
FIG. 10. Stability of unconjugated dsRNAs AL-DP-6050, AL-DP-6209, AL-DP-6217, AL-DP-6218 and AL-DP-6219 in human cerebrospinal fluid at 37° C.
Figure 11:
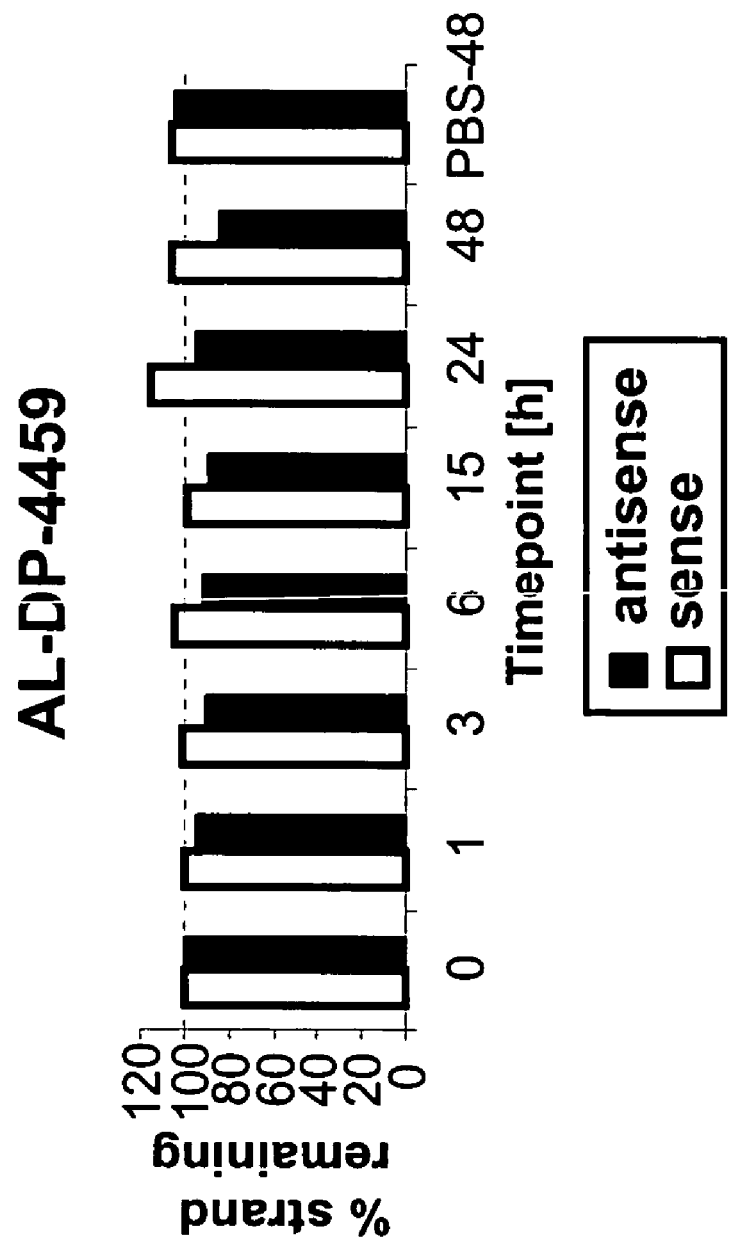
FIG. 11. Stability of cholesterol-conjugated dsRNA AL-DP-4459 in human cerebrospinal fluid at 37° C.

The results for the unconjugated siRNAs are shown in FIG. 10. After 48 hours incubation at 37° C. in PBS (PBS-48), all five siRNAs were completely stable, with no loss detectable. After 48 hours incubation at 37° C. in human CSF, three (AL-DP-6050, AL-DP-6209 and AL-DP-6217) of the five siRNAs exhibited less than 20% loss, whereas two (AL-DP-6218 and AL-DP-6219) of the siRNAs exhibited greater than 50% loss. The results for the cholesterol-conjugated siRNA AL-DP-4459 are shown in FIG. 11. After 48 hours incubation at 37° C. in PBS (PBS-48), AL-DP-4459 was completely stable, with no loss detectable. When assessed for stability in human CSF, AL-DP-4459 was found to be stable at 37° C. for 48 hours, with less than 20% variation detected over this time period.

Unconjugated and Cholesterol-conjugated siRNAs Targeting NaV1.8 Reduce NaV1.8 mRNA in a Dose-dependent Manner in Primary Rat Sensory Neuronal Cultures Another effective siRNA (AL-DP-6050, Table 1) against Nav1.8 from the single dose screen in primary cultures of rat dorsal root ganglion cells and its cholesterol conjugate AL-DP-4459 (Table 6) were further characterized for dose dependence. For the dose response curves, transfections were performed using Lipofectamine 2000 (see below) with the following concentrations of siRNA: 200, 80, 32, 12.8, 5.12, 2.05, 0.82 and 0.33 nM (FIG. 12).

DRG neurons were transfected 24 h post-plating. For each well, 0.4 µl Lipofectamine™ 2000 (Invitrogen Corporation, Carlsbad, Calif.) was used and transfections were performed according to the manufacturer's protocol. Specifically, the siRNA: Lipofectamine™ 2000 complexes were prepared as follows. The appropriate amount of siRNA was diluted in Opti-MEM I Reduced Serum Medium and mixed gently. The Lipofectamine™ 2000 was vortexed before use; then for each well of a 96 well plate, 0.4 ul Lipofectamine™ 2000 was diluted in 25 µl of Opti-MEM I Reduced Serum Medium, mixed gently and incubated for 5 minutes at room temperature. After the 5 minute incubation, 1 ul of the diluted siRNA was combined with the diluted Lipofectamine™ 2000 (total volume, 26.4 µl). The complex was mixed gently and incubated for 20 minutes at room temperature to allow the siRNA: Lipofectamine™ 2000 complexes to form. Then 100 µl of serum-free F12-HAM's Medium containing glutamine (Invitrogen Gibco, Carlsbad Calif., USA) supplemented with 50 ng/ml NGF 2.5S (Promega Corp., Madison Wis., USA) and 1:50 B27 supplement (Invitrogen Gibco, Carlsbad Calif., USA) was added to the transfection complexes, and mixing was achieved by gently pipetting up and down. The growth medium was removed from the DRG cells and 100 µl of the above transfection complex mixture was added to each well of a 96-well plate. After 20 h of incubation at 37° C., 5% $CO_2$ in a humidified incubator, supernatant was removed from the cells, fresh F12-HAM's medium containing glutamine supplemented with 5% FBS, 5% horse serum (both Invitrogen Gibco, Carlsbad Calif., USA), 50 ng/ml mouse NGF 2.5S (Promega Corp., Madison Wis., USA) and 1:100 Penicillin/Streptomycin (Invitrogen Gibco, Carlsbad Calif., USA) was added. The cells were incubated for another 20-24 h at 37° C., 5% $CO_2$ in a humidified incubator, and Nav1.8 mRNA was quantified by the bDNA assay, as described previously.

Figure 12:
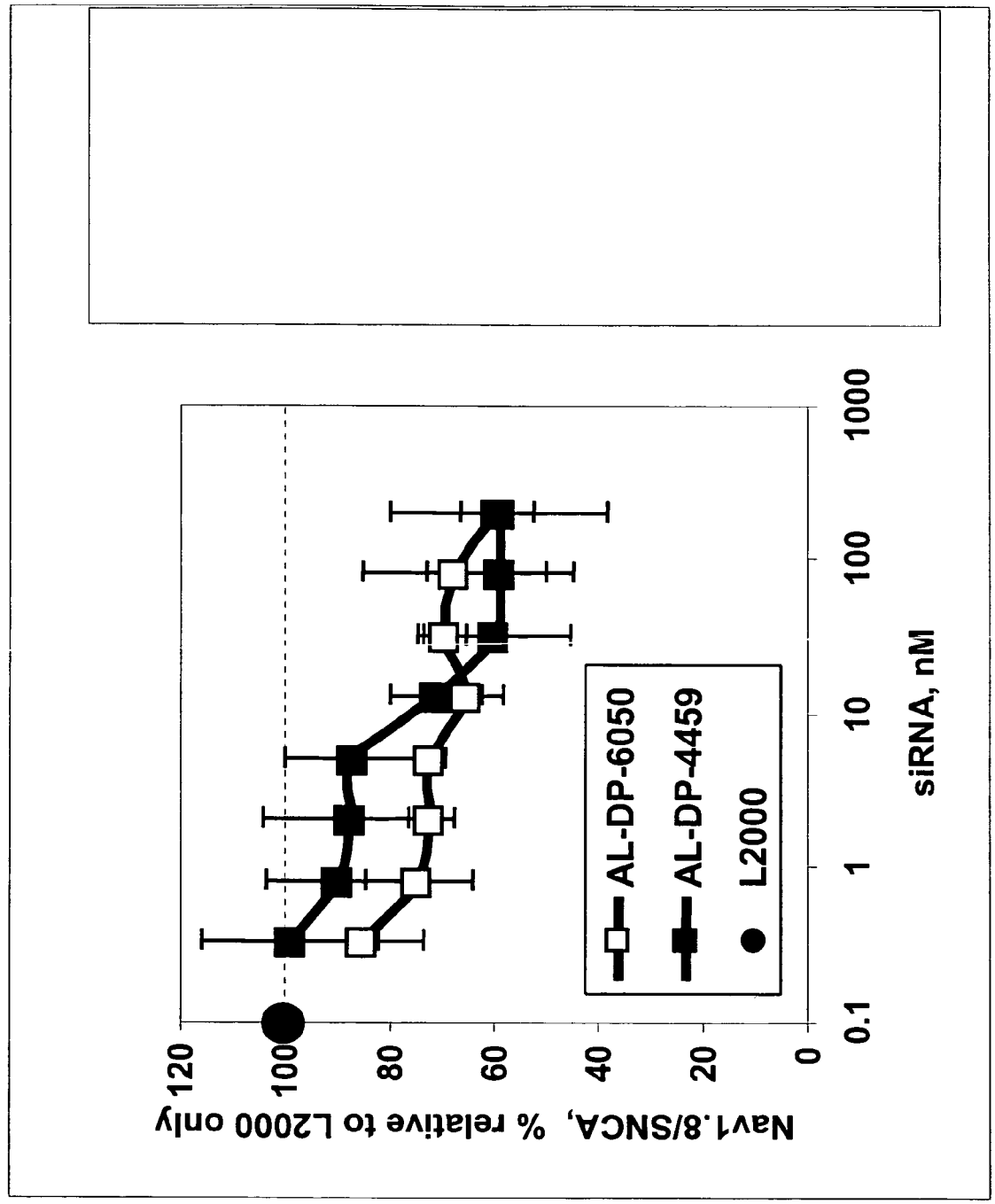
FIG. 12. Dose response of siRNA AL-DP-6050 and its cholesterol conjugate AL-DP-4459 against mRNA expression of endogenous Nav1.8 in primary cultures of rat dorsal root ganglion cells.

FIG. 12 provides the result for the selected siRNA AL-DP-6050 and its cholesterol conjugate AL-DP-4459 from a dose response experiment. AL-DP-6050 and its cholesterol conjugate AL-DP-4459 inhibited Nav1.8 mRNA expression relative to alpha-synuclein (SNCA) in a dose-dependent manner, with maximal inhibitions of ~40% at >30 nM siRNA, in this experiment.

Figure 13:
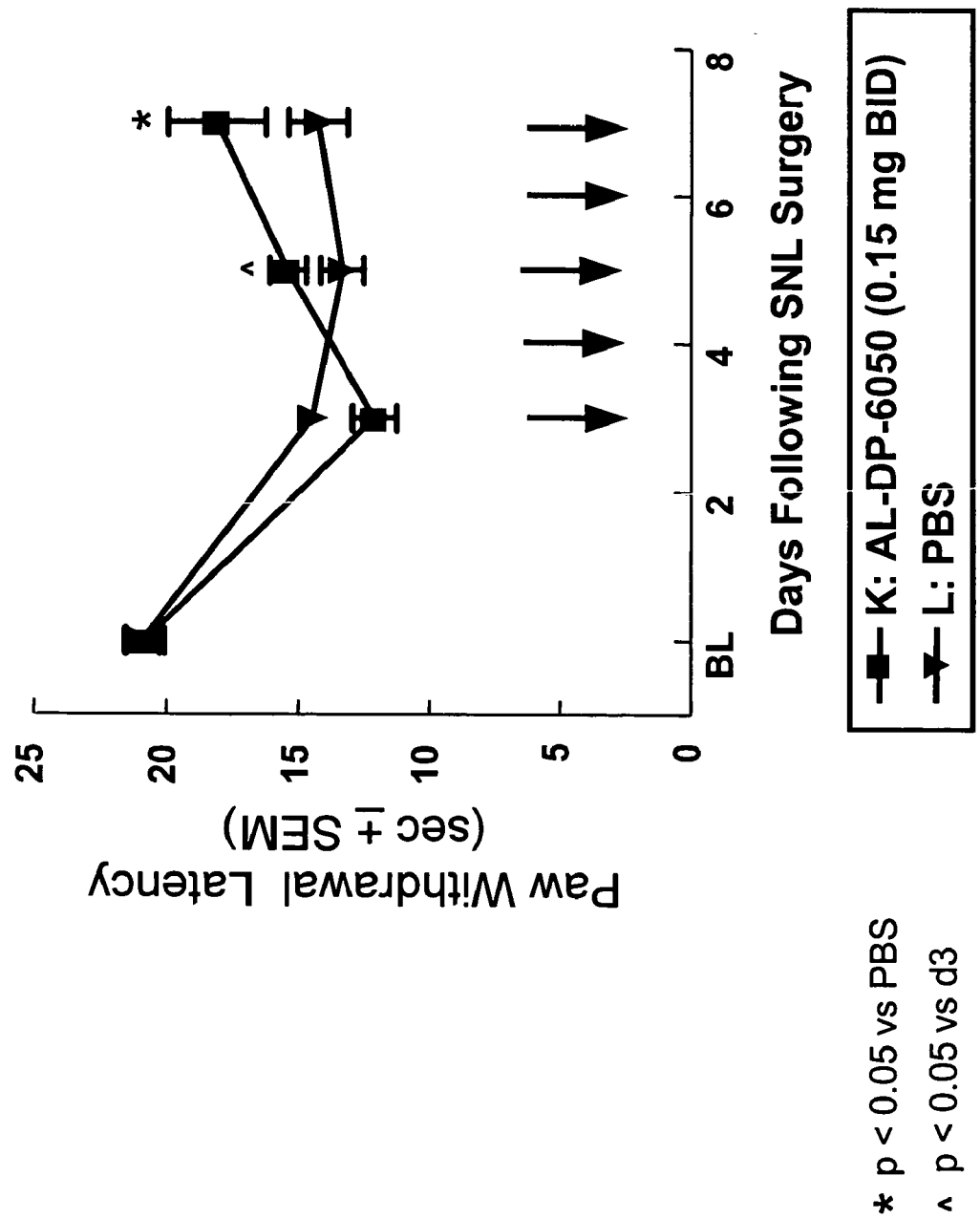
FIG. 13. In vivo efficacy of dsRNA AL-DP-6050 against spinal nerve ligation—induced thermal hyperalgesia in rats.

Intrathecal Bolus Administration of Unconjugated siRNA against Nav1.8 without Transfection Reagent Alleviates Neuropathic Pain The effect of AL-DP-6050 (Table 1) against Nav1.8, formulated in phosphate buffered saline (PBS), on spinal nerve ligation (SNL)—induced thermal hypersensitivity was evaluated in rats (FIG. 13). With the bolus intrathecal dosing paradigm evaluated (0.15 mg/bolus, BID), AL-DP-6050 was efficacious against SNL-induced thermal hypersensitivity.

Adult male Sprague-Dawley rats received unilateral ligation of the L5 and L6 spinal nerves on day 0 (SNL surgery). Two groups of rats (with 8 rats per group) were treated starting on day 3 after SNL surgery by intrathecal bolus injection with either the siRNA AL-DP-6050 against Nav1.8, or PBS. Intrathecal bolus injections (0.15 mg in 5 uL per injection) were administered to the lumbar level of the spinal cord twice per day (BID) on post-SNL days 3 through 7. Thermal hypersensitivity was assessed as described above.

Thermal responses were measured before SNL surgery to assess baseline responses (BL), and on post-SNL day 3 before treatment with test articles to verify that thermal hyperalgesia had developed fully. In rats treated with PBS, thermal hypersensitivity was pronounced, as expected, on post-SNL days 3, 5 and 7 as evidenced by reduced thermal latencies. In contrast, in rats treated with AL-DP-6050 by bolus BID (0.15 mg/bolus), thermal latencies were substantially normalized on post-SNL days 5 (day 3 of treatment) and 7 (day 5 of treatment), demonstrating that the Nav1.8 siRNA, AL-DP-6050, is efficacious in vivo against SNL-induced thermal hyperalgesia.

These results demonstrate that siRNAs targeting Nav1.8, formulated in saline and administered by intrathecal bolus injection, are efficacious against experimental nerve injury-induced chronic pain in rats, and therefore, represent a novel approach to providing effective treatment of clinical neuropathic pain.

Figure 14:
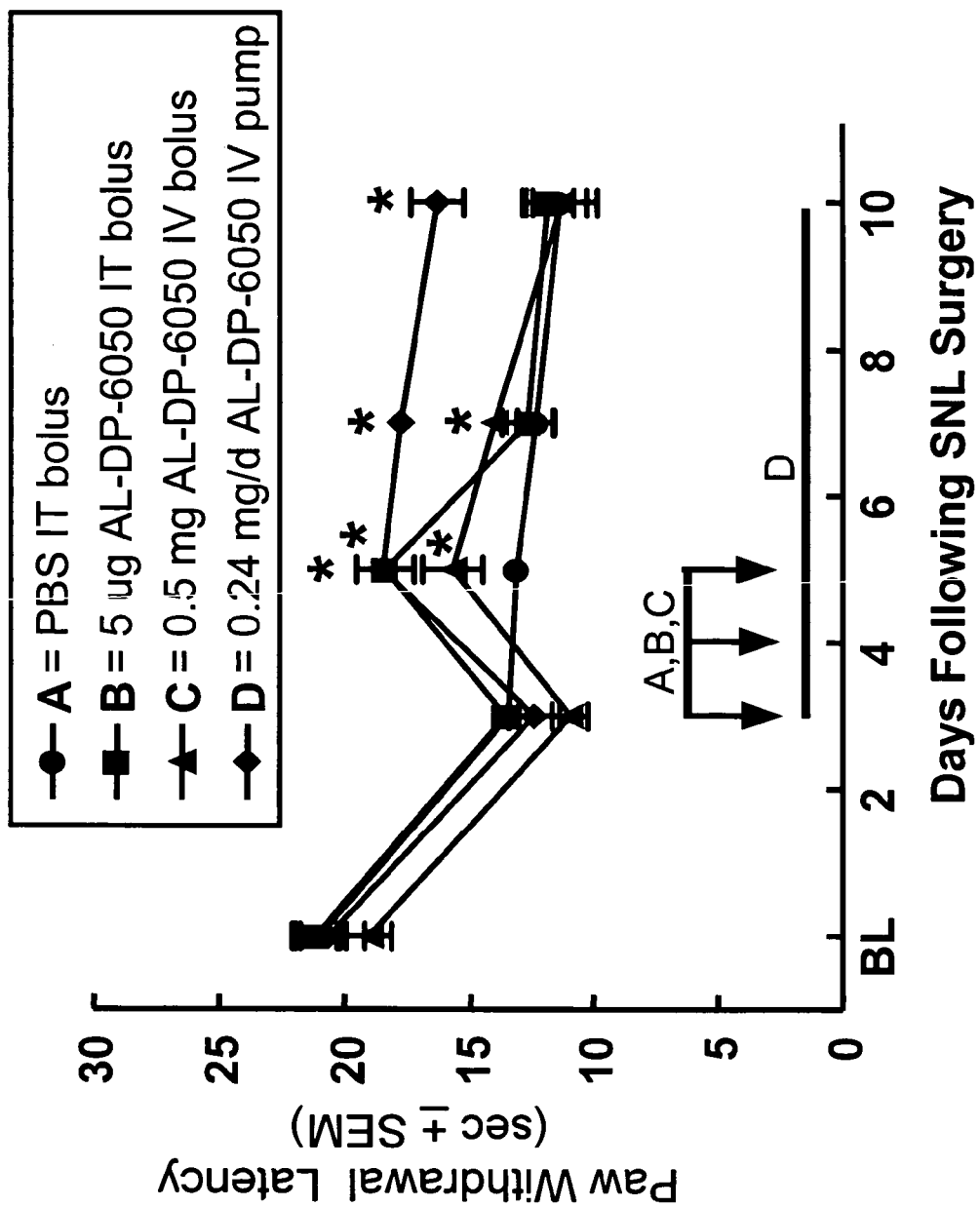
FIG. 14. In vivo efficacy of ND98-2.7 liposomal formulation of dsRNA AL-DP-6050 against spinal nerve ligation—induced thermal hyperalgesia in rats.

Intrathecal Bolus Administration of ND98-2.7 Liposomal Formulation of siRNA against Nav1.8 Alleviates Neuropathic Pain The effect of AL-DP-6050 (Table 1) against Nav1.8, formulated in ND98-2.7 (described below), and administered by intrathecal bolus injection, on spinal nerve ligation (SNL) -induced thermal hypersensitivity was evaluated in rats (FIG. 14). With the bolus intrathecal dosing paradigm evaluated (5 micrograms/bolus, daily), AL-DP-6050 was efficacious against SNL-induced thermal hypersensitivity.

Adult male Sprague-Dawley rats received unilateral ligation of the L5 and L6 spinal nerves on day 0 (SNL surgery). Two groups of rats (with 6 rats per group) were treated starting on day 3 after SNL surgery by intrathecal bolus injection with either the siRNA AL-DP-6050 against Nav1.8, formulated in ND98-2.7, or PBS. Intrathecal bolus injections (5 micrograms in 5 uL per injection) were administered to the lumbar level of the spinal cord daily on post-SNL days 3 through 5. Thermal hypersensitivity was assessed as described above.

Thermal responses were measured before SNL surgery to assess baseline responses (BL), and on post-SNL day 3 before treatment with test articles to verify that thermal hyperalgesia had developed fully. In rats treated with PBS, thermal hypersensitivity was pronounced, as expected, on post-SNL days 3, 5, 7 and 10 as evidenced by reduced thermal latencies. In contrast, in rats treated with AL-DP-6050 formulated in ND98-2.7 liposomes, by intrathecal bolus daily injection (5 micrograms/bolus), thermal latencies were substantially normalized on post-SNL day 5 (day 3 of treatment), demonstrating that the Nav1.8 siRNA, AL-DP-6050, formulated in ND98-2.7 liposomes and administered by intrathecal injection, is efficacious in vivo against SNL-induced thermal hyperalgesia. Moreover, the dose level of siRNA required for efficacy with the ND98-2.7 liposomal formulation (5 micrograms per day) was much lower than that observed for efficacy with the PBS formulation (300 micrograms per day).

These results demonstrate that siRNAs targeting Nav1.8, administered by intrathecal bolus injection and formulated in ND98-2.7 liposomes, are efficacious against experimental nerve injury-induced chronic pain in rats, and therefore, represent a novel approach to providing effective treatment of clinical neuropathic pain.

Intravenous Bolus and Continuous Pump Administration of ND98-2.7 Liposomal Formulation of siRNA against Nav1.8 Alleviates Neuropathic Pain The effect of AL-DP-6050 (Table 1) against Nav1.8, formulated in ND98-2.7, and administered by intravenous bolus injection or intravenous continuous pump infusion, on spinal nerve ligation (SNL) -induced thermal hypersensitivity was evaluated in rats (FIG. 14). With the bolus intravenous dosing paradigm evaluated (daily 0.5 mg/bolus, equivalent to approximately 2 mg/kg/bolus), and with the continuous intravenous pump paradigm evaluated (0.24 mg/day, equivalent to approximately 1 mg/kg/day), AL-DP-6050, formulated in ND98-2.7 liposomes, was efficacious against SNL-induced thermal hypersensitivity.

Adult male Sprague-Dawley rats received unilateral ligation of the L5 and L6 spinal nerves on day 0 (SNL surgery). Two groups of rats (with 6 rats per group) were treated starting on day 3 after SNL surgery by intravenous bolus injection or intravenous continuous pump infusion with the siRNA AL-DP-6050 against Nav1.8, formulated in ND98-2.7. Intravenous bolus injections (0.5 mg in 1 mL per bolus) were administered daily on post-SNL days 3 through 5. Intravenous continuous pump infusion (10 uL/hour, equivalent to 0.24 mg/day) was administered on post-SNL days 3 through 10 via a cannula in the jugular vein. Thermal hypersensitivity was assessed as described above.

Thermal responses were measured before SNL surgery to assess baseline responses (BL), and on post-SNL day 3 before treatment with test articles to verify that thermal hyperalgesia had developed fully. Thermal hypersensitivity was pronounced, as expected, on post-SNL day 3, before treatment, as evidenced by reduced paw withdrawal latencies. In contrast, in rats treated with AL-DP-6050 formulated in ND98-2.7 liposomes, by intravenous bolus daily injection (0.5 mg/bolus), thermal latencies were substantially normalized on post-SNL day 5 (day 3 of treatment), and post-SNL day 7 (2 days after the last intravenous bolus treatment) demonstrating that the Nav1.8 siRNA, AL-DP-6050, formulated in ND98-2.7 liposomes and administered by intravenous bolus injection, is efficacious in vivo against SNL-induced thermal hyperalgesia. Furthermore, in rats treated with AL-DP-6050 formulated in ND98-2.7 liposomes, by intravenous continuous pump infusion (0.24 mg/day), thermal latencies were substantially normalized on post-SNL days 5 (day 3 of treatment), 7 (day 5 of treatment) and 10 (day 8 of treatment).

These results demonstrate that siRNAs targeting Nav1.8, formulated in ND98-2.7 liposomes, and administered by intravenous bolus injection or intravenous continuous pump infusion, are efficacious against experimental nerve injury-induced chronic pain in rats, and therefore, represent a novel approach to providing effective treatment of clinical neuropathic pain. Moreover, these results demonstrate that ND98-2.7 liposomal formulation of siRNA can provide effective delivery of siRNA to sensory neurons of the dorsal root ganglion, with systemic administration.

Formulation Procedure

The lipidoid ND98.4HCl (MW 1487), Cholesterol (Sigma-Aldrich), and PEG-Ceramide C16 (Avanti Polar Lipids) were used to prepare lipid-siRNA nanoparticles.

Figure 15:
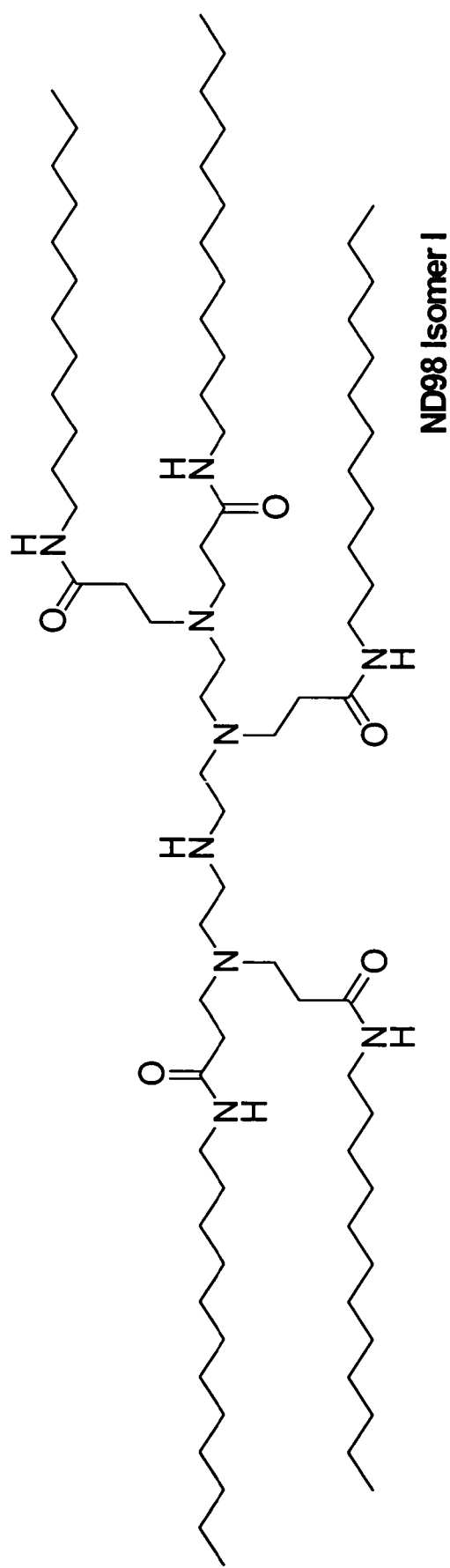
FIG. 15. Structure of ND98 lipid

Stock solutions of each in ethanol were prepared: ND98 (FIG. 15, ND98 Isomer I), 133 mg/mL; Cholesterol, 25 mg/mL, PEG-Ceramide C16, 100 mg/mL. ND98, Cholesterol, and PEG-Ceramide C16 stock solutions were then combined in a 42:48:10 molar ratio. Combined lipid solution was mixed rapidly with aqueous siRNA (in sodium acetate pH 5) such that the final ethanol concentration was 35-45.% and the final sodium acetate concentration was 100-300 mM. Lipid-siRNA nanoparticles formed spontaneously upon mixing. Depending on the desired particle size distribution, the resultant nanoparticle mixture was in some cases extruded through a polycarbonate membrane (100 nm cut-off) using a thermobarrel extruder (Lipex Extruder, Northern Lipids, Inc). In other cases, the extrusion step was omitted. Ethanol removal and simultaneous buffer exchange was accomplished by either dialysis or tangential flow filtration. Buffer was exchanged to phosphate buffered saline (PBS) pH 7.2.

Characterization of Formulations

Formulations prepared by either the standard or extrusion-free method are characterized in a similar manner. Formulations are first characterized by visual inspection. They should be whitish translucent solutions free from aggregates or sediment. Particle size and particle size distribution of lipid-nanoparticles are measured by dynamic light scattering using a Malvern Zetasizer Nano ZS (Malvern, USA). Particles should be 20-300 nm, and ideally, 40-100 nm in size. The particle size distribution should be unimodal. The total siRNA concentration in the formulation, as well as the entrapped fraction, is estimated using a dye exclusion assay. A sample of the formulated siRNA is incubated with the RNA-binding dye Ribogreen (Molecular Probes) in the presence or absence of a formulation disrupting surfactant, 0.5% Triton-X100. The total siRNA in the formulation is determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%.

dsRNA Expression Vectors

In another aspect of the invention, Nav1.8 specific dsRNA molecules that modulate Nav1.8 gene expression activity are expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., *Proc. Natl. Acad. Sci. USA* (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression vectors are preferably DNA plasmids or viral vectors. dsRNA expressing viral vectors can be constructed based on, but not limited to, adeno-associated virus (for a review, see Muzyczka, et al., *Curr. Topics Micro. Immunol.*(1992) 158:97-129)); adenovirus (see, for example, Berkner, et al., BioTechniques (1998) 6:616), Rosenfeld et al. (1991, Science 252:431-434), and Rosenfeld et al. (1992), *Cell* 68:143-155); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, *Proc. Natl. Acad. Sci. USA* (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-

1805; van Beusechem. et al., 1992, Proc. Nad. Acad. Sci. USA 89:7640-19 ; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Preferably, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single Nav1.8 gene or multiple Nav1.8 genes over a period of a week or more are also contemplated by the invention. Successful introduction of the vectors of the invention into host cells can be monitored using various known methods. For example, transient transfection, can be signaled with a reporter, such as a fluorescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

The Nav1.8 specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

We claim:

1. A double-stranded ribonucleic acid (dsRNA) for inhibiting the expression of a human Nav1.8 gene in a cell, wherein said dsRNA consists of a sense strand and an antisense strand that are complementary to each other, wherein said sense strand consists of SEQ ID NO:17 and said antisense strand consists of SEQ ID NO:18.

2. The dsRNA of claim 1, wherein said dsRNA, upon contact with a cell expressing said Nav1.8, inhibits expression of said Nav1.8 gene by at least 20%.

3. A cell comprising the dsRNA of claim 1.

4. A pharmaceutical composition for inhibiting the expression of the Nav1.8 gene in an organism, comprising a dsRNA and a pharmaceutically acceptable carrier, wherein the dsRNA consists of a sense strand and an antisense strand that are complementary to each other, wherein said sense strand consists of SEQ ID NO:17 and said antisense strand consists of SEQ ID NO:18.

5. The pharmaceutical composition of claim 4, wherein said dsRNA, upon contact with a cell expressing said Nav1.8 gene, inhibits expression of said Nav1.8 gene by at least 20%.

6. The pharmaceutical composition of claim 4, wherein said composition is formulated for administration selected from the group consisting of intrathecal infusion or injection, or intravenous infusion or injection.

7. A method for inhibiting the expression of the Nav1.8 gene in a cell, the method comprising:

(a) introducing into the cell a double-stranded ribonucleic acid (dsRNA), wherein the dsRNA consists of a sense strand and an antisense strand that are complementary to each other, wherein said sense strand consists of SEQ ID NO:17 and said antisense strand consists of SEQ ID NO:18; and (b) maintaining the cell produced in step (a) for a time sufficient to obtain degradation of the mRNA transcript of the Nav1.8 gene, thereby inhibiting expression of the Nav1.8 gene in the cell.

8. The method of claim 7, wherein said dsRNA, upon contact with a cell expressing said Nav1.8, inhibits expression of said Nav1.8 gene by at least 20%.

9. A method of treating, preventing or managing pain comprising administering to a patient in need of such treatment, prevention or management a therapeutically or prophylactically effective amount of a dsRNA, wherein the dsRNA consists of a sense strand and an antisense strand that are complementary to each other wherein said sense strand consists of SEQ ID NO:17 and said antisense strand consists of SEQ ID NO:18.

10. The method of claim 9, wherein said dsRNA, upon contact with a cell expressing said Nav1.8, inhibits expression of said Nav1.8 gene by at least 20%.

11. The method of claim 8, wherein said pain is selected from the group consisting of neuropathic pain and inflammatory pain.

* * * * *

UNITED STATES PATENT AND TRADEMARK OFFICE
CERTIFICATE OF CORRECTION

PATENT NO. : 7,582,745 B2
APPLICATION NO. : 11/593099
DATED : September 1, 2009
INVENTOR(S) : Dinah Wen-Yee Sah et al.

Page 1 of 1

It is certified that error appears in the above-identified patent and that said Letters Patent is hereby corrected as shown below:

Title page, Column 2 item [57] in the 4th line of the Abstract, please delete "that" and replace with "than."
Title page, Column 2 item [57] in the last line of the Abstract, please delete "gene" after "Nav1.8".
Column 365 Line 25-28, please delete claim 2, as it was not allowed (see Notice of Allowability dated April 28, 2009).

Signed and Sealed this

Thirteenth Day of July, 2010

David J. Kappos
*Director of the United States Patent and Trademark Office*